United States Patent [19]

Onodera et al.

[11] Patent Number: 5,407,581

[45] Date of Patent: Apr. 18, 1995

[54] FILTER MEDIUM HAVING A LIMITED SURFACE NEGATIVE CHARGE FOR TREATING A BLOOD MATERIAL

[75] Inventors: Hirokazu Onodera; Makoto Yoshida, both of Oita, Japan

[73] Assignee: Asahi Medical Co., Ltd., Tokyo, Japan

[21] Appl. No.: 32,487

[22] Filed: Mar. 17, 1993

[30] Foreign Application Priority Data

Mar. 17, 1992 [JP] Japan .................................. 4-090093

[51] Int. Cl.⁶ ....................... B01D 37/00; B01D 39/16
[52] U.S. Cl. ..................................... 210/654; 210/767; 210/321.69; 210/508; 210/929; 502/403
[58] Field of Search ............... 210/635, 636, 638, 639, 210/651, 660, 679, 692, 767, 321.69, 496, 500.21, 502.1, 508, 929, 652, 654; 502/402–404, 54.1; 530/354, 356, 394, 413, 415, 813, 815

[56] References Cited

U.S. PATENT DOCUMENTS

| | | |
|---|---|---|
| 4,046,720 | 9/1977 | Rembaum et al. . |
| 4,604,208 | 8/1986 | Chu et al. . |
| 4,880,548 | 11/1989 | Pall et al. . |
| 4,888,115 | 12/1989 | Marinaccia et al. ................. 210/636 |
| 4,936,998 | 6/1990 | Nishimura et al. .............. 210/502.1 |
| 5,021,160 | 6/1991 | Wolpert . |
| 5,051,185 | 9/1991 | Watanabe et al. .................. 502/403 |
| 5,286,449 | 2/1994 | Kuroda et al. ....................... 210/490 |

FOREIGN PATENT DOCUMENTS

| | | |
|---|---|---|
| 0341413 | 11/1989 | European Pat. Off. . |
| 0397403 | 11/1990 | European Pat. Off. . |
| 1249063 | 10/1989 | Japan . |
| 3502094 | 5/1991 | Japan . |
| 2061812 | 5/1981 | United Kingdom . |
| 8903717 | 5/1989 | WIPO . |

Primary Examiner—Robert A. Dawson
Assistant Examiner—W. L. Walker
Attorney, Agent, or Firm—Birch, Stewart, Kolasch & Birch

[57] ABSTRACT

Disclosed is a filter medium for treating a blood material selected from the group consisting of a leukocyte-containing suspension and plasma, comprising a polymeric, porous element having, in a surface portion thereof, a negative charge and having a surface electric charge of not smaller than $-30$ μeq/g of the polymeric, porous element. The filter medium and an apparatus having the filter medium packed in a casing having an inlet and an outlet, can be advantageously used for treating a blood material, for example, for separating leukocytes from a leukocyte-containing suspension including whole blood, for blood dialysis or for removing undesired proteinous substances and the like from whole blood or plasma by adsorption-filtration, while effectively controlling a concentration of bradykinin (which is causative of anaphylactic reactions) in a treated blood to a level not exceeding 4,000 pg/ml.

34 Claims, No Drawings

FILTER MEDIUM HAVING A LIMITED SURFACE NEGATIVE CHARGE FOR TREATING A BLOOD MATERIAL

BACKGROUND OF THE INVENTION

1. Field of The Invention

The present invention relates to a filter medium for treating a blood material. More particularly, the present invention is concerned with a filter medium for treating a blood material, comprising a polymeric, porous element having a surface electric charge of not smaller than $-30$ μeq/g of the polymeric, porous element. The filter medium of the present invention can advantageously be used for treating a blood material (to be used for, e.g., transfusion) without causing an increase in bradykinin concentration of the treated blood material to an unfavorable level (bradykinin is a cause of anaphylactic reactions in transfusion recipients). The present invention is also concerned with a blood-treating filter apparatus having the filter medium packed therein.

2. Discussion of Related Art

In recent years, in the field of blood transfusion, a leukocyte-free blood transfusion, in which leukocytes are removed from a blood material by means of a polyester non-woven fabric or a cotton fabric before the blood material is employed in transfusion, has increasingly been carried out. This is because it has been elucidated that side effects of transfusion, such as headache, nausea, chills and non-hemolytic feverish reaction, and side effects more serious to a recipient, such as allosensitization, post-transfusion GVHD (graft versus host disease) and viral infection, are mainly caused by leukocytes contained in the blood material employed for transfusion. Removal of leukocytes from blood is also conducted, using a filter material such as non-woven fabric or the like, for therapy of autoimmune diseases, such as systemic lupus erythematosus, chronic anticular rheumatism and multiple sclerosis; leukemia; cancer and the like, and for lowering the immune function of a patient prior to organ transplantation.

In the field of cardiac surgery, for example after a surgical operation for forming a coronary bypass, attempts are made to remove leukocytes from blood to be circulated to the patient. This is because leukocytes are likely to be activated at the site of the operation, and thereby emit superoxides which damage the site of the operation.

Further, after a surgical operation, blood obtained from a patient during the operation is sometimes recovered and returned to the operated patient. Such recovered blood is likely to be contaminated with tissue pieces, broken bone pieces, dust and the like, which are produced in during the operation of the patient. These contaminants are removed from the blood using a filter material before returning the blood to the patient. Furthermore, in adsorption-removal of an undesired substance from plasma by extracorporeal circulation of the plasma, a container with an adsorbent material packed therein is used. A filter medium is provided, not only at an outlet of the container, but also in a blood flow line downstream of the container, for preventing the adsorbent material or broken pieces thereof from leaking out of the container and blood flow line and, into the patient.

As the filter media for use in the above leukocyte-removing treatments, fibrous materials, such as cotton fabric or non-woven fabric, and porous materials having continuous pores, such as a sponge, are used, and various researches on these types of filter materials are made. The surfaces of these materials are generally treated so as to introduce an electrical negative charge thereto, so that hydrophilicity is imparted for increasing the wettability of the surfaces there of with blood.

In the fields of blood filtration, blood dialysis, plasma separation, plasma component filtration and the like, there are used membrane type filter media, such as hollow fiber membranes, flat membranes, or the like which are made of regenerated cellulose, polyacrylonitrile, polymethyl methacrylate, polysulfone, polyolefins, cellulose acetate and the like.

Furthermore, for removal or recovery of components of a body fluid, such as plasma, by adsorption-filtration, various types of adsorptive materials are used. Examples of adsorptive materials include an autoantibody-adsorptive material made of a porous polyvinyl alcohol substrate with tryptophane or phenylalanine immobilized thereon, a low density lipoprotein-adsorptive material made of a porous cross-linked cellulose substrate with dextran sulfate immobilized thereon, and an adsorptive material (for an antibody against an antiblood type substance) comprising a porous silica gel substrate with a saccharide immobilized thereon.

It is known that when blood is contacted with a material surface having an electrical negative charge, e.g. glass etc., blood coagulation factor XII in the blood is activated, so that kallikrein is produced from prekallikrein by the action of the activated blood coagulation factor XII. It is also known that the produced kallikrein causes endo-cleavage of high molecular weight kininogen at two internal sites thereof, to thereby produce a kinin (bradykinin). Further, it is known that the kinin is a substance which causes anaphylactic reactions, such as lowering of blood pressure, facial suffusion, conjunctival hyperemia, smooth muscle contraction, pain, etc., that is, the kinin is an anaphylatoxin. However, no quantitative study has been made with respect to the relationship between the production of kinin and the negative charge on the surface of a material. In particular, no investigation has been made with respect to an acceptable quantity of negative charge on the surface of a material for clinical use. Furthermore, no clinical knowledge has been obtained with respect to the relationships between the symptoms by anaphylactic reactions and the quantity of kinin.

SUMMARY OF THE INVENTION

The present inventors have made extensive and intensive studies with a view toward developing a filter medium which is capable of suppressing an increase in the bradykinin concentration of a blood material when the blood material is contacted with the filter medium for treatment of the blood material, so that even when the treated blood material is returned to a recipient, the recipient will not suffer from anaphylactic reactions caused by an increased bradykinin concentration. As a result of these studies, it has unexpectedly been found that the conventional filter media, which have a large quantity of negative charge introduced for improving the wettability thereof with blood, are likely to cause an increase in the bradykinin concentration of the blood material when they are used for treating the blood material, frequently leading to the occurrence of anaphylactic symptoms, that when the concentration of bradykinin in plasma of blood is increased to a level of 4,000 pg/ml or more of the plasma, serious anaphylactic symptoms are likely to occur, and that when a filter medium having a surface electric charge of not smaller than $-30$ μeq/g of the filter medium is used for treating blood, an increase in bradykinin content of the blood upon being contacted with the filter medium can be suppressed to maintain the bradykinin concentration in the blood at a level well below 4,000 pg/ml of the plasma of the blood, so that occurrence of serious anaphylactic symptoms is successfully prevented. The present invention has been completed, based on such novel findings.

Accordingly, it is an object of the present invention to provide a filter medium for treating a blood material, which can satisfactorily suppress an increase in bradykinin concentration of a blood material upon being contacted with the blood material.

It is another object of the present invention to provide a filter medium free of the bradykinin problem, for use in removing leukocytes from a leukocyte-containing suspension, including whole blood.

It is still another object of the present invention to provide a filter membrane free of the bradykinin problem, for use in separating an undesired substance from whole blood or plasma.

It is a further object of the present invention to provide an adsorptive composite type filter medium free of the bradykinin problem, for use in removing an undesired substance from whole blood or plasma.

It is still a further object of the present invention to provide an apparatus for treating a blood material having packed therein a filter medium for removing leukocytes from a leukocyte-containing suspension or having packed therein an adsorptive composite type filter medium for removing an undesired substance from whole blood or plasma.

The foregoing and other objects, features and advantages of the present invention will be apparent from the following detailed description and appended claims.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Essentially, according to the present invention, there is provided a filter medium for treating a blood material selected from the group consisting of a leukocyte-containing suspension and plasma, comprising a polymeric, porous element having, in a surface portion thereof, a negative charge, and having a surface electric charge of not smaller than $-30$ μeq/g of the polymeric, porous element.

The terminology "filter medium" used herein collectively means a medium for use in fractionating whole blood or for use in separating at least one blood or plasma component, a contaminant, or a foreign substance, by contacting a blood material with the medium, in which utilization is made of fractionation by size difference, dialysis, cohesion or sticking; adsorption by a physical or chemical action (such as electrostatic or hydrophobic action), or by biological interaction; or combinations thereof.

In the present invention, however, the filter media can be classified into the following three categories:

(1) A filter medium for use in removing, separating or recovering at least one substance selected from the group consisting of at least one preselected blood component (e.g., leukocytes, platelets or blood aggregates), a substance foreign to blood components (e.g., tissue pieces, broken bone pieces, broken pieces of a device) and a mixture thereof from a blood material. This type of filter medium comprises a polymeric, porous element selected from a filter fabric, such as a woven fabric, a non-woven fabric, a cotton fabric or the like; a porous article, such as a sponge; and a porous membrane. Another type of filter medium can be mentioned, for example, beads or a hollow fiber, onto which a monoclonal antibody or the like is immobilized in order to specifically separate a specific leukocyte fraction. This type of filter medium is also included in this category (1).

(2) A filter medium for use in separating whole blood into a blood cell product and plasma, or for use in separating whole blood or plasma, each containing at least one preselected substance, into the at least one preselected substance and the remaining whole blood or plasma substantially free of the at least one preselected substance. This type of filter medium is a porous membrane capable of separating substances by a molecular size difference between the substances. This type of filter medium is used for separating various undesired substances from plasma for treating patients suffering from renal failure by extracorporeal circulation of blood, for example, separating low molecular weight proteins by haemofiltration, or separating other low molecular weight components of plasma, such as electrolytes, urea, creatinine and the like by haemodialysis. This type of filter medium is also used for collecting or separating plasma from whole blood to conduct plasma pheresis or produce plasma products, or for fractionating plasma components, e.g., separation of macroglobulin and immune complex from albumin. Examples of porous membranes include hollow fiber porous membranes and flat porous membranes, each having a vast plurality of through-pores.

(3) A filter medium for use in separating whole blood or plasma, each containing at least one preselected substance, into the at least one preselected substance and a remaining whole blood or plasma substantially free of the at least one preselected substance by adsorption-filtration. This type of filter medium comprises a polymeric, porous element comprised of an adsorptive composite. The adsorptive composite comprises a polymeric, porous substrate having, on a surface thereof including pore surfaces, functional groups capable of selectively binding the above-mentioned at least one preselected substance thereto. Examples of adsorptive composites include beads having polyanions immobilized thereon; hydrophobic resin; porous beads having immobilized thereon a saccharide, an amino acid, or an oligomer or polymer thereof; porous beads having immobilized thereto an antibiotic or other pharmaceutical substances; and those which are obtained by substituting fibrous materials for the substrate beads of the above-mentioned bead composites. This type of filter medium is used for removing, separating, or collecting plasma proteins, such as cholesterol, an autoantibody, an immune complex, a bilirubin, a hydrophobic amino acid, a proteinous pharmaceutical substance, and the like; or plasma components, such as a lipid, an amino acid, a nucleic acid, a low molecular weight compound, and the like.

In the filter medium of the present invention, it is essential that the polymeric, porous element have, in a surface portion thereof, a negative charge and have a surface electric charge of not smaller than $-30\ \mu eq/g$ of the polymeric, porous element.

With respect to the manner in which the polymeric, porous element exhibits a surface electric charge of not smaller than $-30\ \mu eq/g$, there are three instances. In the first instance, only a negative charge is present in an amount such that the surface exhibits a surface electric charge of not smaller than $-30\ \mu eq/g$. In the second instance, both positive and negative charges are present but the quantity of negative charge is larger than the quantity of positive charge, so that as a whole, a negative charge is exhibited in the range of not smaller than $-30\ \mu eq/g$ as a balance (difference) between the total quantity of positive charges and the total quantity of negative charges. In the third instance, both positive and negative charges are present but the quantity of positive charge is larger than the quantity of negative charge, so that as a whole, a positive charge is exhibited as a balance (difference) between the total quantity of positive charges and the total quantity of negative charges.

The surface electric charge of the polymeric, porous element Can be either positive or negative as long as it is not smaller than $-30\ \mu eq/g$. According to the present invention, even when the surface electric charge is positive, the polymeric, porous element is required to have a negative charge in a surface portion of the polymeric, porous element.

When the surface of the polymeric, porous element contains both positive and negative charges and exhibits a positive charge as a whole, the presence of the negative charge can be determined by an easy method in which a dye having a positive charge is adsorbed on the negative charge groups on the surface of the polymeric, porous element, and the negative charge quantity is obtained from an amount of the adsorbed dye. For example, 0.01 g of the polymeric, porous element is placed in a sealable, glass vessel and 10 ml of a 0.013 wt. % aqueous solution of safranine O is added. The vessel is sealed and shaken at 30° C. for 48 hours. A supernatant is taken and subjected to absorption spectrometry at 515 nm to obtain an absorbance. On the other hand, a blank test in which a polymeric, porous element is not used, is conducted to obtain an absorbance. The difference between the two absorbances is taken as the absorbance due to the tested polymeric, porous element. The same test as mentioned above is preliminary, and is conducted with respect to samples having known quantities of negative charges, to thereby obtain a calibration curve of the relationships between the amount of adsorbed safranine O and the quantity of negative charge. In this manner, the presence and amount of a negative charge is determined.

Measurement of a surface electric charge of the polymeric, porous element can be done as follows.

As mentioned above, the filter medium comprising the polymeric, porous element is classified into three categories (1), (2) and (3).

With respect to the filter medium of category (3), which is represented by an adsorptive composite, the surface electric charge is measured by the salt-splitting, neutralization titration method, which is well known in the art.

As mentioned above, with respect to the mode in which the adsorptive composite exhibits a surface electric charge of not smaller than $-30\ \mu eq/g$, there are three instances. In the first instance described above, the quantity of negative charge is measured to determine a surface electric charge. In the second instance described above, an apparent negative charge is measured to determine a negative surface electric charge as a balance between the positive and negative charges. In the third instance, an apparent positive charge is measured to determine a positive surface electric charge as a balance between the positive and negative charges. Following are respective methods for measuring surface electric charges with respect to the above three instances:

(1) First instance (only negative charge is present)

5 ml of the adsorptive composite of the present invention (which is in the same swollen state as in the actual filtration operation) is placed on a glass filter and then, gently washed with 500 ml of distilled water for injection. The washed adsorptive composite is placed in a beaker. 2N hydrochloric acid is added to the adsorptive composite, and the resultant mixture is stirred for 30 minutes. Then, the adsorptive composite is transferred from the mixture onto a glass filter and then, gently washed with 2 liters of distilled water for injection, to obtain a filtrate. At this stage, it is confirmed that the pH value of the obtained filtrate is in the range of from 4 to 7. If the pH value of the filtrate is lower than 4, the washing with distilled water for injection as mentioned above is repeated, so that the pH value becomes a value in the above range. On the other hand, if the pH value of the filtrate is higher than 7, the stirring in 2N hydrochloric acid for 30 minutes and washing with distilled water for injection as mentioned above are repeated, so that the pH value becomes a value in the above range. After the confirmation of the pH value, the adsorptive composite is placed in a beaker. To the adsorptive composite is added 50 ml of a 4 % aqueous sodium chloride solution, and the mixture is stirred for 1 hour. The resultant mixture is filtered by means of a glass filter to thereby obtain a filtrate. 20 ml of the obtained filtrate is titrated with 0.01N sodium hydroxide. From results obtained by the above salt-splitting, neutralization titration method, a negative charge is determined.

(2) Second instance (both positive and negative charges are present, wherein the negative charge > the positive charge)

When both positive and negative changes are present, equimolar amounts of the positive and negative charges are neutralized with each other through ionic bonding. Therefore, an apparent negative charge as a balance between the total amounts of the negative and positive charges is determined by the salt-splitting, neutralization titration method in substantially the same manner as in the determination of a negative charge in (1) above.

(3) Third instance (both positive and negative charges are present, wherein the negative charge < the positive charge)

When both positive and negative changes are present, equimolar amounts of the positive and negative charges are neutralized with each other through ionic bonding. Therefore, an apparent positive charge as a balance between the total amounts of the positive and negative charges is determined as follows.

5 ml of the adsorptive composite of the present invention (which is in the same swollen state as in the actual filtration operation) is placed on a glass filter and then, gently washed with 500 ml of distilled water for injection. The washed adsorptive composite is placed in a beaker. 2N sodium hydroxide is added to the adsorptive composite, and the resultant mixture is stirred for 30 minutes. Then, the adsorptive composite is transferred from the mixture onto a glass filter and then, gently washed with 2 liters of distilled water for injection, to obtain a filtrate. At this stage, it is confirmed that the pH value of the obtained filtrate is in the range of from 7 to 10. If the pH value of the filtrate is lower than 7, the stirring in 2N sodium hydroxide for 30 minutes and the washing with distilled water for injection as mentioned above is repeated, so that the pH value becomes a value in the above range. On the other hand, if the pH value of the filtrate is higher than 10, the washing with distilled water for injection as mentioned above is repeated, so that the pH value becomes a value in the above range. After the confirmation of the pH value, the adsorptive composite is placed in a beaker. To the adsorptive composite is added 50 ml of a 4 % aqueous sodium chloride solution, and is stirred for 1 hour. The resultant mixture is filtered by means of a glass filter to thereby obtain a filtrate. 20 ml of the obtained filtrate is titrated with 0.01N hydrochloric acid. From results obtained by the above salt-splitting, neutralization titration method, an apparent positive charge is determined.

With respect to the method for measuring surface electric charges of the filter media of categories (1) and (2), the above-mentioned salt-splitting, neutralization titration method is not suitable because these filter media have relatively small specific surface areas (generally less than 5 m$^2$/g). Examples of suitable porous elements for filter media of category (1) include woven fabrics, non-woven fabrics and sponge, and Examples of suitable porous elements for filter media of category (2) include porous membranes, such as hollow fiber porous membranes and flat porous membranes. As a result of the investigations by the present inventors, it has been found that the surface electric charges of the polymeric, porous elements for the filter media of categories (1) and (2) can be easily determined by a so-called iodide method, in which iodine is reacted with iodide ions in an organic solvent, such as an alcohol, in the presence of the polymeric, porous element having a negative charge, wherein a negative charge (when only a negative charge is present) or an apparent negative charge (as a balance between the positive and negative charges when both positive and negative charges are present) functions as a catalyst, so that the reaction proceeds to form triiodide complex ions depending on the quantity of the negative charge, and the amount of the thus formed triiodide complex ions is measured by absorption spectrometry to thereby determine the quantity of the negative charge or apparent negative charge on the surface of the polymeric, porous element. When the surface of the polymeric, porous element exhibits an apparent positive charge as a balance between the positive and negative charges, the above-mentioned reaction for forming triiodide complex ions does not proceed, so that confirmation can be made at least with respect to the fact that the polymeric, porous element has a surface electric charge of not smaller than $-30$ $\mu$eq/g.

Following is a detailed explanation on the so-called iodide method developed.

A polymer, porous element is immersed in an organic solvent, such as alcohol, and in the resultant system, iodine is reacted with iodide ions to form triiodide complex ions. The triiodide complex ions are subjected to absorption spectrometry at a wavelength of 359 nm.

On the other hand, materials having, in surface portions thereof, known amounts of negative charges, such as carboxyl groups, are provided. Substantially the same operations as mentioned above are conducted to prepare a calibration curve. Using this calibration curve, the negative charge or apparent negative charge of the polymeric, porous element can be determined. In absorption spectrometry, an absorbance at 290 nm, or both absorbances at 290 nm and 359 nm, can be utilized for determining the surface negative charge.

As substances to be used for forming triiodide complex ions, all iodides can be used. Representative Examples of iodides include potassium iodide, sodium iodide, magnesium iodide, zinc iodide, manganese iodide, ferrous iodide and lithium iodide, which are all soluble in an alcohol. Of these iodides, especially preferred are potassium iodide and sodium iodide from viewpoints of solubility in an alcohol, availability, and ease of storing. With respect to iodine, not only can a small amount of iodine contained in the iodide be utilized, but also additional iodine can be advantageously used when the amount of negative charge on the polymeric, porous element is relatively large. When the amount of negative charge to be determined is small, satisfactory results can be obtained using a small amount of iodine contained in the iodide. Employable iodides are not limited to the above-mentioned examples. Alcoholic solvents to be used in the above iodide method include various alcohols, such as methanol, ethanol, n-propanol, isopropyl alcohol and t-butanol; and mixtures of the alcohols with water and/or an organic solvent exhibiting no absorption at 359 nm, with the proviso that these alcoholic solvents are capable of dissolving iodides but incapable of dissolving the polymeric, porous element and with the proviso that these alcoholic solvents do not exhibit absorption for visible or ultraviolet rays at an wavelength of between 200 and 500 nm, preferably between 250 and 450 nm, more preferably between 300 and 450 nm. Preferred alcoholic solvents are alcohols containing less than 50 volume % of water, and most preferred solvents are 100% pure alcohols. Especially, in measuring surface electric charges of polyester nonwoven fabrics, 100% pure methanol is most preferred in view of good affinity between the fabric material and the solvent and good solubility for iodides.

Concentrations of iodine and iodide in the alcoholic solvents are not particularly limited as long as the iodine and iodide are present in a dissolved state at reaction temperatures used for the iodide method.

Absorption at about 359 nm is exhibited by triiodide complex ions (formed by the reaction of iodine and iodide in an alcoholic solvent in the presence of the surface negative charger as a catalyst, of the polymeric, porous element) in the alcoholic solvent. Accordingly, the absorption by triiodide complex ions at about 359 nm increases in proportion to the amount of a surface negative charge of the polymer, porous element. An increase in absorption with time corresponds to an increase in formed triiodide complex ions. By this iodide method, it is possible to determine a surface negative charge present even in an amount as small as a few μeq/g. Further, the amount of formed triiodide complex ions is measured as an absorbance of rays in the ultraviolet range, so that accurate measurement is possible. Furthermore, since the amount of negative charge is measured as the amount of formed triiodide complex ions, the difference in negative charge is amplified as a difference in absorbance, so that measurement can be done with high precision.

When the polymeric, porous element contains a solvent-extractable substance, the extracted solvent sometimes exhibits absorption at a wavelength for measurement, or sometimes exhibits a surface negative charge, thereby adversely affecting measurement by the iodide method. Therefore, it is preferred that such a solvent-extractable substance be sufficiently removed beforehand or that a non-solvent for such a substance be used. The study by the present inventors reveals that, especially when oligomers are extracted from a polyester porous element beforehand, good measurement can be done without suffering from an adverse influence as long as the absorbance of rays in the ultraviolet range due to the extracted oligomers is 0.1 or less, preferably 0.01 or less, more preferably 0.001 or less under the same conditions as used for actual measurement operation, relative to the absorbance due to the polymeric, porous element.

In treating a blood material, an anticoagulant is used. Examples of anticoagulants include those exhibiting an antithrombin activity, such as heparin; those exhibiting an anticoagulation activity by forming a complex with a bivalent ion, such as citric acid or a salt thereof, ethylenediaminetetraacetic acid or a salt thereof, etc.; and a proteinase inhibitor, such as nafamostat mesilate, and the like. By the research of the present inventors, it has been found that nafamostat mesilate acts to inhibit the activity of kallikrein to produce bradykinin (hereinafter, frequently referred to simply as "kinin"). Further, it has been found that the anticoagulant exhibiting an anticoagulation activity by forming a complex with a bivalent ion also acts to inhibit the activity of kininase to decompose kinin. Although any one of the above-mentioned anticoagulants can be used for blood, when an anticoagulant exhibiting an anticoagulation activity by forming a complex with a bivalent ion is used in treating blood by means of a filter medium having a surface electric charge of smaller than $-30$ μeq/g, especially smaller than $-50$ μeq/g, a problem occurs such that an increase in kinin concentration of the blood treated by the filter medium is remarkably high. Further, when an angiotensin converting enzyme inhibitor, such as Captopril, Enarapril etc., is present in plasma to be treated by the filter medium, decomposition of kinin is inhibited to thereby cause a remarked increase in kinin concentration of blood treated by the filter medium. Therefore, for evaluating an unfavorable formation of bradykinin due to the employed filter media, citric acid and the like are preferably used as anticoagulants. From the viewpoint of practical safety, nafamostat mesilate is preferred, since an increase in kinin concentration can be suppressed.

It has also been found that when blood containing 0.1 to 20 wt. % of citric acid or a salt thereof is subjected to an in vitro blood experiment, wherein the blood is contacted with a filter medium having a surface electric charge of smaller than $-30$ μeq/g, especially smaller than μ50 μeq/g of the medium in a flask, a kinin concentration of plasma is increased to a level of 4,000 pg/ml or more of the plasma. It has been further found that a practical use of such a filter medium having a small surface electric charge causes an increase in kinin concentration in plasma to a level of 4,000 pg/ml or more of the plasma, and that when the plasma having a high concentration of kinin is injected to a human body, anaphylactic reactions, such as facial suffusion, lowering of blood pressure, etc., are likely to occur. Accordingly, filter media not causing an increase in kinin concentration of blood to 4,000 pg/ml has been desired in the art for obtaining a safe blood material which does not cause any serious side effects.

The present inventors have noticed the importance of relationships between the production of kinin and the quantity of negative charge on the surface of the filter material, and unexpectedly found that there is an apparent correlation therebetween, and that an increase in kinin concentration of blood treated by a filter medium can be prevented by decreasing the quantity of negative charge in a surface of the filter medium. The inventors have made further studies for obtaining a filter medium having a small negative charge in a surface thereof, and have succeeded in producing filter media having a surface electric charge of not smaller than $-30$ μeq/g of the media.

When the surface electric charge of a filter medium is not smaller than $-30$ μeq/g of the medium, the activation of blood coagulation factor XII in plasma is suppressed, so that the increase in kinin concentration becomes small, and so that, in an in vitro experiment, the concentration of kinin in blood plasma does not exceed the level of 4,000 pg/ml of the plasma.

As mentioned above, the surface electric charge of the filter medium is $-30$ μeq/g or larger, but more preferably not smaller than $-25$ μeq/g, most preferably not smaller than $-20$ μeq/g of the medium.

On the other hand, from viewpoints of desired wettability and compatibility of the medium with blood as well as low non-specific adsorptivity for plasma proteins, the surface electric charge is preferably not greater than $-0.001$ μeq/g, more preferably not greater than $-0.1$ μeq/g, most preferably not greater than $-1$ μeq/g of the medium.

Generally, the surface electric charge is expressed in terms of the charge density per unit surface area of the filter medium. However, according to the study by the present inventors, there are many cases in which even if the charge density per unit surface area is low, a large amount of kinin is produced when the surface area is large. Thus, it is not preferred to express the surface electric charge in terms of the charge density per unit area.

As mentioned above, when blood or plasma is contacted with a filter medium, blood coagulation factor XII is activated, so that kallikrein is produced from prekallikrein by the action of the activated blood coagulation factor XII. The produced kallikrein causes endo-cleavage of high molecular weight kininogen at two sites to thereby produce bradykinin. Thus, the kinin concentration of the blood is increased. In the present invention, the unfavorable formation of kinin is evaluated in terms of an increase in kinin concentration of a treated blood material.

According to the study of the present inventors, when the surface electric charge of a filter medium is small, especially when the surface electric charge becomes smaller than −100 μeq/g of the medium, the increase in kinin concentration of a treated blood becomes extremely large. On the other hand, when the surface electric charge is large, the formation of kinin becomes low. That is, the formation of kinin is in reverse proportion to the surface electric charge.

When the surface electric charge of a filter medium is smaller than −30 μeq/g of the medium, it is likely that a large amount of kinin is produced, leading to clinical problems. When the surface electric charge is not smaller than −30 μeq/g of the medium, the unfavorable formation of kinin is can be effectively suppressed.

The term "surface" of the filter medium, used herein, means all surfaces of the filter medium which, in treating blood, are capable of contacting the blood material, and does not include inner portions of the filter medium which cannot contact the blood material. When the surface comprises a treated surface (subjected to surface treatment), the treated surface is included in the "surface" used herein, as long as the treated surface can contact the blood material.

The term "surface electric charge" used herein means all electric charges existing at or on the surface of the filter medium and portions near the surface (more illustratively stated, portions up to 10 angstroms in depth from the surface), which are capable of exerting electrostatic actions on blood components.

The term "negative charge" used herein means those which are ascribed to acidic functional groups exhibiting negative charges at a neutral pH value, e.g. a carboxyl group, a phosphoric acid group, a phosphorous acid group, a sulfonic acid group, a sulfuric ester group, a sulfurous group, a hyposulfurous acid group, a sulfide group, a phenol group, hydroxysilyl group and the like. The acidic functional groups are not restricted to the above examples. Of the above examples, a carboxyl group, a sulfonic acid group and a sulfuric ester group are especially preferred, because these three groups exhibit high strength of charge.

The term "negative charge" used herein means not only negative charges which are ascribed to negative functional groups originally contained in the filter medium per se, but also those which are introduced due to the hydrolysis of the filter medium surface by heating, treatment with chemicals, such as oxides, acids and alkaline solutions, radiation and the like, in the process of producing the filter medium. Negative charges also include those which are ascribed to compounds having negative charges, which are introduced to the filter medium by covalent bonding, grafting, physical adsorption, ion bonding, embedding and the like. Further, negative charges include not only those which are introduced as a result of graft-polymerizing a negative charge-containing monomer onto the filter medium by radiation-grafting or plasma-grafting, but also those which are generated (when a negative charge-free monomer is graft-polymerized onto a substrate) in the monomer, or in the substrate.

In addition to the negative functional groups, positive functional groups and/or nonionic functional groups may coexist at or on a surface portion of the filter medium. Examples of nonionic functional groups include: nonionic hydrophilic functional groups, such as a hydroxyl group, a polyethylene glycol chain, an amide group (such as dimethylamide group, diethylamide group or diisopropylamide group), an aromatic polyester chain (such as a polyethylene terephthalate chain or polybutylene terephthalate chain), an aliphatic polyester chain, a polyether chain (such as methylene glycol or propylene glycol) and a polycarbonate chain, which are effective for improving hydrophilic properties of the filter medium; and nonionic hydrophobic functional groups, such as an alkyl group, a fluoroalkyl chain, and an allyl chain, which are effective for imparting hydrophobic properties to the filter medium. Although any functional groups of the above examples can coexist in the filter medium, nonionic hydrophilic functional groups or chains having these hydrophilic groups are preferred because those groups or chains have excellent effects especially on filter media for removing leukocytes.

Examples of positive functional groups include those derived from amines and amine derivatives, e.g. tertiary and quaternary amino groups. It is preferred that these groups have a base dissociation constant, pKb, of 2.0 or more, more preferably 3.0 or more. It is further preferred that the positive functional groups be those which are less likely to adsorb heparin thereon, because heparin is generally used as an anticoagulant for blood material. From this point of view, preferred are positive functional group represented by the following formula:

wherein each of $R^1$, $R^2$ and $R^3$ is not specifically restricted, provided that any of these three substituents, e.g. $R^1$, is linked to a main chain of the polymer of the polymeric, porous element of the filter medium by covalent bonding. Each of these substituents may be a hydrogen atom, a hydrocarbon group, such as a methyl group, an ethyl group, a propyl group, a phenyl group, a benzyl group or the like, or a substituent containing a heteronuclear species, such as methylol, ethylol and the like. Furthermore, the positive functional group of the above formula may have a structure such that two substituents among the three substituents, e.g. $R^1$ and $R^2$ (or $R^3$), constitute the main chain of the filter medium.

$R^2$ and $R^3$ may be bonded to each other to form a ring structure to provide ring compounds, such as pyridine, imidazole, piperidine, pyrrol, pyrimidine and the like.

Examples of positive functional groups include allylamine, diallylamine, N,N-dimethylallylamine, N,N-diallylpiperazine, N,N-diallylaniline, N,N-diallylmelamine, aminostyrene, N,N-dimethylaminostyrene, N,N-diethylaminostyrene, vinylbenzylamine, vinylphenethylamine, N,N-dimethylvinylphenethylamine, N,N-diethylvinylphenethylamine, N-propylvinylphenethylamine, vinylpyridine, 2-methyl-5-vinylpyridine, 2-ethyl-5-vinylpyridine, 2-vinylquinoline, 2-vinylimidazole, 4-vinylimidazole, vinylpyrazoline, vinylpyrazine, 4-vinylpyrimidine, vinylamine, vinylcarbazole, ethyleneimine, N-phenylethyleneimine, N,N-diethyl-N-vinylphenethylamine, diethylaminoethyl methacrylate, dimethylaminoethyl methacrylate, diethylaminoethylstyrene and the like; and oligomers and polymers which have any of the above-mentioned monomers as monomer units thereof. Furthermore, quaternary ammonium groups derived from the above-mentioned compounds can also be used as positive functional groups.

It is especially preferred that each of $R^2$ and $R^3$ be a hydrogen atom or an alkyl chain having 1 to 12 carbon atoms, more preferably 1 to 6 carbon atoms.

Preferred examples of positive functional group include diethylaminoethylstyrene, N,N-diethyl-N-vinylphenethylamine, diethylaminoethyl methacrylate, dimethylaminoethyl methacrylate, diethylaminoethyl acrylate and dimethylaminoethyl acrylate.

Further, the positive functional group may be a copolymer of a monomer selected from the above-mentioned monomers and at least one comonomer selected from, e.g. hydroxystyrene, hydroxymethylstyrene, vinyl alcohol, 2-hydroxyethyl acrylate, 2-hydroxyethyl methacrylate, segmented polyurethane, segmented polyester and the like. It is especially preferred that the copolymer has hydroxyl groups from the viewpoint of improvement in compatibility with blood. The manner in which the hydroxyl groups are bonded to the copolymer is not specifically restricted. It is preferred that the copolymer contain 1 to 50% by weight of monomer units represented by the above formula and monomer units having hydroxyl groups.

When the filter medium has only negative functional groups, or a combination of negative functional groups and nonionic functional groups at or on the surface portion thereof, that is, when the filter medium has no positive functional group in the surface portion, the amount of negative charge at or on the a surface of the filter medium is determined only by the negative functional groups present therein. On the other hand, When both negative functional groups and positive functional groups are present at or on the surface portion, the negative charge is determined as a balance (difference) between the positive charge and the negative charge, both of which interact with to each other in the blood material having a pH value of 5 to 9, which is the same pH conditions as in practical use of the filter medium. This so-called apparent surface electric charge is required to be not smaller than $-30$ μeq/g.

With respect to a method for achieving a surface electric charge of not smaller than $-30$ μeq/g, the following methods can be mentioned:

(1) a method in which hydrolysis or thermal decomposition of a material of the filter medium in the process of producing the medium, is prevented by, e.g., lowering the water content of the feedstock polymer chips, or by lowering the temperature or water content of the chips during the step of melting the chips;

(2) a method in which generation of peroxides in the step of subjecting the filter medium to a treatment with radiation, electron beam, plasma irradiation or the like, is prevented by lowering the amount of coexisting oxygen;

(3) a method in which the negative functional groups of the filter medium, are chemically blocked by, e.g. covalent-bonding a non-negative compound to the negative functional group;

(4) a method in which the negative functional groups, are physically covered by, e.g. coating the filter medium with a non-negative compound; and (5) a method in which the negative charges in the surface are electrostatically neutralized by chemically or physically introducing positive functional groups.

Any method of the above five methods can be employed in the present invention. A preferred method varies depending on the type and application of the filter medium. However, in general, the method for coating the filter medium surface with a compound or a polymer having hydrophilic, neutral or positive functional groups, is practically preferred because it is the easiest method.

As described above, the filter media are can be classified into three categories (1), (2) and (3).

In accordance with the above classification, each embodiment of the present invention is described below.

In one form of the filter medium of the present invention, the filter medium is used for in separating at least one substance selected from the group consisting of at least one preselected blood component, a substance foreign to blood components, and a mixture thereof from the blood material. The filter medium comprises a polymeric, porous element having, in a surface portion thereof, a negative charge and having a surface electric charge of not smaller than $-30$ μeq/g of the polymeric, porous element, wherein the polymeric, porous element has an average pore diameter of from 1 to 100 μm and a total pore volume of from 0.4 to 0.95 ml/ml of the polymeric, porous element, and wherein the sum of respective pore volumes of pores of the polymeric, porous element which have a pore diameter of from 1 to 100 μm is 75% or more, based on the total pore volume.

More particularly, this form of the filter medium is used for removal of leukocytes in the field of transfusion, removal of leukocytes for therapy of autoimmune diseases, removal of leukocytes from blood to be circulated after a surgical operation in cardiac surgery, removal of foreign substances, such as broken bone pieces, from blood collected during surgical operation, prevention of leakage of pieces of an adsorbent material used in an extracorporeal circulation into a patient, or the like. The filter medium for removing leukocytes generally comprises a preliminary filter medium for removing gels, microaggregates and the like, and a main filter medium for adhesion and/or filtration-removing leukocytes.

The present inventors have conducted measurements of the electric charges in surface portions of various types of conventional filter media containing negative charges in a surface portion thereof, and found that all of such conventional filter media have a surface electric charge of smaller than $-50$ μeq/g of the filter medium.

A filter medium having a surface electric charge of smaller than $-50$ μeq/g (namely, for example, $-53$ μeq/g, $-55$ μeq/g or so) causes a problem in that a large increase in bradykinin concentration of the blood plasma is caused by treatment with the medium. On the other hand, a filter medium having too high a quantity of positive charge in a surface portion thereof, causes problems such as that the medium does not adsorb activated complements at all which are produced, during blood perfusion, in an inner surface of a casing having the medium packed therein or inner surfaces of connecting tubes, to thereby cause the activated complements to directly enter a human body, that the medium adsorbs heparin which is used as an anticoagulant in an extra-corporeal circulation of blood, to thereby cause blood coagulation, and that the medium is likely to adsorb acidic proteins which contain trace amounts of useful proteins, such as platelet-derived proliferation factors and α1-acidic glycoproteins. Thus, a filter medium having too much of a quantity of positive charges at or on a surface portion thereof is not necessarily preferable in view of these problems.

On the other hand, a filter medium having a negative charge at or on a surface portion thereof has acidic functional groups having high hydrophilicity, thereby rendering the medium extremely favorable with respect to wettability of the medium with a blood material.

Examples of materials to be used for preparing polymeric, porous element of the filter medium of the present invention include polyesters, such as polyethylene terephthalate, polybutylene terephthalate and polyoxyethylene terephthalate; polyacrylonitrile; polyamides, such as nylon 6 and nylon 6, 6; aromatic polyamide; polystyrene and derivatives thereof; polyolefins, such as polyethylene, polypropylene and polybutene; polymeric compounds which are obtained by polymerization of methacrylate derivatives, such as methyl methacrylate and ethylmethacrylate; polymeric compounds which are obtained by polymerization of acrylate derivatives, such as methyl acrylate and ethyl acrylate; polymeric compounds, such as polytrifluorochloroethylene, polyvinyl formal, polysulfones, polyurethanes, polyvinyl acetal and polycarbonates; homopolymers, copolymers, or block copolymers of the above-mentioned polymeric compounds, a blend or alloy thereof; cellulose and/or a cellulose derivative; regenerated fibers; a blend or alloy of regenerated fibers with the above-mentioned synthetic, polymeric compounds.

Among the above-mentioned materials, synthetic polyesters, such as polyethylene terephthalate, polybutylene terephthalate and polyoxyethylene terephthalate are especially preferable with respect to fabricatability into a non-woven fabric, to controllability of a fiber diameter of the non-woven fabric, and also to the state of pores formed by fibers (the state of formed pores greatly affects the removal of leukocytes and other blood components from a blood material). Synthetic polyesters are particularly preferred with respect to wettability of the materials with blood.

The porous element of the filter medium of the present invention can be produced by conventional techniques. A porous article, as an example of such porous elements, can be produced by any of the decomposition-foaming methods (such as the atmospheric foaming method, pressure foaming method, extrusion foaming method or injection foaming method), the solvent evaporation method, the gas incorporation method, the chemical reaction method, the elution method and the sintering method, which are all conventionally known. The produced porous article is preferably subjected to secondary processing, such as hot-press compression and swelling with an appropriate liquid, so that the porous article has a specific pore diameter distribution as defined above, which is requisite to this form of the filter medium of the present invention.

On the other hand, a fibrous, porous article as another example of the above-mentioned porous element can be produced by conventional techniques, such as the melt blow method and the flash spinning method. The produced fibrous, porous article is preferably subjected to secondary processing, such as press compression, thermal shrinkage and treatment with an appropriate liquid, so that the article has a specific pore diameter distribution which is requisite of this form of the filter medium of the present invention.

The surface of the porous element of the filter medium of the present invention can be modified with a compound having a low or high molecular weight by conventional techniques, such as covalent bonding or ionic bonding, radiation-graft copolymerization or plasma treatment, physical adsorption, embedding, or precipitate immobilization. For example, there is known a conventional method in which the surface of the porous element is modified by conventional techniques, such as graft copolymerization of polymeric compounds or monomers thereof by radiation or plasma treatment, or covalent bonding (Japanese Patent Application Laid-Open Specification Nos. 1-249063 and 3-502094). Examples of monomers and polymeric compounds for use in surface modification of a porous element include vinyl monomers (for example, methacrylic acid; acrylic acid; acrylic acid or methacrylic acid derivatives, such as 2-methacryloyloxyethyl succinate, mono (2-acryloyloxyethyl) acid phosphate, 2-sulfoethyl methacrylate and 2-methacryloyloxyethyl phthalate; styrene derivatives, such as p-styrene sulfonic acid and p-vinylbenzoic acid; and phenol derivatives, such as vinylphenol); allyl compounds, such as sodium allyl sulfonate; acetylene derivatives; polymeric compounds which are obtained by polymerization of monomers, such as trioxane derivatives having negative groups; and copolymers and block copolymers of the above monomers with neutral acrylic and methacrylic esters having a polymerizable functional group (preferably a vinyl group or an acetylene group), such as 2-hydroxyethyl methacrylate, 2-hydroxyethyl acrylate, 1,2-dihydroxyethyl methacrylate, methoxytriethyleneglycol methacrylate, methoxynonaethyleneglycol methacrylate, methyl methacrylate, ethyl methacrylate, methyl acrylate and ethyl acrylate, with neutral monomers, such as styrene and derivatives thereof, and with cationic monomers such as N,N-diethylaminoethyl methacrylate, N,N-dimethylaminoethyl methacrylate, N,N-diethylaminoethyl acrylate and N,N-dimethylaminoethyl acrylate. Among these compounds, particularly preferable are polymeric compounds which are obtained by polymerizing vinyl monomers, because they have a high degree of polymerization, and are easily available.

Among the materials for porous elements of filter media which are subjected to above-mentioned surface modification, particularly preferable are synthetic polyesters, such as polyethylene terephthalate, polybutylene terephthalate and polyoxyethylene terephthalate which have excellent susceptivity with respect to surface modification, such as graft copolymerization and coating.

The specific, limited surface electric charge in the surface portion of the porous element of the filter medium of the present invention can be attained as follows. When a polyester non-woven fabric is desired as a porous element of the filter medium, the porous element having a surface electric charge of not smaller than $-30$ $\mu eq/g$ of the porous element can be obtained by a method in which chips of polyethylene terephthalate are dried with a conventional drier, such as a vacuum drier or a hopper drier, and the dried chips are subjected to melt extrusion-spinning, thereby obtaining the non-woven fabric.

Other methods for attaining a specific, limited surface electric charge of the porous element of the filter medium of the present invention include amidation in which a known carbodiimide, such as dicyclohexylcarbodiimide, is reacted with a compound, such as primary and secondary amines, or a compound having an amino group, and esterification, such as methylesterification by employing diazomethane. Examples of esterification and amidation agents include dicyclohexylcarbodiimide (DCC), diazomethane, dialkyl sulfate and alkyl halide.

The agents are not limited to the above examples. Still other methods for attaining a specific, limited surface electric charge in the surface portion of porous element of the filter medium of the present invention include esterification, in which the porous element is reacted with hydroxyl groups within the element by subjecting it to dehydrating treatment while heating under vacuum; embedding of negative groups into the porous element by contacting with hydrophobic surfaces thereof; and surface modification of the porous element by graft copolymerization which employs a conventional technique, such as radiation and plasma treatment.

It is also possible to attain a specific, limited surface electric charge of the porous element, i.e., in the range of not smaller than $-30$ μeq/g of the element by a method in which the element is coated with a hydrophilic polymer not having a negative charge or a nitrogen-containing positive polymer.

When a filter medium made of a synthetic polyester is heated in a fabrication process, carboxylic groups are produced. The inventors have measured a surface electric charge of commercially available non-woven fabrics which are used as filter media made of polyesters. It has been found that all of the non-woven fabrics have a surface electric charge of smaller than $-30$ μeq/g of the fabric.

In the study by the present inventors, it has been found that when the water content of chips of a synthetic polyester for producing a non-woven fabric to be used for a filter medium is decreased, the surface electric charge of the filter medium can be most effectively increased. More illustratively stated, when the water content of the chips is decreased to 15 ppm or less, preferably 10 ppm or less, the surface electric charge in the range of not smaller than $-30$ μeq/g of the filter medium can be attained.

The greater the surface electric charge of a the filter medium, the smaller the increase in kinin concentration of the treated blood material. However, according to the study of the present inventors, it has been found that with the increase in a surface electric charge of the filter medium, a wettability of the surface of the medium with blood material is decreased, thereby increasing non-specific adsorption of plasma proteins on the surface; that adhesion of platelets to the surface is increased; and that wetting of the surface is not attained easily. When the wettability of a filter medium is expressed as critical wetting surface tension (CWST), the CWST value of the medium is preferably not less than 50 dyn/cm, and most preferably not less than 58 dyn/cm, to attain favorable wetting of the medium.

The wettability of the medium is not determined by only the quantity of the surface electric charge of the filter medium. However, in a conventional filter medium for treating a blood material, especially in a filter medium for use in removing leukocytes, such as a polyester non-woven fabric, carboxylic groups in the non-woven fabric prominently contribute to the wettability. Thus, it is found that when the CWST value of the medium is increased, the quantity of carboxylic groups in the fabric is also increased. The higher the value of CWST, the higher the wettability. However, along with the increase in the CWST value of the medium, an increase in kinin concentration is observed. Thus, in actual use of the filter medium, the CWST value of the medium is preferably not greater than 102 dyn/cm, more preferably not greater than 90 dyn/cm.

However, for example, by causing neutral hydrophilic groups to be retained at or on the surface of the porous element, the CWST value can be increased while keeping a surface electric charge in the range of not smaller than $-30$ μeq/g of the porous element.

The term "CWST" used in the present invention means a value obtained by the following method. A series of aqueous solutions are prepared in varied concentrations, so that the solutions have surface tensions which are serially different by a value of 2 to 4 dyn/cm. The aqueous solutions are separately placed on the porous element in the form of 10 drops, and the drops are allowed to stand for 10 minutes. The aqueous solutions are used in the order of from a low surface tension solution to a high surface tension solution. After the 10 drops have been allowed to stand for 10 minutes, examination is made to determine the number of drops which have been absorbed onto the porous element. When 9 or more of the 10 drops have been absorbed onto the porous element, it is defined as being wetted with the solution. On the other hand, when the number of drops which have been absorbed is less than 9 of the 10 drops, it is defined as being non-wetted with the solution. In this way, the testings are successively conducted using the solutions in the order of from a low surface tension liquid to a high surface tension liquid. A wet state and a non-wet state would appear. In this case, an average value of the highest value of surface tension at which a wet state is observed and the lowest value of surface tension at which a non-wet state is observed, is defined as the CWST value of the porous element.

The hydrophilicity of the surface of a filter medium can be represented by contact angle. When the surface of the medium is contacted with a liquid, the hydrophilicity of the medium can be represented by a contact angle $\theta$. In the present invention, the contact angle $\theta$ is measured as follows. A liquid drop having a surface tension of 100 dyn/cm is caused to fall on the surface of the medium, which is kept horizontal. When the liquid drop does not wet the surface, a tangential line can be drawn to the surface of the drop at a contact point where the liquid drop stays on the surface of the medium, Angle $\theta$ is the angle between the tangential line and the surface of the medium. When the angle $\theta$ is not greater than 120°, wetting is likely to occur between a blood material and the surface of the filter medium during the removal of leukocytes. Moreover, when the hydrophilicity of the medium is high, it is possible to prevent the adsorption of necessary plasma proteins to the surface of the media. When the contact angle is not greater than 90°, preferably 70°, the medium becomes an excellent filter medium for removing leukocytes from blood material.

A zeta-potential is measured by a streaming potential measuring instrument (ZP-10B of Shimadzu Corporation, Japan), wherein a potassium chloride solution having a KCl concentration of $10^{-3}$ mol/l It can be said that, in one aspect, the zeta-potential represents the relationship between the hydrophilicity of the medium and the surface electric charge of the medium. Thus, the value of the zeta-potential depends on the hydrophilicity of the medium. In a filter medium, when the zeta-potential thereof is $-25$ mV or more, a safe filter medium which is not likely to increase bradykinin, is obtained. When the zeta-potential becomes higher due to the negative groups in the medium, the increase in bradykinin concentration becomes lower. Thus, when the zeta-potential is $-20$ mV or more, preferably in the range of from −15 to 0 mV, an excellent filter medium is obtained.

In the present invention, the average pore diameter of the porous element of the filter medium can be obtained by a method which comprises first cutting the porous element in a direction perpendicular to the blood flow direction; secondly, identifying pores having substantially the same size which are most abundant among various pores distributed over the cross-section; and thirdly, obtaining the pore size of the identified most abundant pores in terms of the diameter of a circle having the same area as the cross-sectional area of the identified pores. Illustratively stated, the pores distributed over an arbitrary cross-section of the porous element may have various morphologies with various sizes. With respect to individual pores, respective cross-sectional areas are obtained in terms of respective diameters of circles having the same areas as the respective cross-sectional areas of the pores. When the number of the pores (ordinate) is plotted against the diameter (abscissa) of the corresponding circle, a nearly normal distribution curve is obtained. The average pore diameter used herein is defined as the diameter falling on the peak of the normal distribution curve. As apparent from the above, the average pore diameter represents an average diameter of the circles corresponding to the pores distributed over every arbitrary cross-section, and it is requisite in the present invention that the average pore diameter on any of the cross-sections be in the range of from 1 to 100 $\mu$m.

In the filter medium of the present invention for removing leukocytes from a blood material, the average diameters of an upstream end portion (with respect to the direction in which a blood material is adapted to flow) and a downstream end portion (with respect to the direction in which a blood material is adapted to flow) of the porous element, respectively, mean the average pore diameters on cross-sections at portions having their respective thickness of 0.5 mm or less, as measured from the upstream end surface and from the downstream end surface of the porous element. For the measurement of the average pore diameter, the cross-section is photographed with a scanning electron microscope, and then the diameters of more than 1000 pores distributed on the cross-section, which are randomly selected, are measured with an eye to obtaining the average pore diameter. In order to measure the average pore diameters at the upstream end portion and downstream end portion of the porous element, the surface of the porous element is photographed with a scanning electron microscope. The diameters of pores in the obtained photograph are measured randomly more than 1000 times with the human eye. In this connection, the average pore diameter of the porous element can be measured by subjecting sampled portions each comprising the above-mentioned cross-section and having a thickness of not greater than 0.5 mm to mercury porosimetry (using Poresizer ® 9320 of Shimadzu Corporation, Japan) to be conducted in substantially the same manner as described hereinbefore with respect to the measurement of the porous element.

In the present invention, the surface area of the porous element is the product of the specific surface area (m$^2$/g) of the porous element measured by mercury porosimetry, multiplied by the bulk density (g/cm$^3$ or g/ml) of the porous element. The above measurement by mercury porosimetry is made under substantially the same conditions as employed in actually packing the filter medium in the apparatus for selectively removing leukocytes from a blood material according to the present invention.

With respect to the measurement by mercury porosimetry under a pressure using a mercury porosimeter, the pressure is in the same range of from 1 to 2650 psi as employed in the measurement of the porous element.

The average pore diameter of the porous element of the filter medium of the present invention is preferably in the range of from 1 to 100 $\mu$m, more preferably in the range of from 1 to 50 $\mu$m, most preferably from 1 to 30 $\mu$m, from the viewpoint of desired efficiency in removing leukocytes. When the pore diameter of pores of the porous element of the filter medium varies thicknesswise, the average pore diameter of an upstream end portion (with respect to a direction in which a blood material is adapted to flow) of the porous element is in the range of from 3 to 100 $\mu$m, more preferably from 10 to 80 $\mu$m, most preferably from 10 to 50 $\mu$m. That is, when the average pore diameter is less than 3 $\mu$m, blood cells are likely to cause clogging, thereby increasing pressure loss, during the removal of leukocytes. When the average pore diameter is more than 100 $\mu$m, the contact frequency of the surface of the filter medium with blood cells decrease, thereby decreasing removing efficiency at the surface of the upstream end portion of the porous element of the filter medium, and causing clogging inside the filter medium. The average pore diameter of a downstream end portion (with respect to a direction in which a blood material is adapted to flow) of the porous element is preferably equal to or smaller than that of the upstream end portion, i.e., from 1 to 30 $\mu$m. When the average pore diameter is less than 1 $\mu$m, the passage is too narrow, thereby increasing pressure loss. When the average pore diameter is more than 30 $\mu$m, the quantity of leukocytes removed decreases. Thus, the average diameter is preferably from 2 to 20 $\mu$m, more preferably from 3 to 15 $\mu$m.

The downstream end portion of the porous element of the filter medium has a total pore surface area of preferably 0.20 to 5.70 m$^2$/ml, more preferably 0.50 to 5.70 m$^2$/ml, and most preferably 0.70 to 5.70 m$^2$/ml of the porous element. The sum of the respective pore surface areas of pores having a pore diameter of 1 to 10 $\mu$m is preferably 50% or more, more preferably 55% or more, most preferably 60% or more, based on the total pore surface area of the downstream end portion of the porous element. The sum of respective pore surface areas of pores having a pore diameter of 1 to 30 $\mu$m is preferably 75% or more, more preferably 85% or more, most preferably 90% or more, based on the total pore surface area of the downstream end portion. The sum of respective pore surface areas of pores having a pore diameter of less than 1 $\mu$m is preferably 38% or less, more preferably 30% or less, most preferably 28% or less. When the total pore surface area of the downstream end portion is less than 0.35 m$^2$/ml of the porous element, the total pore surface area is insufficient for effective adhesion of leukocytes, thereby causing a leakage of leukocytes. On the other hand, when the total pore surface area of the downstream end portion exceeds 5.70 m$^2$/ml of the porous element, the time necessary for the treatment of blood is prolonged, and not only leukocytes but also red cells and platelets are likely to be removed, so that the pressure loss is disadvantageously increased due to clogging of the porous element. Further, when the sum of respective pore surface areas of pores having a pore diameter of 1 to 10 $\mu$m and the sum of respective pore surface areas of pores having a pore diameter of 1 to 30 μm are, respectively, less than 50% and less than 60%, based on the total pore surface area of the downstream end portion of the porous element, a leakage of lymphocytes or a clogging of the porous element is likely to occur. Since pores having a pore diameter of less than 1 μm are less likely to allow passage of blood cells therethrough, when the sum of respective pore surface areas of pores having a pore diameter of less than 1 μm is more than 38%, the recovery of red cells and platelets is disadvantageously lowered.

The upstream end portion of the porous element has an average pore diameter which is preferably 2 to 100 times, more preferably 3 to 50 times, most preferably 3 to 25 times the average pore diameter of the downstream end portion of the porous element. When the ratio of the average pore diameter of the upstream end portion to the average pore diameter of the downstream end portion is less than 2, not only is clogging of the porous element with leukocytes likely to occur in the upstream end portion, but also the leukocyte-capturing ratio is decreased. On the other hand, when the ratio of the average pore diameter of the upstream end portion to the average pore diameter of the downstream end portion is more than 100, clogging of the porous element with leukocytes is likely to occur in the downstream end portion, thereby increasing the pressure loss.

The term "total pore volume" used herein means a volume of pores per unit volume of the porous element, and can be measured by subjecting sampled portions, each of which is obtained by cutting the porous element in a direction perpendicular to the flow direction of the blood material and has a thickness of not greater than 0.5 mm, to mercury porosimetry (using Poresizer® 9320 of Shimadzu Corporation, Japan) to be conducted in substantially the same manner as described hereinbefore with respect to the measurement of the average pore diameter, and by plotting the number of the pores (ordinate) against the diameter (abscissa) of the pores. The total pore volume is determined by the number and diameter of the pores.

An upper limit of the total pore volume of the porous element is preferably 0.95 ml/ml from the viewpoint of a desired mechanical strength, and a lower limit is preferably 0.40 ml/ml or more, more preferably 0.45 ml/ml, most preferably 0.50 to 0.95 ml/ml because from the viewpoint of leukocyte-removing efficienty, it is preferred that the porous element have many pores having suitable diameters and having a large contact surface area in total.

As a result of the investigations by the present inventors for developing a filter medium capable of removing leukocytes with high efficiency, it has been found that the filter medium has an average pore diameter and a total pore volume in the respective ranges as specified above, and that the sum of respective pore volumes of pores having a pore diameter of 1 to 100 μm is necessarily to be 75% or more, preferably 85% or more, based on the total pore volume. For removing leukocytes without causing clogging of the porous structure and with high efficiency, such that the leukocyte residual ratio becomes $10^4$ or less, it is preferred that the sum of respective pore volumes of pores having a pore diameter of 1 to 100 μm be 90% or more, based on the total pore volume.

Especially, with respect to the downstream end portion of the porous element, it is preferred that the sum of respective pore volumes of pores having a pore diameter of 1 to 30 μm be 75% or more, preferably 85% or more, based on the total pore volume of the downstream end portion. For removing leukocytes without causing clogging of the porous element and with high efficiency such that the leukocyte residual ratio becomes $10^4$ or less, the sum of respective pore volumes of pores having a pore diameter of 1 to 30 μm is preferably 90% or more, based on the total pore volume of the downstream end portion.

A specific surface area of the porous element is preferably 0.5 to 15 $m^2/g$, more preferably 1 to 15 $m^2/g$ from the viewpoints of desired mechanical strength and desired ability to remove leukocytes, and is most preferably 2 to 15 $m^2/g$, so that the ability to remove leukocytes becomes practically more sufficient.

When a fibrous filter material, such as a knit fabric, a woven fabric or a non-woven fabric, is used as the porous element of the filter medium of the present invention, the diameter of the fibers reflects an average pore size and a pore distribution. Therefore, it is important for the fibers to have an effective average diameter. An average fiber diameter can be determined by a method comprising photographing a surface of a fibrous filter medium with a scanning electron microscope, and visually measuring respective diameters of 100 or more of fibers which are randomly selected from fibers dispersed on a photographed surface. An average fiber diameter of the main or downstream end portion of the porous element, which is an effective portion for maintenance of mechanical strength and for removal of leukocytes, is 0.3 to 10 μm. The average fiber diameter is preferably 0.3 to 5 μm, more preferably 0.3 to 3 μm, since a smaller fiber diameter causes a higher leukocyte-removing ability. Deviation of fiber diameters from the average fiber diameter is preferably narrow, it is necessary to limit, and the deviation within a range of from 20 to 60%, preferably within a range of from 20 to 50%, based on the average fiber diameter. When the deviation is more preferably 20 to 45%, based on the average fiber diameter, a uniform porous element is obtained.

A method for measuring bradykinin concentration of a treated blood material comprises allowing blood to flow through a casing which has an inlet for a blood material and an outlet for a filtrate and has a filter medium packed therein, sampling treated blood material discharged from the outlet, and measuring the concentration of bradykinin in the sampled blood material. However, a large amount of sample blood is necessary for measurement by this method, and it is difficult to evaluate many filter media at once time. Therefore, evaluation of filter media is conducted by the following method called an "in vitro blood test".

In the "in vitro blood test" method, a filter medium (porous element) having a predetermined surface area and having a predetermined surface electric charge, which are measured beforehand, is placed in a 50 ml polycarbonate Erlenmeyer flask, and 5 ml of a blood material heated to 37° C. is added (the blood material is whole blood having a hematocrit value of 40 to 60% and containing 11.1 vol.% of ACD-A, or a solution which is prepared by adding physiological saline containing 11.1 vol.% of ACD-A to a red cell concentrate to thereby adjust the hematocrit value to a range of from 40 to 60%). The resultant mixture is allowed to stand at 37° C. for 5 minutes. By the investigation of the present inventors, it has been found that the solution prepared from the red cell concentrate is likely to undergo an increase in bradykinin concentration. In addition, such a solution is easily available. Therefore, this solution is especially preferred as a sample blood material for evaluating the filter media with respect to the ability to suppress the unfavorable formation of bradykinin.

In this test method, after allowing the above mixture to stand for 5 minutes, tradirol, soy bean trypsin inhibitor, protamine sulfate and disodium ethylenediaminetetreacetate are added as an inhibitor of decomposition of kallikrein and an inhibitor of kininase activity, and the thus obtained mixture is subjected to centrifugation at 4° C. to collect only plasma components. The collected plasma components are frozen, and a concentration of bradykinin in the frozen plasma components is measured by conventional radioimmunoassay (PEG precipitation method). As a negative control, a bradykinin concentration is measured by the same "in vitro blood test" method as used above except that a filter medium is not placed in the polycarbonate Erlenmeyer flask. The obtained data is used for comparison with the bradykinin concentration of the blood material measured using the filter medium. Furthermore, as a positive control, a bradykinin concentration is measured by the same "in vitro blood test" method as used above, except that a glass Erlenmeyer flask is used in place of the polycarbonate Erlenmeyer flask and that a filter medium is not placed in the glass flask.

This form of the filter medium of the present invention is packed in a casing having an inlet for a blood material and an outlet for a filtrate, and can be used as an apparatus for removing leukocytes.

That is, in another aspect of the present invention, there is provided an apparatus for selectively separating leukocytes from a leukocyte-containing suspension, comprising: a casing having an inlet side and an outlet side, the inlet side having an inlet for a leukocyte-containing suspension selected from the group consisting of whole blood, a leukocyte-containing red cell product, a leukocyte-containing platelet product, and a leukocyte-containing plasma product, and the outlet side having an outlet for a filtrate; and a main filter medium packed in the casing at a packing density of from 0.05 to 0.5 g/cm$^3$, the main filter medium comprising a polymeric, porous element having, in a surface portion thereof, a negative charge and having a surface electric charge of not smaller than $-30$ μeq/g of the polymeric, porous element, wherein the polymeric, porous element has an average pore diameter of from 1 to 100 μm and a total pore volume of from 0.4 to 0.95 ml/ml of the polymeric, porous element, and wherein the sum of respective pore volumes of pores of the polymeric, porous element which have a pore diameter of from 1 to 100 μm is 75% or more, based on the total pore volume.

With respect to packing of the filter medium of the present invention in the casing, the filter medium may be packed alone, or the filter medium (as a main filter medium) may be packed together with a preliminary filter medium in the casing. The filter medium to be packed in the casing may have an average pore diameter gradient such that the average pore diameter is substantially continuously or stepwise decreased in a direction from the inlet side to the outlet side (along the direction of flow of blood material).

The morphology of the casing is not specifically restricted, as long as the casing has an inlet for a blood material and an outlet for a filtrate. Preferred examples of morphologies of casings include a morphology of casing in which filter media can be packed in a laminated form; a pillar morphology, such as a circular cylinder, trigonal pillar, square pillar, hexagonal pillar, octagonal pillar and the like; a morphology of casing such that the filter medium (fabric) is wound into a roll having a hollow at a central portion thereof can be packed in a cylindrical casing having an inlet and an outlet at both ends thereof, and the blood material can flow from the periphery of the fabric roll toward the central hollow and the treated blood material is collected at an outlet communicating with the central hollow. Further, a casing having a cross-sectional area gradually decreased in the direction of flow from the inlet side to the outlet side, can also be used.

The casing preferably has a quotient (S/L) of a cross-sectional area divided by a vertical length in a range of from 10 to 500 cm.

The packing density of the filter medium in the casing means the weight of the filter medium per unit volume. A leukocyte-removing apparatus is prepared by packing the filter medium in a casing at the packing density of 0.05 to 0.5 g/cm$^3$. To allow blood to flow smoothly without clogging of the filter medium and without an increase in the inner pressure of the apparatus, the packing density is preferably from 0.1 to 0.4 g/cm$^3$, more preferably from 0.1 to 0.3 g/cm$^3$.

The cross-sectional area of the leukocyte-removing apparatus is not specifically restricted, but is preferably from 0.5 to 300 cm$^2$ for facilitating production of the apparatus and from the viewpoint of having suitable capacity for blood to be treated. The horizontal cross-sectional area of the casing is more preferably from 0.5 to 250 cm$^2$, most preferably from 0.5 to 200 cm$^2$, from the viewpoints of miniaturization and ease of operation of the apparatus. The thickness of the entire filter medium depends on the morphology thereof, but is preferably from 0.1 to 500 mm. The thickness is more preferably from 0.1 to 450 mm, most preferably from 0.1 to 400 mm from the viewpoint of the desired priming characteristics.

The leukocyte-removing apparatus of the present invention comprises a casing having an inlet side and an outlet side, and a main filter medium having an average pore diameter of 1 to 100 μm which is packed in part or the entire capacity of the casing. The main filter medium (porous element) has a pore diameter distribution such that the average pore diameter has an average pore diameter gradient such that the average pore diameter is substantially continuously or stepwise decreased in the direction from the inlet side (upstream portion of the main filter medium) to the outlet side (downstream portion of the main filter medium), and a pore surface area distribution such that the total pore surface area of the downstream end portion (outlet portion) of the filter medium is within the range of 0.35 to 5.70 m$^2$/ml wherein the sum of respective pore surface areas of pores having a pore diameter of 1 to 10 μm and the sum of respective pore surface areas of pores having a pore diameter of 1 to 30 μm are, respectively, 50% or more and 60% or more, based on the total pore surface area of the downstream end portion.

The filter medium of the leukocyte-removing apparatus of the present invention also has a pore surface area distribution such that the sum of respective pore surface areas of pores having a pore diameter of less than 1 μm is preferably 38% or less.

In the leukocyte-removing apparatus of the present invention, it is preferred that the upstream end portion (inlet portion) of the main filter medium have an average pore diameter of 3 to 100 μm whereas the downstream end portion (outlet portion) of the main filter medium have an average pore diameter of 1 to 30 μm.

Further, it is preferred that the upstream end portion of the main filter medium have an average pore diameter 2 to 100 times the average pore diameter of the downstream end portion of the main filter medium.

In the leukocyte-removing apparatus of the present invention, the term "substantially continuously decrease" used herein with respect to the average pore diameter of the filter medium means that the pore diameters of the filter medium (porous element) are gradually decreased from an upstream end portion to a downstream end portion in a flow direction in which the blood material to be treated for removing leukocytes is adapted to be flowed. On the other hand, the term "stepwise decrease" used herein means that in the filter medium, there are thicknesswise extending portions, each of which contains pores having substantially the same average pore diameter, and the pore diameters of the filter medium are stepwise decreased from an upstream end portion to a downstream end portion in the flow direction in which a blood material to be treated for removing leukocytes is adapted to be flowed.

An average pore diameter of the upstream end portion of the filter medium in the leukocyte-removing apparatus of the invention is preferably 3 to 100 μm, whereas an average pore diameter of the downstream end portion of the filter medium of the leukocyte-removing apparatus is preferably 1 to 30 μm. When the average pore diameter of the upstream end portion is less than 3 μm, the filter medium is likely to suffer from clogging with blood cells during the leukocyte-removing filtration. On the other hand, when the average pore diameter of the downstream end portion exceeds 30 μm, leukocytes are likely to leak through the filter medium. Preferred average pore diameters of the upstream end portion and the downstream end portion are from 10 to 80 μm and from 2 to 20 μm, respectively, more preferably from 10 to 50 μm and from 3 to 15 μm, respectively, from the viewpoint of the desired performance of the apparatus.

Especially when the filter medium used in the leukocyte-removing apparatus is of the fibrous type, such as a non-woven fabric type, preferred average fiber diameters of such a fibrous filter medium at an upstream portion thereof and at a downstream portion thereof are from 1.5 to 3.0 μm and from 0.3 to 1.9 μm, respectively.

When the apparatus of the present invention is used for treating a blood material not immediately after blood-collecting, e.g. 1 hour after blood-collecting, microaggregates and the like are produced and are likely to cause clogging of the filter medium. For preventing such clogging, a preliminary filter medium is advantageously used together with main filter medium in the leukocyte-removing apparatus. Such a preliminary filter medium may be of a fibrous material type or a porous article type. When the preliminary filter medium is used together with the main fibrous filter medium in the apparatus, it is preferred that the main filter medium have an average fiber diameter of from 1.5 to 1.8 μm at an inlet portion thereof and an average fiber diameter of from 0.5 to 1.7 μm at an outlet portion thereof, whereas the preliminary filter positioned upstream of the main filter medium in the apparatus has an average fiber diameter of from 5 μm to 1 mm. Generally, it is preferred that the preliminary filter medium have an average pore diameter of from 100 to 400 μm, wherein the sum of respective pore volumes of pores of the preliminary porous element which have a pore diameter of from 100 to 400 μm is 30% or more, based on a total pore volume of the preliminary porous element.

The priming volume of the leukocyte-removing apparatus of the present invention is not specifically restricted, but is preferred to be small in view of controllability and of shortening of time duration for removal of leukocytes by the apparatus. Examples of the priming volume include preferably 0.5 to 300 ml, more preferably 1 to 250 ml, most preferably 5 to 250 ml.

The leukocyte-removing apparatus can be sterilized by any conventional method, e.g. a thermal sterilization method in Which an autoclave or the like is used, a chemical sterilization method in which ethylene oxide gas (EOG) is used, a radiation sterilization method in which gamma rays, electron rays or UV rays are used, or the like.

The leukocyte-removing apparatus can be employed in a system for extracorporeal circulation or transfusion. Such a system comprises the apparatus of the present invention and, disposed upstream or downstream of the apparatus, a blood bag, a blood circuit, a blood chamber, a clamp, a roller clamp, a drip chamber, a needle, a drip chamber having a mesh, a tube for a blood pump, and the like, wherein they are used individually or in combination. The components of the system are not restricted to the above examples. A blood pump, a fluid feed pump, a suction pump and/or the like can be used in a circuit of the system. The blood material may be circulated in the system by gravity of the blood per se.

The leukocyte-removing apparatus can be used in an extracorporeal circulation for removing leukocytes from the blood of patients autoimmune diseases, such as systemic lupus erythematosus, multiple sclerosis, rheumatoid arthritis and the like; blood or a patient of leukemia, cancer or the like; or blood to be circulated to a patient to which a drug has been administered for lowering the immune function before organ transplantation. The apparatus can also be used for removing leukocytes from blood to be circulated to a patient after being subjected to a surgical operation; for removing broken bone pieces and the like from blood recovered during a cardiac surgical operation; and for preventing pieces of an adsorbent material from being circulated to a patient by an extracorporeal circulation.

The apparatus containing the filter medium of the present invention can reduce a leukocyte residual ratio in the treated blood material to a level as low as $10^4$ or less.

A method for removing leukocytes by the filter medium of the present invention or the apparatus containing the medium packed therein is described below.

The leukocyte-removing method comprises allowing a blood material, to be treated, to flow at a flow rate of from 1 to 100 ml/min, wherein the linear velocity is from 0.05 to 15 cm/min. The lower the linear velocity, the higher the leukocyte-removing ability, however, a prolonged period of time is needed for blood treatment. Therefore, the flow rate is preferably from 1 to 80 ml/min in practice, and the linear velocity is preferably from 0.1 to 10 cm/min. Under these flow conditions, a high ability for removing leukocytes is exhibited.

The blood material may flow either continuously or intermittently through the filter medium or the leukocyte-removing apparatus, arbitrarily or according to the arrangement of a system containing the filter medium or leukocyte-removing apparatus. When the blood material is retained in the leukocyte-removing apparatus for a long time, bradykinin is activated. For obtaining a higher ability to remove leukocytes, it is preferred that the retention time of the blood material be long. When the retention time is 10 seconds or more, the method of the present invention especially exhibits an excellent effect. However, when the blood material is retained in the leukocyte-removing apparatus for too long a time, nonspecific adsorption of blood components and/or coagulation of blood is likely to occur. Therefore, the retention time is preferably not longer than 30 minutes. The retention time is more preferably 1 minute or more, and still more preferably 10 minutes or more.

Bradykinin is gradually decomposed by a kininase, such as angiotensin converting enzyme. When blood material is injected in a human body a relatively long period of time after treatment by the leukocyte-removing apparatus, the increase of bradykinin is very small and no bradykinin problem occurs. Advantageous effects of the present invention are exerted when blood material is injected into a human body soon, e.g. within 1 hour after treatment by the leukocyte-removing apparatus. More advantageous effects are exerted when the blood material is injected within 30 minutes after treatment. When the blood material is injected within 10 minutes after treatment by the leukocyte-removing apparatus, still more advantageous effects are obtained. In practice, most advantageous effects are exerted when the leukocyte-removing apparatus is employed in an extracorporeal circulation.

The method for removing leukocytes can be practiced for removing leukocytes from fresh whole blood, blood products, such as fresh platelet concentrates, preserved blood materials, and the like, using the leukocyte-removing apparatus of the present invention.

Examples of blood products include concentrated red cells (CRC) having thereto an anticoagulant of the citrate type (such as ACD-A, ACD-B, ACD-C or CPD), or CRC having added thereto mannitol-adenine-phosphate (MAP), saline-adenine-glucose-mannitol (SAGM) or ADSOL as a reagent for preserving platelet concentrate and for red cells. The leukocyte-removing method can be used for removing leukocytes from the blood products without causing an increase in bradykinin concentration of the blood products. Furthermore, using the leukocyte-removing apparatus of the present invention, leukocytes can be removed from blood to be subjected to extracorporeal circulation without causing an increase in bradykinin concentration of blood.

Anticoagulants which can be used in the leukocyte-removing method of the present invention are not specifically restricted. Examples of anticoagulants include ACD-A (acid citrate dextrose-A), CPD (citrate phosphate dextrose), ethylenediaminetetramine-tetraacetic acid (EDTA), heparin, MAP, nafamostat mesilate and the like. Of these coagulants, ACD-A, CPD and heparin are preferred, and ACD-A and CPD are more preferred. When ACD-A or CPD is used in the method of the present invention, leukocytes can be removed from a blood material without causing an increase in bradykinin concentration of the blood material. Even when blood contains an angiotensin converting enzyme inhibitor (ACE-inhibitor), such as captopril, leukocytes can be removed without causing an increase in bradykinin concentration of the blood material. The most preferable effect is exhibited especially when a blood material containing nafamostat mesilate as an anticoagulant or a blood material not containing an ACE-inhibitor is treated by the leukocyte-removing apparatus of the present invention. In the method of removing leukocytes from a blood material of the present invention, leukocytes can be removed from the blood material while suppressing or controlling the bradykinin concentration of the blood material to a level not exceeding 4,000 pg/ml.

In another form of the filter medium of the present invention, the filter medium used in separating whole blood into a blood cell product and plasma, or in separating whole blood or plasma, each containing at least one preselected substance, into the at least one preselected substance and the remaining whole blood or plasma product substantially free of the at least one preselected substance. The filter medium comprises a polymeric, porous element having, in a surface portion thereof, a negative charge and having a surface electric charge of not smaller than $-30$ μeq/g of the polymeric, porous element, wherein the polymeric, porous element is a porous membrane having an average pore diameter of from 10 Å to 1.0 μm and having a water permeability of from 3.4 to 8,000 ml/hr/m$^2$/mmHg.

There are various types of membrane filter media having various quantities of negative charges in their surface portions. The present inventors have conducted measurements of the quantities of negative charges in their surface portions, and found that all of the measured conventional hollow fiber porous membranes and flat porous membranes, which are made mainly of polyacrylonitrile, cellulose, polymethylmethacrylate or the like, have a negative charge of greater than $-50$ μeq/g (namely, for example, $-53$ μeq/g, $-55$ μeq/g or so), since a negative charge has been intentionally introduced to their surface portions for improving the wettability of the membrane to blood.

A porous membrane having a negative charge in a surface portion thereof of greater than $-50$ μeq/g of the medium causes the problem that the quantity of bradykinin is largely increased in the surface portion thereof. As mentioned above, it has been found that with respect to the kinin problem, the higher the surface electric charge of the membrane, the better the removal of the kinin problem. Furthermore, a porous membrane having a positive charge at or on the portion thereof in a large amount causes no problem with respect to the increase of kinin.

However, as a result of the investigations by the present inventors, it has been found that it is not necessarily advantageous to completely remove the negative functional groups present at or on the surface portion of a porous membrane, because in practical use the presence of negative functional groups is important in improving the wettability of the surface of the porous membrane to blood. It is especially important to increase the electric charge in the surface portion of the porous membrane without reducing the hydrophilicity thereof.

That is, a porous membrane which has a surface electric charge of not smaller than $-30$ μeq/g of the membrane is excellent and particularly preferred from the viewpoint of the kinin problem as well as wettability to blood.

Examples of materials to be used for preparing the membrane type filter medium of the present invention include polyacrylonitrile; cellulose; cellulose acetate; polysulfone; polyvinyl alcohol; copolymers of vinyl alcohol and ethylene; cuprammonium regenerated cellulose; polyesters, such as polyethylene terephthalate, polybutylene terephthalate and polyoxyethylene terephthalate; polyamides, such as nylon 6 and nylon 6, 6; aromatic polyamide; polystyrene and derivatives thereof; polyolefin, such as polyethylene, polypropylene and polybutene; polymeric compounds which are obtained by polymerization of methacrylate derivatives, such as methyl methacrylate and ethyl methacrylate; polymeric compounds which are obtained by polymerization of acrylate derivatives, such as methyl acrylate and ethyl acrylate; polymeric compounds such as polytrifluorochloroethylene, polyvinyl formal, polyurethane, polyvinyl acetal and polycarbonate; a homopolymer, copolymer, or block copolymer of the above-mentioned polymeric compound, a blend thereof, or an alloyed product thereof; regenerated cellulose and/or a cellulose derivative; regenerated fibers; or a blend or alloyed product of regenerated fibers with the above-mentioned synthetic, polymeric compound.

Of the above-mentioned materials, particularly preferred are a polymeric compound made mainly of polyacrylonitrile; a homopolymer or copolymer which is obtained by polymerization of methacrylate derivatives, such as methyl methacrylate and ethyl methacrylate; and a polymeric compound made mainly of regenerated cellulose and/or a cellulose derivative, from the viewpoint of fabricatability into a porous membrane and the sharpness of the pore distribution of the resultant porous membrane.

The surface of the membrane type filter medium comprising the above-mentioned material can be modified with a compound having a low or high molecular weight by conventional techniques, such as covalent bonding, ionic bonding, radiation-graft polymerization or plasma treatment, physical adsorption, embedding or precipitation immobilization. For example, there is known a conventional method in which the surface of the filter medium is modified by conventional techniques, such as graft polymerization of polymeric compounds or monomers thereof by radiation or plasma treatment, or covalent bonding (Japanese Patent Application Laid-Open Specification Nos. 1-249063 and 3-502094). Examples of monomers and polymeric compounds for use in surface modification of the membrane type filter medium include vinyl monomers (for example, methacrylic acid; acrylic acid; acrylic acid or methacrylic acid derivatives such as 2-methacryloyloxyethyl succinate, mono (2-acryloyloxyethyl) acid phosphate, 2-sulfoethyl methacrylate and 2-methacryloyloxyethyl phthalate; styrene derivatives, such as p-styrene sulfonic acid and p-vinylbenzoic acid; and phenol derivatives such as vinylphenol); allyl compounds, such as sodium allyl sulfonate; acetylene derivatives; polymeric compounds which are obtained by polymerization of monomers, such as trioxane derivatives having negative groups; and copolymers and block copolymers of the above monomers with acrylic and methacrylic esters having a polymerizable functional group (preferably a vinyl group or an acetylene group), such as 2-hydroxyethyl methacrylate, 2-hydroxyethyl acrylate, 1,2-dihydroxyethyl methacrylate, methoxytriethyleneglycol methacrylate, methoxynonaethyleneglycol methacrylate, methyl methacrylate, ethyl methacrylate, methyl acrylate and ethyl acrylate, with neutral monomers, such as styrene and derivatives thereof, and with cationic monomers such as N,N-diethylaminoethyl methacrylate, N,N-dimethylaminoethyl methacrylate, N,N-diethylaminoethyl acrylate and N,N-dimethylaminoethyl acrylate. Of these compounds, polymeric compounds obtained by polymerization of vinyl monomers are particularly preferable, because they have a high degree of polymerization, and are easily available.

The negative charge in the surface portion of the membrane type filter medium of the present invention can be reduced by using, for example, an acrylonitrile copolymer containing no electric charge as a raw material in the preparation of a porous membrane. Such a raw material gives a desirable hollow fiber porous membrane or flat porous membrane.

Other methods for increasing the surface electric charge of the membrane type filter medium of the present invention include amidation, in which a known carbodiimide, such as dicyclohexylcarbodiimide, is reacted with a compound, such as primary and secondary amines or a compound having an amino group, and esterification, such as methylesterification by employing diazomethane. Still other methods for increasing a surface electric charge of the membrane type filter medium of the present invention include esterification in which the medium is reacted with hydroxyl groups within the medium by subjecting to dehydrating treatment while heating under vacuum; embedding of negative groups into the medium by contacting with hydrophobic surfaces thereof.

Still other method includes surface modification of the medium by graft copolymerization which employs a conventional technique such as radiation and plasma treatment. It is also possible to increase a surface electric charge of the medium by forming, on the surface thereof, a coating layer comprising a compound having no positive or negative functional groups, and having a hydrophilic partial structure such as polyethylene glycol chain, or a hydrophilic compound having positive groups.

The zeta-potential of a flat porous membrane is measured by a streaming potential measuring instrument (ZP-10B of Shimadzu Corporation, Japan).

The zeta-potential of a hollow porous fiber is measured as follows. First, one filament of the hollow porous fiber is cut into a piece 14 cm in length to thereby obtain a sample. A platinum electrode is attached to both ends thereof, and then the fiber sample is connected through a tube to a bottle containing a potassium chloride solution having a KCl concentration of $10^{-3}$ mol/liter. To this bottle, a pressure is applied up to 0.5 kg/cm$^3$, so that the KCl solution can pass through the hollow fiber. The streaming potential is measured, while increasing the pressure. Then, the zeta-potential is determined by the following formula.

Zeta-potential (mV) = $1.44 \times 10^3 \times$ streaming potential $\times$ electric conductivity/pressure Since a negative charge in the inside of a hollow porous fiber is likely to be a causative of an increase in kinin concentration in the blood material, the above-mentioned measuring method is preferable to the other method in which the entire portion of a filter medium is subjected to measurement. The zeta-potential takes a different value if the shape of surface, weight, etc. of a sample is different. Therefore, the zeta-potential of a hollow fiber porous membrane and that of other filter medium cannot be evaluated uniformly.

It can be said that in one aspect, the zeta-potential represents the relationship between a hydrophilicity of the medium and a surface electric charge of the medium. Thus, the value of the zeta-potential depends on the hydrophilicity of the medium. In a hollow fiber porous membrane, when its zeta-potential is −2 mV or more, it can be a safe filter medium free of the bradykinin problem. When the zeta-potential becomes higher due to negative groups in the medium, the increase of bradykinin becomes smaller. Thus, the zeta potential of a hollow fiber porous membrane is preferably from −1 mV or more, more preferably from −0.5 to 0 mV.

The higher the surface electric charge of the filter medium, the better the removal of the kinin problem. However, according to the study of the present inventors, it has been found that with the increase of the surface electric charge of a filter medium, the wettability of the surface of the medium is decreased to thereby increase non-specific adsorption of plasma proteins on the surface; that adhesion of platelets to the surface is increased; and that wetting of the surface is not attained easily. When the wettability of a filter medium is expressed in terms of a critical wetting surface tension (CWST), the CWST value of the membrane type filter medium is preferably 20 dyn/cm or more, more preferably 50 dyn/cm or more to attain favorable wetting of the medium.

The wettability of the medium is not determined by only the quantity of negative functional groups on the surface thereof. However, in conventional porous membranes for treating blood material, comprising a polyacrylamide or the like, sulfonic acid groups or carboxyl groups in the pores prominently contribute to wettability. The higher the value of CWST, the higher the wettability. However, along with the increase of a CWST value of the medium, an increase of kinin is observed. Thus, in actual use of a membrane type filter medium, the CWST value of the medium is preferably not greater than 102 dyn/cm, more preferably not greater than 90 dyn/cm.

However, for example, by introducing neutral hydrophilic groups in the surface of a porous membrane, the CWST value can be increased while keeping the surface electric charge not smaller than −30 μeq/g of the porous membrane.

The CWST value can be measured in the same manner as described hereinbefore in connection with the leukocyte-removing filter medium. With respect to a hollow fiber porous membrane, however, prior to the measurement, a flat hollow porous fiber assembly is formed by a method in which a plurality of hollow porous fibers are arranged and placed in parallel on a flat plate, such as a slide glass, without leaving any space between the hollow porous fibers, and their respective both ends are fixed onto the plate with a silicone adhesive or the like.

The average pore diameter of the membrane type filter medium of the present invention is determined by subjecting the filter medium to scanning electron photomicrography, followed by randomly selecting 1000 or more of the pores scattering on the photomicrograph and measuring their diameters visually. Although a suitable average pore diameter of the membrane type filter medium varies depending on its use, it is preferably from 10 Å to 1 μm, more preferably from 10 Å to 0.5 μm. In the case of a filtration type dialysis membrane, good filtration can be obtained when its average pore diameter is from 15 to 20 Å. The range of pore diameters, the thickness of the porous membrane, and the inner and outer diameters of the hollow porous fiber are also measured visually using photomicrographs in substantially the same manner as mentioned above. It is preferred that the pore diameter be in the range from 30 to 400 Å. With respect to a hollow fiber porous membrane, it is preferred that the inner and outer diameters of the hollow fiber and the thickness of the porous membrane be as small as possible, so that a greater number of the hollow porous fibers can be contained in a unit volume of a casing, providing a large porous membrane area. However, from the viewpoint of a desired mechanical strength of the porous membrane, it is preferred that the thickness of the porous membrane be from 5 to 200 μm, the inner diameter of the hollow porous fiber from 50 to 300 μm, and the outer diameter of the hollow porous fiber from 100 to 1,000 μm.

The porosity (% by volume) of the membrane type filter medium of the present invention can be obtained from the following formula.

$$\text{Porosity (\% by volume)} = \frac{\dfrac{\text{Dry weight of the porous membrane}}{\text{Specific gravity of the porous membrane}}}{\dfrac{\text{Dry weight of the membrane having no pores}}{\text{Specific gravity of the membrane having no pores}}} \times 100$$

From the viewpoint of desired filtration efficiency, it is preferred that a porosity (% by volume) of the porous membrane be high. However, the porosity (% by volume) is preferably from 30 to 75% from the viewpoint of mechanical strength of the porous membrane, more preferably from 40 to 75% from the viewpoint of mechanical strength as well as filtration efficiency.

The water permeability of the hollow fiber porous membrane of the present invention is defined as the amount of water which has passed through a unit area of the porous membrane from the inside to the outside thereof per unit time under a specific pressure. Although a desirable water permeability varies depending on the use of a porous membrane, it is preferred that this value be from 3.4 to 10,000 ml/hr/m$^2$/mmHg, more preferably from 3.4 to 8,000 ml/hr/m$^2$/mmHg. Of these membranes, a membrane exhibiting a high water permeability can be advantageously employed in an artificial dialyzer, etc., by virtue of the high water permeability.

This form of the filter medium of the present invention, i.e., the membrane type filter medium, is packed in a casing having an inlet for blood material and an outlet for a filtrate, and can be used as an apparatus for separating whole blood into a blood cell product and plasma, or for removing a predetermined substance, e.g. an undesired substance from whole blood or plasma.

In still another aspect of the present invention, there is provided an apparatus for separating whole blood into a blood cell product and plasma or for separating whole blood or plasma, each containing at least one preselected substance, into the at least one preselected substance and a remaining whole blood or plasma product substantially free of the at least one preselected substance, comprising: a casing having an inlet for whole blood or plasma and an outlet for a filtrate; and a filter medium packed in the casing, the filter medium comprising a polymeric, porous element having, in a surface portion thereof, a negative charge and a surface electric charge of not smaller than $-30$ µeq/g of the polymeric, porous element, and wherein the polymeric, porous element is a porous membrane having an average pore diameter of from 10 Å to 1.0 µm and having a water permeability of from 3.4 to 8,000 ml/hr/m²/mmHg.

The morphology of a casing in which the membrane type filter medium of the present invention is to be packed is not particularly limited. A casing of any morphology can be used, as long as the casing has an inlet for whole blood or plasma and an outlet for a filtrate, or an inlet and outlet for blood and a dialyzate intake and exit. Examples of casings include a conventional casing in which a flat porous membrane can be packed in laminated form, a circular, triangular, quadrangular, hexangular or octangular column, to which predetermined portions of a hollow fiber porous membrane can be fixed, and a casing in which a hollow fiber porous membrane is fixed only at its blood inlet and outlet in a state such that both openings and inside hollow space of the hollow porous fiber are maintained.

Alternatively, the cone type casing having a cross-sectional area gradually reduced in a direction from a blood inlet to outlet, can be used.

With respect to the cross-sectional area and length of the casing, it is preferred that the casing have a quotient of a horizontal sectional area divided by a vertical length in a range of from 2.5 to 60 cm.

The length of a casing for the membrane type filter apparatus of the present invention is not particularly limited. However, the length is preferably from 15 to 35 cm from the viewpoint of ease in manufacturing as well as ease in handling blood to be treated.

In view of the above-mentioned length of the casing, the effective length of a hollow porous fiber to be packed therein is preferably from 10 to 30 cm.

The priming of the membrane type filter apparatus of the present invention is preferable from the viewpoint of reducing the time required before the start of the operation, as well as rendering the operation easy. It is preferred that the priming volume be from 10 ml to 4 liters, although this varies depending on the shape, size and use of the apparatus.

When the membrane type filter apparatus of the present invention is actually used, there can be provided, upstream or downstream of the filter apparatus, an extracorporeal blood circulation system or a blood transfusion line comprising at least one of the following elements: a blood bag, a blood circuit, a chamber, a clamp, a roller clamp, a drip chamber, a needle, a drip chamber provided with mesh, a tube for a blood pump, etc.

Further, treatment of a blood material with the filter apparatus can be conducted by incorporating a blood pump, liquid feed pump, or suction pump, in some portion of the blood circulation system or transfusion line. Alternatively, the filter apparatus can be operated well in a manner such that blood material is caused to drip by the action of gravity.

The membrane type filter medium of the present invention packed in a casing can be used for haemodialysis, filtration dialysis, separation of whole blood into plasma and a blood cell product, double filtration, concentration of a body fluid, e.g. a serous fluid from an abdominal dropsy patient, push and pull blood filtration, etc.

In still another form of the filter medium of the present invention, the filter medium is used in separating whole blood or plasma, each containing at least one preselected substance, into the at least one preselected substance and a remaining whole blood or plasma product substantially free of the at least one preselected substance by adsorption-filtration. The filter medium comprises a polymeric, porous element having, in a surface portion thereof, a negative charge and having a surface electric charge of not smaller than $-30$ µeq/g of the polymeric, porous element, wherein the polymeric, porous element (which is substantially water-insoluble) is an adsorptive composite comprising a polymeric, porous substrate having, on a surface thereof including pore surfaces, functional groups capable of selectively binding the at least one preselected substance thereto, and the polymeric, porous substrate has an average pore size of from 50,000 to 10,000,000 in terms of an exclusion limit molecular weight.

With respect to a polymeric, porous element for use in removing a preselected substance, such as an undesired substance, from whole blood or plasma by adsorption-filtration, such a porous element has a large number of extremely small micropores which do not allow the entrance of blood coagulation factor XII or the like and, hence, the surface area of the porous element contains a large portion which is inherently not causative of an increase in bradykinin concentration of whole blood or plasma. Therefore, with respect to the porous element for use in removing a preselected substance by adsorption-filtration, it is important to control the quantity of negative charges present on surfaces which are capable of being reached by, and bound to, a triple complex comprised of blood coagulation factor XII (having a molecular weight of about 100,000), kallikrein (having a molecular weight of about 100,000) and high molecular weight kininogen (having a molecular weight of about 70,000). In other words, it is important to control the quantity of negative charges present on the pore surfaces of pores which a compound having a molecular weight of about 300,000 can enter. However, determination and control of the quantity of negative charges on the surfaces of such specific pores is difficult.

The present inventors have made intensive studies and, as a result, they have found that when the surface electric charge of the polymeric, porous element of the filter medium for use in adsorption-filtration is smaller than $-50$ µeq/g of the polymeric, porous element, the bradykinin concentration of blood material is markedly increased upon contact with the porous element. On the other hand, when the above-mentioned surface electric charge is not smaller than $-50$ µeq/g of the porous element, the increase in bradykinin concentration of the blood material is considerably reduced. It has also been found that when the surface electric charge is rendered not smaller than $-30$ µeq/g of the porous element, the increase in bradykinin concentration of the blood material upon contact with the porous element is suppressed to the level which has substantially no adverse effect, such as anaphylactic reactions, on a recipient of the treated blood material.

In this third form of the filter medium of the present invention for use in adsorption-filtration (hereinafter frequently referred to as "adsorptive filter medium"), it is necessary that the weight of the porous element be expressed in terms of the weight determined with respect to the porous element, which is in substantially the same swollen state as during actual use thereof. In the adsorptive filter medium, the porous element is very large in surface area which can be contacted with a preselected substance to be removed by adsorption-filtration, but also exhibits high swelling, so that the surface area per unit weight of the porous element in a dry state is largely different from that of the porous element in a swollen state suitable for actual use. Accordingly, the surface electric charge density of the porous element, which is a most important factor for suppressing the increase in bradykinin concentration of blood material, is largely different between in the dry state and the swollen state. In this connection, the present inventors have found that, with respect to the adsorptive filter medium, the surface electric charge per unit weight of the porous element in a swollen state suitable for actual use has a close correlation with the increase in bradykinin concentration of the treated blood material. The term "swollen state suitable for actual use" means a state in which the adsorptive porous element is saturated with a liquid having substantially the same pH value and osmotic pressure as those of whole blood or plasma. Thus, this term means a state in which the porous element is saturated with physiological saline having a pH of 6.5 to 7.5 and an osmotic pressure of about 280 mOsm.

The weight of the adsorptive filter medium (porous element) is defined as a weight as measured with respect to the porous element which has been allowed to swell and has been packed into a casing.

The weight of the porous element can be measured by a method in which the porous element is allowed to swell with the above-mentioned physiological saline and packed in a casing having an inlet and an outlet and having, at the outlet, a means (such as a mesh) for preventing leaking of the porous element; the saline is flowed through the casing from the inlet to the outlet at substantially the same linear velocity as the velocity at which whole blood or plasma flows in actual use thereof; the volume of the porous element is measured; and the weight of the porous element is determined from the measured volume (assuming that the specific gravity of the swollen porous element is nearly 1.0). When the porous element is in the form of beads or chips, these beads or chips as such are subjected to weight measurement by the above method. When the porous element is in the form of a sheet or a fibrous material, such as a hollow or non-hollow fiber, the weight is determined by the above method after the porous element is cut into short pieces.

In the adsorptive filter medium of the present invention, when the porous element has a positive charge in addition to a negative charge, the surface electric charge of the porous element means a balance (difference) between the negative electric charge and the positive electric charge, which are copresent in the surface of the porous element, which can be contacted with whole blood or plasma to be filtered.

The substrate may have a coating having high affinity to a blood material. Such a coating formed on the substrate is regarded as a part of the substrate.

The terms "positive charge" and "negative charge" mean, respectively, the total of functional and non-functional groups exhibiting a positive charge under neutral conditions (pH 7.0) and the total of functional and non-functional groups exhibiting a negative charge under neutral pH conditions. Each of these positive functional and non-functional groups and negative functional and non-functional groups is in a dissociated state under neutral pH conditions.

Some substrates, such as activated carbon, inherently have functional groups at or on surfaces thereof. Such substrates (inherently having functional groups) as such can be used as the adsorptive composite of the present invention. However, it is generally preferred that the substrate have a functional group-containing ligand introduced to a surface thereof.

When the substrate has a ligand, at least one of the substrate and the ligand has a negative charge.

When the ligand exhibits a negative charge, it is preferred that the substrate exhibit a positive charge. On the other hand, when the ligand exhibits a positive charge, it is preferred that the substrate exhibit a negative charge. Further, each of the substrate and the ligand may have both positive and negative charges.

In those adsorptive filter media which have, bonded to a surface thereof, a ligand containing functional groups, the capability to prevent an increase in bradykinin concentration of a treated blood material is greatly influenced by the electrostatic characteristics of the ligand and the substrate surface.

When a ligand contains negative functional groups and exhibits a negative charge (such a ligand is hereinafter frequently referred to as a "negative ligand"), it can electrostatically bind a preselected substance thereto by virtue of the negative functional groups. In this case, the larger the quantity of the negative ligand or the larger the negative charge density of the negative ligand, the larger the quantity of the preselected substance to be removed per unit weight of the porous element, thereby enhancing the adsorption capability. However, as the quantity of the negative ligand or the negative charge density of the negative ligand is increased, a large increase is likely to occur in bradykinin concentration.

The present inventors have found that even if the electric charge of the ligand is smaller than $-30$ μeq/g of the porous element, when the surface electric charge of the adsorptive filter medium as a whole (i.e., a balance between the respective electric charges of the ligand and the substrate) is not smaller than $-30$ μeq/g of the porous element, an increase in bradykinin concentration of the blood material can be suppressed to a low level, causing substantially no adverse effect. When the surface of the substrate itself is electrically substantially neutral, the type and quantity of the ligand can be selected so that the electric charge of the ligand bonded to the surface of the substrate becomes not smaller than $-30$ μeq/g of the porous element. On the other hand, when it is desired to further improve the adsorption capability of the adsorptive filter medium of the present invention, this can be realized by using a porous element in which a ligand having an electric charge of smaller than $-30$ μeq/g of the porous element is used in combination with a porous substrate having introduced into a surface portion thereof, a positive group for offsetting a part of the negative charge of the ligand, so that the porous element as a whole has a surface electric charge of not smaller than $-30$ μeq/g of the porous element. In this case, the positive group which is introduced onto a surface portion of the substrate for offsetting a part of the negative charge of the ligand may or may not be a functional group capable of selectively binding at least one preselected substance thereto.

In the case of an adsorptive filter medium in which a negative ligand is bonded to a surface of a substrate having a positive group introduced onto a surface portion thereof, for ensuring excellent adsorption capability, it is preferred that the balance between the positive charge of the substrate and the negative charge of the negative ligand have a negative charge of not smaller than $-10$ $\mu$eq/g, that is, from $-30$ $\mu$eq/g to $-10$ $\mu$eq/g.

As the negative charge of the surface to be contacted with the blood material is increases, an increase is likely to occur in bradykinin concentration of the blood material. As a result of the investigations by the present inventors, it has been found that when a negative charge-containing ligand present in the surface is flexible, the surface is less likely to cause an increase in bradykinin concentration than a negative charge-containing rigid ligand surface having a negative charge. Therefore, when the substrate, bonded to a surface thereof, has a ligand, particularly a negative ligand, it is preferred that the ligand be immobilized onto the surface in a manner such that the ligand is present in a state as flexible as possible. From this viewpoint, when the substrate has a ligand, it is preferred that the ligand comprise a molecular chain (or whisker) having at least one portion thereof bonded to the surface of the substrate and having a remaining unbonded portion which is flexible, and movable. Such a chain-like ligand is advantageous also in that the adsorptive effect of the ligand extends to sites apart from the surface of the substrate so that the ligand provides an increased number of binding sites for a preselected substance to be adsorbed.

With respect to the negative ligand, the higher the density of negative functional groups in the negative ligand, the higher the binding (adsorbing) capability of the ligand for a preselected substance. However, when the density of negative functional groups is too high, an increase in bradykinin concentration is likely to occur. From the viewpoint of realizing a good binding capability for a preselected substance, it is preferred that the negative ligand have a negative functional group density such that the ligand has one negative functional group or more per 600 of the molecular weight of the ligand, more preferably one negative functional group or more per 300 of the molecular weight of the ligand and still more preferably one negative functional group or more per 200 of the molecular weight of the ligand. On the other hand, from the viewpoint of preventing an increase in bradykinin concentration, it is preferred that the ligand have a negative functional group density such that the ligand has one negative functional group or less per 80 of the molecular weight of the ligand, more preferably one negative functional group or less per 120 of the molecular weight of the ligand and still more preferably one negative functional group or less per 150 of the molecular weight of the ligand.

Negative ligands can be selected from, for example, peptides, sugars and synthetic organic compounds. Representative examples of negative ligands include ligands having a sulfate group, a carboxyl group or a phosphate group illustrative examples of negative ligands include nucleic acids, such as adenine, thymine, guanine, cytosine and uracil and derivatives thereof; amino acids which are monoaminodicarboxylic acids, such as glutamic acid and aspartic acid and derivatives thereof; compounds containing the above-mentioned nucleic acids or derivatives thereof and the above-mentioned amino acids or derivatives thereof; oligomers or polymers of the above-mentioned nucleic acids or derivatives thereof and of the above-mentioned amino acids or derivatives thereof; polysaccharide sulfates, such as heparin, dextran sulfate, chondroitin sulfate, chondroitin polysulfate, heparan sulfate, keratan sulfate, heparitin sulfate, xylan sulfate, charonin sulfate, cellulose sulfate, chitin sulfate, chitosan sulfate, pectin sulfate, inulin sulfate, alginic acid sulfate, glycogen sulfate, polylactose sulfate, carrageenan sulfate, starch sulfate, polyglucose sulfate, galactan sulfate, levan sulfate and mepesulfate; and other compounds, such as phosphotungstic acid, anethole polysulfate, polyvinyl alcohol sulfate, polyphosphoric acid, poly(acrylic acid), 2-sulfoethyl methacrylate, crotonic acid, vinyl sulfonic acid, allyl sulfonic acid and methallyl sulfonic acid. Of these examples, a synthetic compound is preferred since it is not likely to exhibit immunogenicity upon being detached from a substrate and to cause other physiological reactions. Especially preferred is a synthetic compound having a sulfate group since such a compound adsorbs a relatively small quantity of bivalent metal ions. Representative examples of preferred compounds include dextran sulfate.

When positive groups are immobilized onto a surface of a substrate having a negative ligand bonded to the surface thereof, the manner of immobilization of the positive groups onto the surface of the substrate is not particularly limited. The positive groups may be immobilized in the form of a monomer or a polymer. When the positive groups are immobilized in the form of a polymer, it is not desired that the polymer be of a long chain (or whisker) having a portion which is flexible and movable, since such a polymer chain is likely to adversely affect the function of the negative ligand.

The immobilization of positive groups can be performed by conventional methods which can be used for the immmobilization of a ligand. In general, however, a graft polymerization method is not preferred, since when the immmobilization is conducted by graft polymerization, the positive groups are likely to be immobilized in the form of a polymer chain having a portion which is flexible and movable. Examples of preferred methods for immobilizing positive groups include a method in which a monomer having positive groups is immobilized through covalent bonds, and a method in which a polymer having positive groups is coated on the surface of the substrate to form a coating. When positive groups are immobilized in the form of a coating, a negative ligand may be immobilized directly onto a surface of the substrate or may be immobilized on the coating. Especially preferred is a method in which a monomer having a molecular weight of 1,000 or less and having positive groups is immobilized onto the surface of the substrate through covalent bonds.

When positive groups are introduced to the surface of a substrate having a negative ligand, the positive groups may be introduced as a side chain of a main polymer chain constituting the substrate and, alternatively, the positive groups may be introduced as a part of the main polymer chain. Examples of known methods for introducing positive groups to the surface of the substrate (or to the surface of a coating formed on the surface of the substrate) include a cyanogen halide method, an epichlorohydrin method, a bisepoxide method and a bromoacetyl bromide method. Examples of positive groups to be introduced by these methods include an amino group, a carboxyl group, a hydroxyl group, a thiol group, an acid anhydride group, a succinyl imide group, a chloride group, an aldehyde group, an amido group, an epoxy group and a tresyl group. Of these positive groups, from the viewpoint of improving heat stability at the time of a heat treatment for sterilization, an epoxy group introduced by an epichlorohydrin method is especially preferred.

When a ligand having functional groups comprised mainly of positive functional groups (such a ligand is hereinafter frequently referred to as a "positive ligand") is bonded (immobilized) to the surface of the substrate so that the ligand can electrostatically bind a preselected substance thereto by virtue of the positive functional groups, for enhancing the compatibility of the substrate with a blood material, it is preferred that the surface of the substrate have negative groups. It is preferred that the positive ligand exist as a polymer (or whisker) on the surface of the substrate. It is preferred that the negative groups on the surface of the substrate be a substance having a molecular weight as low as 1000 or less, and that such negative groups are present in the form of a coating but not in the form of a chain (or whisker).

As mentioned above, a rigid surface is more likely to cause an increase in bradykinin concentration than a flexible surface. For this reason, in the case of an adsorptive filter medium in which a positive ligand is bonded to the surface of the substrate, the quantity of negative groups on the surface of the substrate markedly affects the degree of increase in bradykinin concentration. Thus, in an adsorptive filter medium (having a negative group on the surface of the substrate) in which the ligand is a compound having positive functional groups, when the surface electric charge of the adsorptive filter medium as a whole (i.e., the balance between the respective electric charges of the ligand and substrate) is not smaller than $-30$ μeq/g of the porous element, an increase in bradykinin concentration can be suppressed. However, when the quantity of negative groups on the surface of the substrate is not greater than 30 μeq/g of the porous element (in absolute value), an increase in bradykinin concentration can be markedly suppressed.

Examples of positive ligands include polymers which are prepared from monomers, such as allylamine, diallylamine, N,N-dimethylallylamine, N,N-diallylpiperazine, N,N-diallylaniline, N,N-diallylmelamine, aminostyrene, N,N-dimethylaminostyrene, N,N-diethylaminostyrene, vinylbenzylamine, vinylphenethylamine, N,N-dimethylvinylphenethylamine, N,N-diethylvinylphenethylamine, N-propylvinylphenethylamine, vinylpyridine, 2-methyl-5-vinylpyridine, 2-ethyl-5-vinylpyridine, 2-vinylquinoline, 2-vinylimidazole, 4-vinylimidazole, vinylpyrazoline, vinylpyrazine, 4-vinylpyrimidine, vinylamine, vinylcarbazole, ethyleneimine, N-phenylethyleneimine, N,N-diethyl-N-vinylphenethylamine, diethylaminoethyl methacrylate, dimethylaminoethyl methacrylate, diethylaminoethylstyrene, and the like.

Examples of polymers suitable for providing a positive ligand include diethylaminoethyl styrene, N,N-diethyl-N-vinylphenethylamine, diethylaminoethyl methacrylate and dimethylaminoethyl methacrylate.

The positive ligand may be a copolymer of the above-mentioned monomer with a comonomer, such as hydroxystyrene, hydroxymethyl styrene, vinyl alcohol, 2-hydroxyethyl acrylate, 2-hydroxyethyl methacrylate, segmented polyurethane and segmented polyester. Especially it is preferred that the polymer contains a hydroxyl group from the viewpoint of increasing compatibility with a blood material. There is no particular restriction with respect to the bonded manner of the hydroxyl group in the polymer. It is especially preferred that the positive ligand be a copolymer of 1 to 50% by weight of a monomer having a positive functional group represented by the formula (described hereinbefore)

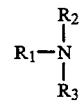

wherein each of $R_1$, $R_2$ and $R_3$ is defined above, and a balance of a monomer having a hydroxyl group.

It is preferred that each of a negative ligand and a positive ligand be a polymer in which at least two negative (or positive) functional groups are contained. When the number of negative (or positive) functional groups per mole of the ligand is small, the negative (or positive) functional group is likely to be electrostatically bonded to the positive (or negative) group on the surface of the substrate, thereby making it impossible to exhibit the binding ability of the ligand to a preselected substance. When the number of functional groups per ligand is satisfactorily large, even if a part of the functional groups are electrostatically bonded to a group (having an opposite electric charge) on the surface of a substrate, the remaining part of the functional groups can extend to sites apart from the surface of the substrate to thereby render it possible to firmly bind a preselected substance.

Further, by sterilization treatment in the production process of the adsorptive filter medium, or by the action of pH conditions, oxygen or ultraviolet radiation during prolonged storage of the adsorptive filter medium, a part of the ligands is decomposed, thereby causing the decomposed substance to enter a living body, leading to an occurrence of an unfavorable physiological reaction. However, when a group having an electric charge opposite to the electric charge of the ligand is present on the surface of the substrate, a functional group in the decomposed substance derived from the ligand is electrostatically bonded to the group on the surface of the substrate, so that dissolution-out of the ligand is advantageously substantially prevented.

The molecular weight of each of the positive ligand and the negative ligand is preferably in the range of from 1,000 to 1,000,000. When the molecular weight is less than 1,000, the number of functional groups in the ligand becomes too small, so that the favorable above-mentioned effect due to being a polymer cannot be exerted. On the other hand, when the molecular weight is more than 1,000,000, the viscosity of the ligand solution (to be used in bonding the ligand to a substrate surface) becomes too high, so that not only can a uniform immobilization of ligands to the substrate surface not be achieved, but also accidental detaching of the high molecular weight ligand causes serious problems.

When the preselected substance is a high molecular weight substance, such as a protein, the preselected substance has an increased number of sites to be bound to a ligand. Therefore, the molecular weight of the ligand is preferably in the range of from 5,000 to 500,000. Particularly, the molecular weight of a positive ligand not greater than 200,000 is most preferred.

When the ligand contains both a negative functional group and a positive functional group, the balance (difference) between the positive and negative charges respectively ascribed to both the functional groups as measured under neutral pH conditions is the electric charge of the ligand.

Examples of ligands having both a negative functional group and a positive functional group include polymers which are obtained by polymerization of a positive functional group-containing compound and a negative functional group-containing compound; and amino acids or derivatives thereof and compounds containing the same, which are in the form of monomers, oligomers or polymers. Among these, preferred are amino acids or the derivatives thereof or compounds containing the same, which are in the form of monomers, oligomers or polymers. Of these most preferred are the monomers and oligomers.

The molecular weight of the ligand is not particularly limited. However, from the viewpoint of the effect on a the living body at the time when the ligand is released, the molecular weight is preferably 200,000 or less. Especially, because the amino acids, the derivatives thereof, or compounds containing these, are likely to show immunogenicity, the molecular weight thereof is preferably 30,000 or less, more preferably 5,000 or less, most preferably 1,000 or less.

When the ligand does not contain a functional group, the electric charge on the substrate surface is determinative with respect to the surface electric charge of the composite filter medium and, therefore, the electric charge must be such as to provide a surface electric charge of not smaller than $-30$ $\mu$eq/g of the porous element.

As a method for immobilizing a ligand to the surface of the substrate, there can be mentioned conventional techniques, such as covalent bonding, ionic bonding, physical adsorption, embedding and precipitation-immobilization. From the viewpoint of the danger of the ligands becoming detached or dissolving out, it is preferred that the ligands be immobilized by covalent bonding. When the molecular weight of the ligand is 1,000 or more, and negative functional groups, such as a carboxyl group, sulfate group and sulfate ester group are present in an amount of at least one functional group per 300 of the molecular weight of the ligand, even ionic bonding can be employed because the ligands can be firmly bonded to the surface of the substrate at an increased number of binding sites.

As a method for covalently bonding a ligand to the surface of the substrate, there can be mentioned conventional methods, such as a method as used for immobilizing of an enzyme, a substrate activation and ligand immobilization method as used in immobilizing a ligand to a substrate in the case of affinity chromatography, and graft polymerization method in which the substrate is used as a stem polymer and a ligand is used as a branch.

Examples of conventional activation methods include a cyanogen halide method, an epichlorohydrin method, a bisepoxide method, a triazine halide method, a bromoacetylbromide method, an ethylchloroformate method, a 1,1'-carbonyldiimidazol method, a tosyl chloride method, an acetamide method and the like.

However, in the present invention, a method for activation is not limited to the above examples, because the object can be attained if a substitution and/or addition reaction can occur between the substrate and a nucleophilic reactive group (having an activated hydrogen), such as amino group, hydroxyl group, carboxyl group and thiol group of the ligand. However, from the viewpoint of chemical stability and thermal stability of the immobilized ligand, especially preferred is a method in which epoxide is employed, and most preferred is the epichlorohydrin method.

Examples of graft polymerization methods include a chain transfer method, an emulsion polymerization method, a graft polymerization method in which various polymerization initiators, such as cerium salt, persulfate salt-lithium halide and hydrogen peroxide-metal salt, are employed, a graft polymerization method in which polymerization is carried out using a compound having a functional group, such as perester group, mercapto group or diazo group, a graft polymerization method in which oxidation by air or ozone is used, a radiation graft method, and a plasma polymerization method.

Among the above-mentioned graft polymerization methods, preferable is the method in which a monomer having a negative functional group is graft polymerized onto a substrate having a reducing group, such as hydroxyl group, thiol group, aldehyde or amine, with the aid of an initiator, such as cerium salt or metal salt, under radiation such as gamma rays, or plasma.

The amount of a ligand to be immobilized to the surface of the substrate is preferably in the range of from 0.01 to 100 mg per 1 ml of the substrate. From the viewpoint of the balance of the adsorption capability of the adsorptive filter medium for a preselected substance and the cost of a ligand, the amount of a ligand to be immobilized is preferably in the range of from 0.1 to 10 mg per 1 ml of the substrate.

The bonding strength of a ligand with the polymeric, porous substrate varies depending on the number of covalent bonds per molecule of a high molecular weight compound constituting the ligand. In addition to the bonding by the covalent bond, a bonding due to the physical adsorption of a ligand to the substrate is also present, the bonding strength of which is weaker than that of the bonding by the covalent bond. It is impossible to exactly determine the total bonding strength of the ligand by separately evaluating both bonding strengths due to the covalent bond and to the physical adsorption. However, the following two values ("dissolution value" and "thermal dissociation value") can be used as an index of the bonding strength of a ligand.

Dissolution value: A porous element having a ligand comprised of a high molecular weight compound is immersed in a good solvent for the ligand. The ratio of the amount of the high molecular weight compound (ligand) which is dissolved out of the surface of the substrate to the total amount of the high molecular weight compound (ligand), is taken as the dissolution value. Examples of good solvents for a ligand include physiological saline and a 40% ethanol solution.

Thermal dissociation value: A porous element having a ligand comprised of a high molecular weight compound is treated in a neutral aqueous solution at 121° C. for 1 hour. The ratio of the amount of the high molecular weight compound (ligand) which is released from the surface of the substrate to the total amount of the high molecular weight compounds (ligand), is taken as the thermal dissociation value. Examples of neutral aqueous solutions include those containing phosphoric acid, carbonic acid, citric acid or salts thereof.

In the present invention, the dissolution value and the thermal dissociation value are, respectively, preferably not greater than 0.05 and not greater than 0.01, more preferably not greater than 0.01 and not greater than 0.001, most preferably not greater than 0.001 and not greater than 0.0001.

The material for the polymeric, porous substrate of the adsorptive filter medium of the present invention may be an inorganic or organic polymer. For example, alumina, silica gel, activated carbon, glass, apatite, natural or synthetic organic compounds can be used. Of these, organic polymers are preferred because they are resistant to extraction in hot water and because the porosity of an organic polymer substrate can be easily and precisely controlled.

Examples of organic polymers include homopolymers or copolymers of vinyl compounds, such as polypropylene, polystyrene, polymethacrylate, polyacrylic acid or ester thereof and polyvinyl alcohol; polyamide compounds, such as nylon 6 and nylon 66; polyester compounds, such as polyethylene terephthalate; and polysaccharide compounds derived from plants, such as cellulose.

Of these, a homopolymer or copolymer of vinyl compounds is most preferred because a negative or positive functional group can be easily introduced thereto. Representative examples of vinyl compounds include hydrocarbon compounds, such as styrene, methylstyrene, diphenylethylene, ethylethylene, dimethylstyrene, vinylnaphthalene, vinylphenanthrene, vinylmesitylene, 3,4,6-trimethylstyrene and 1-vinyl-2-ethylacetylene; styrene derivatives, such as chlorostyrene, methoxystyrene, bromostyrene, cyanostyrene, fluorostyrene, dichlorostyrene, N,N-dimethylaminostyrene, nitrostyrene, chloromethylstyrene, trifluorostyrene, trifluoromethylstyrene and aminostyrene; acrylonitrile and its derivatives, such as α-acetoxyacrylonitrile; acrylic acid and its ester, such as methyl acrylate, lauryl acrylate, chloromethyl acrylate and ethyl acetoxyacrylate; methacrylic acid and its ester, such as cyclohexyl methacrylate, dimethylaminoethyl methacrylate, glycidyl methacrylate, tetrahydrofurfuryl methacrylate and hydroxyethyl methacrylate; diethyl maleate and diethyl fumarate; vinyl ketone, such as methyl vinyl ketone and ethyl isopropenyl ketone; vinylidene compounds, such as vinylidene chloride, vinylidene bromide and vinylidene cyanide; acrylamide and its derivatives, such as methacrylamide, N-butoxymethyl acrylamide, N-phenyl acrylamide, diacetone acrylamide and N,N-dimethylaminoethyl acrylamide; vinyl derivatives of aliphatic acids, such as vinyl acetate, vinyl butyrate and vinyl caprate; thiofatty acid derivatives, such as phenyl thiomethacrylate, methyl thioacrylate and vinyl thioacetate; heterocyclic vinyl compounds, such as N-vinylsuccinimide, N-vinylpyrrolidone, N-vinylphthalimide, N-vinylcarbazole vinylfuran, vinylthiophene, vinylimidazole, methylvinylimidazole, vinylpyrazole, vinyloxazolidone, vinylthiazole, vinyltetrazole, vinylpyridine, methylvinylpyridine, 2,4-dimethyl-6-vinyltriazine and vinylquinoline.

Examples of cross-linking monomers which can be used for preparing the substrate include divinylbenzene, divinyltoluene, divinylxylene, divinylnaphthalene, divinylethylbenzene, divinylphenanthrene, trivinylbenzene, divinyl diphenyl, divinylphenyl ether, divinyl diphenyl sulfide, divinyl diphenylamine, divinyl sulfone, divinyl ketone, divinyl furan, divinyl pyridine, divinyl quinoline, di(vinylpyridinoethyl)ethylenediamine, diallyl phthalate, diallyl maleate, diallyl fumarate, diallyl succinate, diallyl carbonate, diallyl oxalate, diallyl adipate, diallyl sebacate, diallyl tartrate, diallyl amine, triallylamine, triallyl phosphate, triallyl tricarballylate, triallyl aconitate, triallyl citrate, N,N-ethylenediacrylamide, N,N-ethylenedimethacrylamide, N,N-methylenedimethacrylamide, ethylene glycol methacrylate, triethylene glycol dimethacrylate, polyethylene glycol dimethacrylate, trimethylolpropane trimethacrylate, pentaerythritol tetramethacrylate, 1,3-butylene glycol diacrylate, 1,6-hexanediol diacrylate, trimethylpropane triacrylate, pentaerythritol tetraacrylate, triallyl isocyanurate, 1,2,5-triacryloylhexahydro-1,3,5-triazine, diaryl melamine and the like.

Of various polymers usable as a material for the polymeric, porous substrate, it is preferred to employ a rigid gel which comprises at least one of (1) a synthetic organic polymer comprising at least one member selected from the group consisting of methylmethacrylate, polyvinyl alcohol, styrene, divinylbenzene, vinyl acetate, maleic anhydride, polyamide and the like, and (2) a natural polymer, such as cellulose.

With respect to the pore size of the polymeric, porous substrate, the substrate has an average pore size of at least 10,000 in terms of an exclusion limit molecular weight. When the average pore size in terms of an exclusion limit molecular weight is less than 10,000, the effective surface area of the substrate, which serves to adsorb a preselected substance, becomes small. On the other hand, when the average pore size in terms of an exclusion limit molecular weight is more than 10,000,000, although a preselected substance can easily go into the pores of the substrate, the effective surface area becomes small and the strength of the substrate is lowered. Preferably, the average pore size of the substrate in terms of an exclusion limit molecular weight is from 100,000 to 5,000,000.

For the same reasons as mentioned above, when the pore size is measured by mercury porosimetry, the lower limit of the average pore diameter of the polymeric, porous substrate is not smaller than 50 Å, preferably not smaller than 200 Å, still more preferably not smaller than 300 Å. On the other hand, the upper limit of the average pore diameter of the substrate is not greater than 5,000 Å, preferably not greater than 3,000 Å, as measured by mercury porosimetry.

The measurement of the average pore size in terms of an exclusion limit molecular weight and the measurement thereof by mercury porosimetry are different in their measuring principles. In the present invention, it is practical to employ an average pore size in terms of an exclusion limit molecular weight, which is determined under conditions similar to the actual use conditions for the adsorptive filter medium.

In the present invention, it is preferred that the pore diameters of the pores of the polymeric, porous substrate be as uniform as possible, and that the pore diameters be as close to a predetermined pore diameter as possible. Illustratively stated, the sum of respective pore volumes of pores having a pore diameter of from 100 to 5,000 Å is preferably not less than 40%, more preferably not less than 60%, based on the total pore volume. However, since the size of a preselected substance to be removed by adsorption-filtration is not uniform, it is not preferred that the pore diameters of pores be too uniform. When the pore diameters are too uniform, a preselected substance having a larger size is likely to be unable to enter the pores, so that the pores are covered and the pore surfaces thereof cannot effectively function for adsorption-filtration. For avoiding the above problem, when an average pore diameter is defined as "D", the sum of respective pore volumes of pores having a pore diameter of from 0.5 D to 2.0 D is preferably not more than 70%, more preferably not more than 50%, based on the total pore volume.

The porosity of the polymeric, porous substrate is preferably from 30 to 95%, more preferably from 50 to 90%, based on the total volume of the substrate. When the porosity exceeds 95%, the strength of the substrate is likely to be lowered.

It is preferred that a substrate have the above-mentioned values of pore size, pore volume and porosity as measured with respect to the substrate which is in a state as close to the state thereof at the time of actual use as possible. For example, when the polymeric, porous substrate has a coating thereon, the average pore diameter, pore volume and porosity are required to be those as measured after the coating. When the substrate undergoes a change in morphology after a drying treatment conducted in mercury porosimetry, a change in the particle diameter of the substrate is measured and then, a value of surface area is corrected by multiplying with the second power of the change ratio of the particle diameter, and a value of pore volume is corrected by multiplying with the third power of the change ratio of the particle diameter. That is, when the change ratio of the particle diameter is 1/X, the surface area and the pore volume are multiplied with $1/X^2$ and $1/X^3$, respectively. Also, a pore diameter and a pore surface area are corrected in the same manner as mentioned above. Further, if desired, appropriate correction can be made with reference to the apparent specific gravity and the swell ratio.

The specific surface area of the polymeric, porous substrate can be measured by various methods, such as a physical adsorption method, an immersion thermal method, a permeation method, a chemical adsorption method, mercury porosimetry and the BET (Brunauer-Emmett-Teller) method. In general, the BET method is used.

In the present invention, the specific surface area of the polymeric, porous substrate is preferably not less than 5 $m^2/g$ of the substrate on a dry basis, more preferably not less than 10 $m^2/g$, still more preferably not less than 20 $m^2/g$, most preferably not less than 30 $m^2/g$.

Further, by mercury porosimetry, the sum of respective surface areas of pores having a specific pore diameter can be determined with high precision. In the present invention, the sum of respective surface areas of pores having a pore diameter of from 100 to 5,000 Å is preferably not less than 30%, more preferably not less than 50%, based on the sum of respective surface areas of pores having a pore diameter of from 60 to 80,000 Å.

The morphology of the polymeric, porous substrate is not particularly limited. Preferred examples of morphologies include those of a sphere, a particle, a filament, a hollow fiber and a flat membrane. Of these, from the viewpoint of assuring a good flow of blood material through the substrate, a spherical or particulate morphology is most preferred. In the case of a spherical or particulate morphology, the porous substrate preferably has an average particle diameter of from 10 to 10,000 μm, more preferably 25 to 1,000 μm, still more preferably 50 to 600 μm.

The porous substrate of the adsorptive filter medium preferably has a true specific gravity of from 0.5 to 2.0. More preferably, the true specific gravity of the porous substrate is from 0.7 to 1.5.

The swell ratio of the porous substrate (i.e., the ratio of the volume of the porous substrate in a swollen state, inclusive of the pore volume thereof, to the volume of the porous substrate in a dry state, inclusive of the pore volume thereof) is preferably 30 or less, more preferably 20 or less, still more preferably 10 or less. When a swell ratio exceeds 30, the mechanical strength of the porous substrate is disadvantageously lowered.

From the viewpoint of preventing a dimensional change (or distortion) of a porous substrate under filtration pressure and preventing an increase in the filtration pressure during a filtration operation, it is preferred that the porous substrate have a satisfactory hardness (or rigidity). For example, the porous substrate of the adsorptive filter medium is desired to have a hardness such that when the filter medium comprising the porous substrate is swollen and packed in a casing having an inlet and an outlet and having a diameter of 10 mm and a length of 50 mm and water is flowed through the filter medium-packed casing from the inlet to the outlet with a pressure difference of 200 mmHg between the inlet and the outlet, the decrease in the volume of the porous substrate is 10% or less.

The adsorptive porous element may have a coating of a hydrophilic polymer which improves affinity to blood and is capable of suppressing the adhesion of platelets. In general, since blood samples are not always easily available and vary in quality, it is difficult to precisely and stably evaluate the affinity of a polymer to blood. However, the hydrophilicity of a polymer has a close correlation with the affinity thereof to blood and, therefore, its affinity to blood can be easily evaluated through the evaluation of its hydrophilicity. The hydrophilicity of a porous element can be easily evaluated, for example, by measuring the contact angle of the porous element against gas bubbles in water. In the present invention, when the adsorptive porous element is in a sheet form or a film form, the porous element preferably exhibits a contact angle of 20° or more against gas bubbles in water, as measured at 25° C.

From the viewpoint of preventing the detachment of the hydrophilic coating from the porous substrate, it is preferred that the hydrophilic coating on the porous substrate be formed from a polymer. Examples of monomers which can be used for producing a hydrophilic polymer coating include acrylic acid, methacrylic acid and derivatives thereof, such as 2-hydroxyethyl acrylate, 2-hydroxypropyl acrylate, 2-hydroxyethyl methacrylate, 2-hydroxypropyl methacrylate, 2-hydroxybutyl methacrylate, diethylaminoethyl methacrylate, dimethylaminoethyl methacrylate, methoxydiethylene glycol methacrylate, methoxytriethylene glycol methacrylate and glycerol monomethacrylate; methoxypolyethylene glycols, such as methoxytriethylene glycol; styrene derivatives, such as diethylaminoethyl styrene, hydroxystyrene and hydroxymethylstyrene; vinyl group-containing monomers, such as vinyl amine and vinyl alcohol; segmented polyurethane; segmented polyester; mono (2-methacryloyloxyethyl) acid phosphate; and mono (2-acryloyloxyethyl) acid phosphate. A homopolymer, a copolymer, a block copolymer and a graft copolymer and the like which are comprised of one or more of the above-mentioned monomers, may be employed for forming a coating. Also, a graft copolymer containing a monomer having a polyethylene oxide chain may be employed.

Particularly preferred as a coating polymer is a polymer having a hydroxyl group. With respect to the manner of linkage of a hydroyl group with other moieties in the polymer, there is no particular limitation. As an example of a polymer having a hydroxyl group, there can be mentioned a copolymer of 0.1 to 20% by weight of monomer units having a positive functional group and a balance of monomer units having a hydroxyl group. The configuration of a polymer is not particularly limited and the polymer may be, for example, a linear polymer, a graft polymer or a cross-linked polymer.

The method of forming a polymer coating is not limited to a coating method. A coating can also be formed by a grafting method, a precipitation method and a covalent bonding method in which functional groups present on the surface of a porous element are utilized. From the practical viewpoint, a coating method, which is easy, is preferred.

The quantity of a coating to be formed on a porous substrate is preferably t 1 µg to 100 mg/g of the porous element on a dry basis, more preferably 10 µg to 10 mg/g of the porous element on a dry basis.

The adsorptive filter medium of the present invention is generally used in a form of an adsorber apparatus comprising a casing having an inlet and an outlet for whole blood or plasma, in which the filter medium is packed. The casing is provided with, for example, a mesh for preventing a leaking of the filter medium at the inlet and the outlet so that the filter medium is retained between the meshes. The adsorption filter medium of the present invention can be packed alone or with other adsorptive materials in the form of a mixture or a laminate. The capacity of the adsorber apparatus is preferably from 10 to 1,000 ml when it is used for extracorporeal circulation of a blood material.

The adsorber apparatus is preferably sterilized before use. Various methods of sterilization can be employed: for example, sterilization can be conducted using gas such as ethylene oxide, heat, or radiation with gamma rays or ultraviolet rays. A method using a high pressure steam is preferable, because, according to this method, the ligand of the filter medium is stably maintained and the filter medium can be sterilized in a swollen (wet) state.

The adsorptive filter medium of the present invention may be provided in a dry state. However, it is preferred that the filter medium be packed in a casing in a swollen state, because a wetting operation at the time of actual use can be omitted and the ligand can be stably maintained.

It is preferred that the adsorber apparatus containing the adsorptive filter medium of the present invention be filled with an aqueous solution, from the viewpoint of preventing generation of air bubbles at the time of actual use of the apparatus. The aqueous solution preferably contains a salt for obtaining an osmotic pressure which is close to that of whole blood or plasma. Further, use of a buffer solution is more preferable since its pH value can be controlled. The buffer solution may contain any acid and base which are conventionally used, but the pH value of the solution is preferably in the range of from 5 to 9. A reducing compound, such as pyrosulfite may also be contained in the solution.

In the clinical field, the adsorber apparatus of the present invention can be used by passing therethrough whole blood taken directly from a patient or from a container, such as a blood bag, containing previously collected whole blood. The adsorber apparatus can also be used for treating plasma by passing plasma therethrough. Plasma can be obtained by separating blood cell components from whole blood according to a conventional method.

Since bradykinin is gradually decomposed by kinases, such as angiotensin converting enzyme, which are present in plasma, when whole blood or plasma treated by an adsorber apparatus is injected to a recipient after it has been allowed to stand outside the apparatus for a sufficient period of time, an increase in kinin concentration upon adsorption-filtration becomes no problem. Therefore, the apparatus of the present invention exhibits an excellent effect especially when treated whole blood or plasma is promptly injected to a recipient. Particularly, the adsorber apparatus of the present invention can be effectively employed when treated whole blood or plasma is injected to a recipient within one hour, more effectively within 30 minutes, still more effectively within 10 minutes. The adsorber apparatus of the present invention can be employed most advantageously in extracorporeal circulation of a blood material.

Extracorporeal circulation of a blood material can be conducted, for example, as follows. Whole blood taken from a patient is separated into plasma and a blood cell product by a centrifugal separator or a membrane type plasma separator. The separated plasma is passed through the adsorber apparatus of the present invention for purification, and then returned to the patient together with the blood cell product. Alternatively, it is possible to pass the whole blood taken from the patient through the adsorber apparatus directly for purification. Of these two methods, the former is preferred, because the flow resistance of the adsorber apparatus is smaller and a higher total adsorption capacity can be attained.

Although a blood material can be passed through the adsorber apparatus in a manner that the blood material is caused to drip by the action of gravity, or by utilizing the blood pressure of the patient, it is preferable to pass the blood material by using a pump, so that the flow rate can be freely set and easily controlled.

Further, a blood material can be passed through the adsorber apparatus continuously or intermittently, depending on the purpose of the treatment or the conditions of equipment installed at the clinical operation site. It should be noted that the longer the time for which plasma is retained in the adsorber apparatus, the more the undesirable formation of bradykinin. Hence, the adsorber apparatus of the present invention is advantageously employed especially when the plasma is retained therein for 10 seconds or more, more advantageously for 1 minute or more and still more advantageously for 10 minutes or more. However, the retaining of plasma for a long time is likely to cause non-specific adsorption of plasma components or coagulation of blood. Thus, it is preferred that the retention time of plasma be less than 30 minutes.

The apparatus of the present invention containing an adsorptive filter medium having a negative ligand can be advantageously used for removing various undesired substances from a blood material. Examples of such undesired substances include a low density lipoprotein and/or a very low density lipoprotein; sulfatide-adhesive protein; an activated complement component; amyloid protein A; an immune complex; an autoantibody, such as anti-DNA antibody and rheumatoid factor, and/or immunocyte B producing the above-mentioned autoantibody; immunoglobulin L chain, blood coagulation factor VIII; blood coagulation factor IX; and $\beta_2$-microglobulin. Especially, the apparatus of the present invention containing a negative ligand type adsorptive filter medium can be advantageously used for adsorbing a low density lipoprotein and/or a very low density lipoprotein.

The apparatus of the present invention containing an adsorptive filter medium having a positive ligand can be advantageously used for removing various undesired substances from a blood material. Examples of such undesired substances include amyloid P protein, transthyretin, immunosuppressive acidic proteins, $\beta$-amyloid substance, serum amyloid A protein, serum amyloid A precursor protein, bilirubin, uric acid, bile acid, albumin-binding compounds, $\beta_2$-microglobulin and fatty acids. Especially, the apparatus of the present invention containing a positive ligand type adsorptive filter medium can be advantageously used for adsorbing serum proteins having an isoelectric point of 4.5 or less, including amyloid P protein, transthyretin, serum amyloid A protein and serum amyloid A precursor protein.

Further, the apparatus of the present invention can contain an adsorptive filter medium which has a ligand having both positive and negative functional groups or no functional groups. The apparatus containing this type of filter medium can be advantageously used for removing various undesired substances from a blood material. Examples of such undesired substances include an autoantibody, such as antiacetylcholine antibody, anti-RNA antibody, antiblood type substance and antiplatelet antibody; antiviral antigen-antibody; blood type substance; hormon; interleukin; tumor necrosis factor; transforming growth factor; platelet growth factor; cytokine, such as fibroblast growth factor; and prostaglandin.

PREFERRED EMBODIMENT OF THE INVENTION

The present invention will now be described in greater detail with reference to the following Examples and Comparative Examples, which should not be construed as limiting the scope of the present invention.

EXAMPLE 1

Chips (specific gravity: 1.37) of polyethylene terephthalate (PET, intrinsic viscosity=0.49) are sufficiently dried by means of a vacuum drier, and are conveyed into a hopper drier through the process line. The water content of the dried chips is 11 ppm. The dried chips are subjected to melt extrusion-spinning. In the spinning, a spinneret is positioned at a distance of 10 cm from a conveyor net, thereby obtaining a non-woven fabric having a weight of 40 g/m$^2$, a thickness of 0.32 mm and a bulk density of 0.125 g/cm$^3$ and having an average fiber diameter of 1.6 $\mu$m. The extrusion-spinning is conducted at 320° C. and at a steam temperature of 380° C. under a steam pressure of 2.5 atm. The rate of the extrusion is 0.2 g/min. The CWST value of the non-woven fabric is 58 dyn/cm. The average pore diameter of the non-woven fabric is 5.3 $\mu$m.

The surface electric charge of the non-woven fabric is measured as follows.

The non-woven fabric is well washed with 80% ethanol and washings are removed. The washed fabric is sufficiently dried. 1 g of the dried fabric is immersed in 50 ml of a methanol solution containing potassium iodide in a concentration of 5 % by weight. The resultant system is subjected to a reaction at 30° C. for 24 hours while shaking. After completion of the reaction, a supernatant is collected. The collected supernatant is subjected to absorption spectrometry at 359 nm and 290 nm to thereby obtain absorbances. As a control, the above-mentioned methanol solution per se is employed.

Separately, a non-woven fabric made of polypropylene and polyethylene is prepared. Onto the non-woven fabric is fixed methacrylic acid by radiation-graft copolymerization in a proportion of 0.572 meq/g of the fabric, to thereby obtain a methacrylic acid-fixed non-woven fabric having an average fiber diameter of 1.5 $\mu$m. Individually using varied quantities (weights) of the above-obtained methacrylic acid-fixed non-woven fabric, the same treatment with the methanol solution as described above is conducted, and subjected to absorption spectrometry to thereby obtain absorbances at 359 nm and 290 nm. The surface electric charge of the polypropylene-polyethylene non-woven fabrics has been obtained beforehand using ECH-Sepharose 4b (manufactured and sold by Pharmacia Fine Chemicals AB, Sweden) as a control.

From the absorbances obtained above using the methacrylic acid-fixed polypropylene-polyethylene non-woven fabric in varied quantities (weights), a calibration curve is obtained with respect to the relationships between the absorbances and the quantities of surface electric charges. Using the calibration curve, the quantity of surface electric charge of the PET non-woven fabric is determined, and found to be $-25.5$ $\mu$eq/g.

Further, an increase in bradykinin concentration of a blood material upon being contacted with the PET non-woven fabric is measured as follows.

Whole blood is collected using CPD (citrate phosphate dextrose) as an anticoagulant and then, treated to prepare a red cell concentrate (hematocrit value: 65%). The red cell concentrate is admixed with a physiological saline containing 11.1% of ACD-A to thereby adjust a hematocrit value to 45%. Thus, a blood sample is obtained. 5 ml of the blood sample is placed in an Erlenmeyer flask made of polycarbonate. A 1.35 cm$\times$4.04 cm specimen of the non-woven fabric is immersed in the charged blood. The obtained system is subjected to a reaction at 37° C. for 5 minutes. Immediately after completion of the reaction, the treated blood sample is collected, cooled with ice, and, under ice-cooled conditions, admixed with 5000 U of tradirol, 2 mg of soy bean trypsin inhibitor, 5 mg of protamine sulfate and 20 mg of sodium ethylenediaminetetraacetate to thereby obtain a mixture. At 4° C., the obtained mixture is subjected to centrifugation at 3000 rpm for 10 minutes to thereby obtain a supernatant. The bradykinin concentration of the supernatant is measured by a radioimmunoassay method in which bradykinin is precipitated with polyethyleneglycol. The bradykinin concentration of the supernatant is 772 pg/ml. In a control experiment in which the same operation as described above is repeated except that a non-woven fabric is not immersed in the blood sample, the bradykinin concentration of plasma as the supernatant is 65.4 pg/ml. The above results indicate that an increase in bradykinin concentration of the plasma upon being contacted with the non-woven fabric is as small as only about 10 times the bradykinin concentration of the control.

EXAMPLE 2

Chips (specific gravity: 1.37) of polyethylene terephthalate (intrinsic viscosity =0.49) are sufficiently dried by means of a vacuum drier, and are conveyed into a hopper drier through a process line. The water content of the dried chips is 13 ppm. The dried chips are subjected to melt extrusion-spinning. In the spinning, a spinneret is positioned at a distance of 10 cm from a conveyor net, thereby obtaining a non-woven fabric having a weight of 40 g/m$^2$, a thickness of 0.32 mm and a bulk density of 0.125 g/cm$^3$ and having an average fiber diameter of 2.4 μm. The extrusion-spinning is conducted at 310° C. and at a steam temperature of 330° C. under a steam pressure of 3.5 atm. The rate of the extrusion is 0.2 g/min. The CWST value of the non-woven fabric is 60 dyn/cm. The average pore diameter of the non-woven fabric is 15.3 μm. The total pore volume and the total pore surface area of the non-woven fabric are 0.55 ml/ml of the non-woven fabric and 0.40 m$^2$/ml of the non-woven fabric, respectively. The sum of respective pore volumes of pores of the non-woven fabric which have a pore diameter of from 1 to 30 μm is 75.5%, based on the total pore volume.

The surface electric charge of the non-woven fabric is −26.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 912 pg/ml, which indicates that the increase in kinin concentration of the plasma upon being contacted with the non-woven fabric is favorably very small as compared to that of the control described in Example 1.

EXAMPLE 3

Chips (specific gravity: 1.37) of polyethylene terephthalate (intrinsic viscosity=0.49) are sufficiently dried by means of a vacuum drier, and are conveyed into a hopper drier through a process line. The water content of the dried chips is 15 ppm. The dried chips are subjected to melt extrusion-spinning. In the spinning, a spinneret is positioned at a distance of 10 cm from a conveyor net, thereby obtaining a non-woven fabric having a weight of 40 g/m$^2$, a thickness of 0.32 mm and a bulk density of 0.125 g/cm$^3$ and having an average fiber diameter of 1.8 μm. The extrusion-spinning is conducted at 310° C. and at a steam temperature of 365° C. under a steam pressure of 3.0 atm. The rate of the extrusion is 0.2 g/min. The CWST value of the non-woven fabric is 58 dyn/cm. The average pore diameter of the non-woven fabric is 12.5 μm. The total pore volume and the total pore surface area of the non-woven fabric are 0.61 ml/ml of the non-woven fabric and 0.41 m$^2$/ml of the non-woven fabric, respectively. The sum of respective pore volumes of pores of the non-woven fabric which have a pore diameter of from 1 to 30 μm is 77 %, based on the total pore volume.

The surface electric charge of the non-woven fabric is −25.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 650 pg/ml, which indicates that the increase in kinin concentration of the plasma upon being contacted with the non-woven fabric is favorably very small as compared to that of the control described in Example 1.

EXAMPLE 4

Chips (specific gravity: 1.37) of polyethylene terephthalate (intrinsic viscosity=0.49) are sufficiently dried by means of a vacuum drier, and are conveyed into a hopper drier through a process line. The water content of the dried chips is 6 ppm. The dried chips are subjected to melt extrusion-spinning. In the spinning, a spinneret is positioned at a distance of 10 cm from a conveyor net, thereby obtaining a non-woven fabric having a weight of 40 g/m$^2$, a thickness of 0.32 mm and a bulk density of 0.125 g/cm$^3$ and having an average fiber diameter of 1.2 μm. The extrusion-spinning is conducted at 310° C. and at a steam temperature of 320° C. under a steam pressure of 2.5 atm. The rate of the extrusion is 0.3 g/min. The CWST value of the non-woven fabric is 58 dyn/cm. The average pore diameter of the non-woven fabric is 9.2 μm. The total pore volume and the total pore surface area of the non-woven fabric are 0.47 ml/ml of the non-woven fabric and 0.53 m$^2$/ml of the non-woven fabric, respectively. The sum of respective pore volumes of pores of the non-woven fabric which have a pore diameter of from 1 to 30 μm is 58%, based on the total pore volume.

The surface electric charge of the non-woven fabric is −21.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 491 pg/ml, which indicates that the increase in kinin concentration of the plasma upon being contacted with the non-woven fabric is favorably very small as compared to that of the control described in Example 1.

Comparative Example 1

The chips (specific gravity: 1.37) defined in Example 1 are subjected directly, without the hopper drier drying, to melt extrusion-spinning. The water content of the chips measured before the melt extrusion-spinning is 50 ppm. In the spinning, a spinneret is positioned at a distance of 60 cm from a conveyor net, thereby obtaining a non-woven fabric having a weight of 40 g/m$^2$, a thickness of 0.32 mm and a bulk density of 0.125 g/cm$^3$ and having an average fiber diameter of 1.7 μm. The extrusion-spinning is conducted at 310° C. and at a steam temperature of 320° C. under a steam pressure of 2.5 atm. The rate of the extrusion is 0.2 g/min. The CWST value of the non-woven fabric is 64 dyn/cm. The average pore diameter of the non-woven fabric is 12.5 μm. The total pore volume and the total pore surface area of the non-woven fabric are 0.41 ml/ml of the non-woven fabric and 0.38 m$^2$/ml of the non-woven fabric, respectively. The sum of respective pore volumes of pores of the non-woven fabric which have a pore diameter of from 1 to 30 μm is 70%, based on the total pore volume.

The surface electric charge of the non-woven fabric is −41.2 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 4,000 pg/ml, which indicates that the increase in kinin concentration of the plasma upon being contacted with the non-woven fabric is unfavorably very large as compared to that of the control described in Example 1.

COMPARATIVE EXAMPLE 2

The chips (specific gravity: 1.37) defined in Example 1 are subjected directly, without the hopper drier drying, to melt extrusion-spinning. The water content of the chips measured before the melt extrusion-spinning is 2350 ppm. In the spinning, a spinneret is positioned at a distance of 60 cm from a conveyor net, thereby obtaining a non-woven fabric having a weight of 40 g/m$^2$, a thickness of 0.32 mm and a bulk density of 0.125 g/cm$^3$ and having an average fiber diameter of 1.7 $\mu$m. The extrusion-spinning is conducted at 310° C. and at a steam temperature of 350° C. under a steam pressure of 3.5 atm. The rate of the extrusion is 0.25 g/min. The CWST value of the non-woven fabric is 66 dyn/cm. The average pore diameter of the non-woven fabric is 12.5 $\mu$m. The total pore volume and the total pore surface area of the non-woven fabric are 0.86 ml/ml of the non-woven fabric and 0.88 m$^2$/ml of the non-woven fabric, respectively. The sum of respective pore volumes of pores of the non-woven fabric which have a pore diameter of from 1 to 30 $\mu$m is 96%, based on the total pore volume.

The surface electric charge of the non-woven fabric is −79.5 $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 14,000 pg/ml, which indicates that the increase in kinin concentration of the plasma upon being contacted with the non-woven fabric is unfavorably very large as compared to that of the control described in Example 1.

EXAMPLE 5

Chips (specific gravity: 1.37) of polyethylene terephthalate (intrinsic viscosity=0.49) are sufficiently dried by means of a vacuum drier, and are conveyed into a hopper drier through a process line. The water content of the dried chips is 15 ppm. The dried chips are subjected to melt extrusion-spinning. In the spinning, a spinneret is positioned at a distance of 10 cm from a conveyor net, thereby obtaining a non-woven fabric having a weight of 40 g/m$^2$ a thickness of 0.32 mm and a bulk density of 0.125 g/cm$^3$ and having an average fiber diameter of 1.6 $\mu$m. The extrusion-spinning is conducted at 310° C. and at a steam temperature of 365° C. under a steam pressure of 3.0 atm. The rate of the extrusion is 0.2 g/min. The CWST value of the non-woven fabric is 58 dyn/cm. The average pore diameter of the non-woven fabric is 11.2 $\mu$m. The total pore volume and the total pore surface area of the non-woven fabric are 0.85 ml/ml of the non-woven fabric and 0.89 m$^2$/ml of the non-woven fabric, respectively. The sum of respective pore volumes of pores of the non-woven fabric which have a pore diameter of from 1 to 30 $\mu$m is 98%, based on the total pore volume.

The surface electric charge of the non-woven fabric is −25.1 $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 650 pg/ml, which indicates that the increase in kinin concentration of the plasma upon being contacted with the non-woven fabric is favorably very small as compared to that of the control described in Example 1.

EXAMPLE 6

Chips (specific gravity: 1.31) of polybutylene terephthalate (intrinsic viscosity=0.85) are sufficiently dried by means of a vacuum drier, and are conveyed into a hopper drier through a process line. The water content of the dried chips is 15 ppm. The dried chips are subjected to melt extrusion-spinning. In the spinning, a spinneret is positioned at a distance of 10 cm from a conveyor net, thereby obtaining a non-woven fabric having a weight of 40 g/m$^2$ a thickness of 0.32 mm and a bulk density of 0.125 g/cm$^3$ and having an average fiber diameter of 1.7 $\mu$m. The extrusion-spinning is conducted at 310° C. and at a steam temperature of 365° C. under a steam pressure of 3.0 arm. The rate of the extrusion is 0.2 g/min. The CWST value of the non-woven fabric is 58 dyn/cm. The average pore diameter of the non-woven fabric is 15.2 $\mu$m. The total pore volume and the total pore surface area of the non-woven fabric are 0.81 ml/ml of the non-woven fabric and 0.89 m$^2$/ml of the non-woven fabric, respectively. The sum of respective pore volumes of pores of the non-woven fabric which have a pore diameter of from 1 to 30 $\mu$m is 97%, based on the total pore volume.

The surface electric charge of the non-woven fabric is −25.0 $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 650 pg/ml, which indicates that the increase in kinin concentration of the plasma upon being contacted with the non-woven fabric is favorably very small as compared to that of the control described in Example 1.

COMPARATIVE EXAMPLE 3

The chips (specific gravity: 1.37) defined in Example 3 are subjected directly, without the hopper drier drying, to melt extrusion-spinning. The water content of the chips measured before the melt extrusion-spinning is 50 ppm. In the spinning, a spinneret is positioned at a distance of 60 cm from a conveyor net, thereby obtaining a non-woven fabric having a weight of 40 g/m$^2$ a thickness of 0 32 mm and a bulk density of 0.125 g/cm$^3$ and having an average fiber diameter of 1.6 $\mu$m. The extrusion-spinning is conducted at 310° C. and at a steam temperature of 350° C. under a steam pressure of 2.7 atm. The rate of the extrusion is 0.2 g/min. The CWST value of the non-woven fabric is 62 dyn/cm. The average pore diameter of the non-woven fabric is 16.1 $\mu$m. The total pore volume and the total pore surface area of the non-woven fabric are 0.75 ml/ml of the non-woven fabric and 0.80 m$^2$/ml of the non-woven fabric, respectively. The sum of respective pore volumes of pores of the non-woven fabric which have a pore diameter of from 1 to 30 $\mu$m is 71%, based on the total pore volume.

The surface electric charge of the non-woven fabric is −55.0 $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 7,200 pg/ml, which indicates that the increase in kinin concentration of the plasma upon being contacted with the non-woven fabric is unfavorably very large as compared to that of the control described in Example 1.

EXAMPLE 7

Chips (specific gravity: 1.37) of polyethylene terephthalate (intrinsic viscosity=0.49) are sufficiently dried by means of a vacuum drier, and are conveyed into a hopper drier through a process line. The water content of the dried chips is 15 ppm. The dried chips are subjected to melt extrusion-spinning. In the spinning, a spinneret is positioned at a distance of 10 cm from a conveyor net, thereby obtaining a non-woven fabric having a weight of 40 g/m$^2$, a thickness of 0.23 mm and a bulk density of 0.174 g/cm$^3$ and having an average fiber diameter of 1.2 μm. The extrusion-spinning is conducted at 320° C. and at a steam temperature of 380° C. under a steam pressure of 2.8 atm. The rate of the extrusion is 0.2 g/min. The CWST value of the non-woven fabric is 60 dyn/cm. The average pore diameter of the non-woven fabric is 12.5 μm. The total pore volume and the total pore surface area of the non-woven fabric are 0.86 ml/ml of the non-woven fabric and 0.95 m$^2$/ml of the non-woven fabric, respectively. The sum of respective pore volumes of pores of the non-woven fabric which have a pore diameter of from 1 to 30 μm is 96%, based on the total pore volume.

The surface electric charge of the non-woven fabric is −22.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 620 pg/ml, which indicates that the increase in kinin concentration of the plasma upon being contacted with the non-woven fabric is favorably very small as compared to that of the control described in Example 1.

COMPARATIVE EXAMPLE 4

The chips defined in Example 4 are subjected directly, without the hopper drier drying, to melt extrusion-spinning. The water content of the chips measured before the melt extrusion-spinning is 50 ppm. In the spinning, a spinneret is positioned at a distance of 60 cm from a conveyor net, thereby obtaining a non-woven fabric having a weight of 40 g/m$^2$, a thickness of 0.32 mm and a bulk density of 0.125 g/cm$^3$ and having an average fiber diameter of 1.8 μm. The extrusion-spinning is conducted at 320° C. and at a steam temperature of 360° C. under a steam pressure of 2.6 atm. The rate of the extrusion is 0.2 g/min. The CWST value of the non-woven fabric is 62 dyn/cm. The average pore diameter of the non-woven fabric is 8.6 μm. The total pore volume and the total pore surface area of the non-woven fabric are 0.85 ml/ml of the non-woven fabric and 0.90 m$^2$/ml of the non-woven fabric, respectively. The sum of respective pore volumes of pores of the non-woven fabric which have a pore diameter of from 1 to 30 μm is 97%, based on the total pore volume.

The surface electric charge of the non-woven fabric is −58.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 7,000 pg/ml, which indicates that the increase in kinin concentration of the plasma upon being contacted with the non-woven fabric is unfavorably very large as compared to that of the control described in Example 1.

COMPARATIVE EXAMPLE 5

Chips of polypropylene (specific gravity: 0.90) are subjected to melt extrusion-spinning. In the spinning, a spinneret is positioned at a distance of 45 cm from a conveyor net, thereby obtaining a non-woven fabric having a weight of 60 g/m$^2$, a thickness of 0.23 mm and an average fiber diameter of 1.2 μm. The CWST value of the non-woven fabric is 20 dyn/cm. The average pore diameter of the non-woven fabric is 10.5 μm. The total pore volume and the total pore surface area of the non-woven fabric are 0.84 ml/ml of the non-woven fabric and 0.89 m$^2$/ml of the non-woven fabric, respectively. The sum of respective pore volumes of pores of the non-woven fabric which have a pore diameter of from 1 to 30 μm is 95%, based on the total pore volume.

The surface electric charge of the non-woven fabric is −22.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 420 pg/ml. This value is favorable but the non-woven fabric has low hydrophilicity so that penetration of a blood material thereinto is poor.

COMPARATIVE EXAMPLE 6

A non-woven fabric of polybutylene terephthalate is subjected to the conventional radiation-graft copolymerization. That is, a non-woven fabric of polybutylene terephthalate is immersed in an aqueous solution containing 2-hydroxyethyl methacrylate, methacrylic acid and t-butanol in concentrations of 0.43% by weight, 0.082% by weight and 0.4% by weight, respectively. The solution is bubbled with nitrogen gas to replace any gas dissolved in the solution by nitrogen gas. After the bubbling, the solution is irradiated with 27.3 kGy (1.2 kGy/hour) of gamma rays to effect graft copolymerization. The average fiber diameter of the resultant non-woven fabric is 2.3 μm and the CWST value of the resultant non-woven fabric is 102 dyn/cm. The average pore diameter of the non-woven fabric is 8.66 μm. The total pore volume and the total pore surface area of the non-woven fabric are 0.87 ml/ml of the non-woven fabric and 0.93 m$^2$/ml of the non-woven fabric, respectively. The sum of respective pore volumes of pores of the non-woven fabric which have a pore diameter of from 1 to 30 μm is 97%, based on the total pore volume.

The surface electric charge of the non-woven fabric is −112 μeq/g as measured in accordance with the method described in Example 1.

The non-woven fabric is further subjected to measurement of an increase in kinin concentration of a blood material upon being contacted with the nonwoven fabric as described in Example 1. The kinin concentration of the plasma is 12,000 pg/ml, which indicates that the increase in kinin concentration of the plasma upon being contacted with the non-woven fabric is unfavorably very large as compared to that of the control described in Example 1.

COMPARATIVE EXAMPLE 7

A non-woven fabric of polybutylene terephthalate is subjected to the conventional radiation-graft copolymerization. That is, a non-woven fabric of polybutylene terephthalate is immersed in an aqueous solution containing 2-hydroxyethyl methacrylate, methyl methacrylate and t-butanol in concentrations of 0.43% by weight, 0.082% by weight and 0.4% by weight, respectively. The solution is bubbled with nitrogen gas to replace any gas dissolved in the solution by nitrogen gas. After the bubbling, the solution is irradiated with 27.3 kGy (1.2 kGy/hour) of gamma rays to effect graft copolymerization. The average fiber diameter of the resultant non-woven fabric is 1.8 $\mu$m and the CWST value of the resultant non-woven fabric is 90 dyn/cm. The average pore diameter of the non-woven fabric is 11.5 $\mu$m. The total pore volume and the total pore surface area of the non-woven fabric are 0.87 ml/ml of the non-woven fabric and 0.94 $m^2$/ml of the non-woven fabric, respectively. The sum of respective pore volumes of pores of the non-woven fabric which have a pore diameter of from 1 to 30 $\mu$m is 96%, based on the total pore volume.

The surface electric charge of the non-woven fabric is $-125$ $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 14,000 pg/ml, which indicates that the increase in kinin concentration of the plasma upon being contacted with the non-woven fabric is unfavorably very large as compared to that of the control described in Example 1.

EXAMPLE 8

The non-woven fabric of polyethylene terephthalate defined in Comparative Example 2 is subjected to substantially the same conventional radiation-graft copolymerization as in Comparative Example 5, except that an aqueous solution containing 2-hydroxyethyl methacrylate, N,N-dimethylaminoethyl methacrylate and t-butanol in concentrations of 0.4% by weight, 0.012% by weight and 0.4% by weight, respectively, is used in place of the solution employed in Comparative Example 5. The average fiber diameter and the CWST value of the resultant non-woven fabric are 1.7 $\mu$m and 102 dyn/cm, respectively. The average pore diameter of the non-woven fabric is 12.5 $\mu$m. The total pore volume and the total pore surface area of the non-woven fabric are 0.86 ml/ml of the non-woven fabric and 0.88 $m^2$/ml of the non-woven fabric, respectively. The sum of respective pore volumes of pores of the non-woven fabric which have a pore diameter of from 1 to 30 $\mu$m is 96%, based on the total pore volume.

The surface electric charge of the non-woven fabric is $-23.3$ $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 712 pg/ml, which indicates that the increase in kinin concentration of the plasma upon being contacted with the non-woven fabric is favorably very small as compared to that of the control described in Example 1.

COMPARATIVE EXAMPLE 8

A non-woven fabric of polyethylene/polypropylene (1:1) having an average fiber diameter of 1.53 $\mu$m is subjected to the conventional radiation-graft copolymerization. That is, the above-mentioned non-woven fabric is immersed in a methanol solution containing 2.5% by weight of p-styrenesulfonic acid. The solution is bubbled with nitrogen gas to replace any gas dissolved in the solution by nitrogen gas. After the bubbling, the solution is irradiated with 27.3 kGy (1.2 kGy/hour) of gamma rays to effect graft copolymerization. The average fiber diameter of the resultant non-woven fabric is 1.5 $\mu$m and the CWST value of the resultant non-woven fabric is 104 dyn/cm. The average pore diameter of the non-woven fabric is 9.9 $\mu$m. The total pore volume and the total pore surface area of the non-woven fabric are 0.87 ml/ml of the non-woven fabric and 0.89 $m^2$/ml of the non-woven fabric, respectively. The sum of respective pore volumes of pores of the non-woven fabric which have a pore diameter of from 1 to 30 $\mu$m is 98%, based on the total pore volume.

The surface electric charge of the non-woven fabric is $-123$ $\mu$eq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 13,200 pg/ml, which indicates that the increase in kinin concentration of the plasma upon being contacted with the non-woven fabric is unfavorably very large as compared to that of the control described in Example 1.

EXAMPLE 9

The non-woven fabric of polyethylene terephthalate defined in Comparative Example 2 is subjected to conventional plasma irradiation graft-copolymerization. That is, the above-mentioned non-woven fabric is immersed in a methanol solution containing 10% by weight of methoxytriethylene glycol methacrylate and 0.5% by weight of N,N-dimethylaminoethyl methacrylate. Then, the non-woven fabric is taken out from the solution, dried by means of a vacuum drier, and irradiated with plasma for 3 minutes to effect graft copolymerization. The average fiber diameter and the CWST value of the resultant non-woven fabric are 1.7 $\mu$m and 74 dyn/cm, respectively. The average pore diameter of the non-woven fabric is 12.5 $\mu$m. The total pore volume and the total pore surface area of the non-woven fabric are 0.86 ml/ml of the non-woven fabric and 0.88 $m^2$/ml of the non-woven fabric, respectively. The sum of respective pore volumes of pores of the non-woven fabric which have a pore diameter of from 1 to 30 $\mu$m is 96%, based on the total pore volume.

The surface electric charge of the non-woven fabric is $-24.0$ $\mu$eq/g as measured in accordance with the method described in Example 1.

The non-woven fabric is further subjected to measurement of an increase in kinin concentration of a blood material upon being contacted with the nonwoven fabric as described in Example 1. The kinin concentration of the plasma is 712 pg/ml, which indicates that the increase in kinin concentration of the plasma upon being contacted with the non-woven fabric is favorably very small as compared to that of the control described in Example 1.

EXAMPLE 10

A spongy structure of polyvinylformal (specific gravity: 1.2) is subjected to substantially the same conventional plasma irradiation-graft copolymerization as in Example 9, except that a methanol solution containing 10% by weight of methoxynonaethylene glycol methacrylate and 0.5% by weight of N,N-dimethylaminoethyl methacrylate is used in place of the solution employed in Example 9. The CWST value of the resultant spongy structure is 74 dyn/cm. The average pore diameter of the spongy structure is 8.2 μm. The total pore volume and the total pore surface area of the spongy structure are 0.86 ml/ml of the spongy structure and 0.79 m$^2$/ml of the spongy structure, respectively. The sum of respective pore volumes of pores of the spongy structure which have a pore diameter of from 1 to 30 μm is 92%, based on the total pore volume.

The surface electric charge of the spongy structure is −23.0 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 672 pg/ml, which indicates that the increase in kinin concentration of the plasma upon being contacted with the spongy structure is favorably very small as compared to that of the control described in Example 1.

EXAMPLE 11

A spongy structure of polyvinylformal (specific gravity: 1.2) is subjected to substantially the same conventional plasma irradiation-graft copolymerization as in Example 9, except that a methanol solution containing 10% by weight of methoxytriethylene glycol methacrylate and 0.5% by weight of N,N-dimethylaminoethyl methacrylate is used in place of the solution employed in Example 9. The CWST value of the resultant spongy structure is 90 dyn/cm. The average pore diameter of the spongy structure is 30 μm. The total pore volume and the total pore surface area of the spongy structure are 0.82 ml/ml of the spongy structure and 0.77 m$^2$/ml of the spongy structure, respectively. The sum of respective pore volumes of pores of the spongy structure which have a pore diameter of from 1 to 30 μm is 91%, based on the total pore volume.

The surface electric charge of the spongy structure is −23.6 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 872 pg/ml, which indicates that the increase in kinin concentration of the plasma upon being contacted with the spongy structure is favorably very small as compared to that of the control described in Example 1.

COMPARATIVE EXAMPLE 9

The spongy structure of polyvinylformal defined in Example 10 is subjected to the conventional radiation-graft copolymerization in which use is made of 2% by weight of mono(2-methacryloyloxyethyl)acid phosphate to effect graft copolymerization. The CWST value of the resultant spongy structure is 100 dyn/cm. The average pore diameter of the spongy structure is 8.2 μm. The total pore volume and the total pore surface area of the spongy structure are 0.86 ml/ml of the spongy structure and 0.79 m$^2$/ml of the spongy structure, respectively. The sum of respective pore volumes of pores of the spongy structure which have a pore diameter of from 1 to 30 μm is 92%, based on the total pore volume.

The surface electric charge of the spongy structure is −118 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 12,700 pg/ml, which indicates that the increase in kinin concentration of the plasma upon being contacted with the non-woven fabric is unfavorably very large as compared to that of the control described in Example 1.

EXAMPLE 12

A spongy structure of polyurethane (specific gravity: 1.2) is subjected to substantially the same conventional radiation graft-copolymerization as in Comparative Example 7. That is, the above-mentioned spongy structure is immersed in a methanol solution containing 10% by weight of methoxytriethylene glycol methacrylate. Then, the spongy structure is taken out from the solution, dried by means of a vacuum drier, and graft copolymerized. The CWST value of the resultant spongy structure is 88 dyn/cm. The average pore diameter of the spongy structure is 8.8 μm. The total pore volume and the total pore surface area of the spongy structure are 0.85 ml/ml of the spongy structure and 0.90 m$^2$/ml of the spongy structure, respectively. The sum of respective pore volumes of pores of the spongy structure which have a pore diameter of from 1 to 30 μm is 95%, based on the total pore volume.

The surface electric charge of the spongy structure is −21.0 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 472 pg/ml, which indicates that the increase in kinin concentration of the plasma upon being contacted with the spongy structure is favorably very small as compared to that of the control described in Example 1.

COMPARATIVE EXAMPLE 10

The spongy structure of polyurethane defined in Example 12 is subjected to the conventional radiation-graft copolymerization. That is, the spongy structure of polyurethane is immersed in an aqueous solution containing 2-hydroxyethyl methacrylate, methacrylic acid and t-butanol in concentrations of 0.43% by weight, 0.082% by weight and 0.4% by weight, respectively.

The solution is bubbled with nitrogen gas to replace any gas dissolved in the solution by nitrogen gas. After the bubbling, the solution is irradiated with 27.3 kGy (1.2 kGy/hour) of gamma rays to effect graft copolymerization. The CWST value of the resultant spongy structure is 98 dyn/cm. The average pore diameter of the spongy structure is 8.7 μm. The total pore volume and the total pore surface area of the spongy structure are 0.85 ml/ml of the spongy structure and 0.90 m²/ml of the spongy structure, respectively. The sum of respective pore volumes of pores of the spongy structure which have a pore diameter of from 1 to 30 μm is 95%, based on the total pore volume.

The surface electric charge of the spongy structure is −128 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 14,400 pg/ml, which indicates that the increase in kinin concentration of the plasma upon being contacted with the spongy structure is unfavorably very large as compared to that of the control described in Example 1.

EXAMPLE 13

The non-woven fabric produced in Comparative Example 4 is subjected to the conventional esterification reaction using diazomethane to esterify some of the carboxyl groups contained in the non-woven fabric. The average fiber diameter and the CWST value of the resultant non-woven fabric are 1.6 μm and 58 dyn/cm, respectively. The average pore diameter of the non-woven fabric is 8.2 μm. The sum of respective pore volumes of pores of the non-woven fabric which have a pore diameter of from 1 to 30 μm is 98%, based on the total pore volume.

The surface electric charge of the non-woven fabric is −27.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 820 pg/ml, which indicates that the increase in kinin concentration of the plasma upon being contacted with the non-woven fabric is favorably very small as compared to that of the control described in Example 1.

EXAMPLE 14

The non-woven fabric produced in Comparative Example 2 is subjected to the conventional esterification reaction using diazomethane to esterify some of the carboxyl groups contained in the non-woven fabric. The average fiber diameter and the CWST value of the resultant non-woven fabric are 1.7 μm and 58 dyn/cm, respectively. The average pore diameter of the non-woven fabric is 12.5 μm. The sum of respective pore volumes of pores of the non-woven fabric which have a pore diameter of from 1 to 30 μm is 96.5%, based on the total pore volume.

The surface electric charge of the non-woven fabric is −24.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 620 pg/ml, which indicates that the increase in kinin concentration of the plasma upon being contacted with the non-woven fabric is favorably very small as compared to that of the control described in Example 1.

EXAMPLE 15

The non-woven fabric produced according to the conventional radiation-graft copolymerization in Comparative Example 8 is subjected to the conventional esterification reaction using diazomethane to esterify some of the carboxyl groups contained in the non-woven fabric. The average fiber diameter and the CWST value of the resultant non-woven fabric are 1.5 μm and 84 dyn/cm, respectively. The average pore diameter of the non-woven fabric is 9.9 μm. The sum of respective pore volumes of pores of the non-woven fabric which have a pore diameter of from 1 to 30 μm is 98%, based on the total pore volume.

The surface electric charge of the non-woven fabric is −29.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 900 pg/ml, which indicates that the increase in kinin concentration of the plasma upon being contacted with the non-woven fabric is favorably very small as compared to that of the control described in Example 1.

EXAMPLE 16

The non-woven fabric produced according to the conventional radiation-graft copolymerization in Comparative Example 8 is subjected to a conventional amidization reaction with diethylamine using dicyclohexylcarbodiimide known as an amidizing agent to amidize some of the carboxyl groups contained in the non-woven fabric. The average fiber diameter and the CWST value of the resultant non-woven fabric are 1.5 μm and 82 dyn/cm, respectively. The average pore diameter of the non-woven fabric is 9.9 μm. The sum of respective pore volumes of pores of the non-woven fabric which have a pore diameter of from 1 to 30 μm is 98%, based on the total pore volume.

The surface electric charge of the non-woven fabric is −22.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 650 pg/ml, which indicates that the increase in kinin concentration of the plasma upon being contacted with the non-woven fab-ric is favorably very small as compared to that of the control described in Example 1.

EXAMPLE 17

The spongy structure of polyurethane as used in Comparative Example 10 is subjected to the conventional esterification reaction using diazomethane to esterify some of the carboxyl groups contained in the spongy structure. The CWST value of the resultant spongy structure is 78 dyn/cm. The average pore diameter of the spongy structure is 8.6 μm. The sum of respective pore volumes of pores of the spongy structure which have a pore diameter of from 1 to 30 μm is 95%, based on the total pore volume.

The surface electric charge of the spongy structure is −28.0 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 870 pg/ml, which indicates that the increase in kinin concentration of the plasma upon being contacted with the spongy structure is favorably very small as compared to that of the control described in Example 1.

EXAMPLE 18

The spongy structure of polyvinylformal as used in Comparative Example 9 is subjected to conventional esterification reaction using diazomethane to esterify some of the phosphoric groups contained in the spongy structure. The CWST value of the resultant spongy structure is 80 dyn/cm. The average pore diameter of the spongy structure is 8.2 μm. The sum of respective pore volumes of pores of the spongy structure which have a pore diameter of from 1 to 30 μm is 92%, based on the total pore volume.

The surface electric charge of the spongy structure is −29.0 μeq/g as measured in accordance with the method described in Example 1.

The spongy structure is further subjected to measurement of an increase in kinin concentration of a blood material upon being contacted with the spongy structure as described in Example 1. The kinin concentration of the plasma is 970 pg/ml, which indicates that the increase in kinin concentration of the plasma upon being contacted with the spongy structure is favorably very small as compared to that of the control described in Example 1.

EXAMPLE 19

The surface of the non-woven fabric produced in Comparative Example 2 is partly covered with polymethoxytriethylene glycol methacrylate according to the conventional radiation-graft copolymerization. The average fiber diameter and the CWST value of the resultant non-woven fabric are 1.7 μm and 74 dyn/cm, respectively. The average pore diameter of the non-woven fabric is 12.5 μm. The sum of respective pore volumes of pores of the non-woven fabric which have a pore diameter of from 1 to 30 μm is 96.5%, based on the total pore volume.

The surface electric charge of the non-woven fabric is −28.5 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 850 pg/ml, which indicates that the increase in kinin concentration of the plasma upon being contacted with the non-woven fabric is favorably very small as compared to that of the control described in Example 1.

EXAMPLE 20

N,N-dimethylaminoethyl methacrylate (hereinafter referred to as D), 1,2-hydroxyethyl methacrylate (hereinafter referred to as HEMA), methyl methacrylate (hereinafter referred to as MMA) and methacrylic acid (hereinafter referred to as MAA) are added to 100% ethanol in concentrations of 0.015, 0.05, 0.03 and 0.0003 mol/l respectively. The volume of the mixture is adjusted to 250 ml. As a polymerization initiator, azobisisobutylonitrile (AIBN) is further added in a concentration of 0.01 mol/l. Polymerization reaction is effected at 45° C. in a nitrogen gas atmosphere for 4.5 hours. The reaction mixture is dropwise put into distilled water to precipitate a product. The precipitated product is recovered, and lyophilized to obtain a copolymer of DM, HEMA, MMA and MAA. This copolymer is dissolved in 100% ethanol in a concentration of 0.01 g/dl to obtain a copolymer solution.

The polyester non-woven fabric having an average fiber diameter of 1.7 μm as employed in Comparative Example 2 is charged into a vessel having an effective filtration area of 65 mm × 65 mm at a packing density of 0.2 g/cm³ and at a thickness of 3 mm. Subsequently, the above copolymer solution is charged into the vessel, and allowed to stand still for one minute. The charged copolymer solution is expelled with nitrogen gas, and nitrogen gas is continuously flowed for 10 minutes, followed by vacuum drying at 70° C. for 7 hours. Thus, a leukocyte-removing filter medium comprised of the polyester non-woven fabric coated with the copolymer is produced.

The average fiber diameter and the CWST value of the resultant non-woven fabric are 1.7 μm and 102 dyn/cm, respectively. The average pore diameter of the non-woven fabric is 12.5 μm. The sum of respective pore volumes of pores of the non-woven fabric which have a pore diameter of from 1 to 30 μm is 96.5%, based on the total pore volume.

The surface electric charge of the non-woven fabric is −28.0 μeq/g as measured in accordance with the method described in Example 1.

The non-woven fabric is further subjected to measurement of an increase in kinin concentration of a blood material upon being contacted with the non-woven fabric as described in Example 1. The kinin concentration of the plasma is 950 pg/ml, which indicates that the increase in kinin concentration of the plasma upon being contacted with the non-woven fabric is favorably very small as compared to that of the control described in Example 1.

EXAMPLE 21

A non-woven fabric comprised of polyethylene terephthalate (PET) fibers having an average fiber diameter of 1.6 μm is produced in substantially the same manner as in Example 5. The CWST value of the non-woven fabric is 58 dyn/cm. The average pore diameter of the non-woven fabric is 11.2 μm. The total pore volume and the total pore surface area of the non-woven fabric are 0.95 ml/ml of the non-woven fabric and 0.89 m²/ml of the non-woven fabric, respectively. The sum of respective pore volumes of pores of the non-woven fabric which have a pore diameter of from 1 to 30 μm is 98%, based on the total pore volume. The surface electric charge of the non-woven fabric is −25.0 μeq/g. The non-woven fabric is packed into a container having a blood inlet and a blood outlet and having an effective filtration cross-sectional area of 49 mm×49 mm so that the thickness of the packed non-woven fabric (main filter medium) becomes 3.3 mm (packing density: 0.15 g/cm$^3$ to obtain a filter apparatus for selectively removing leukocytes.

513 ml of blood prepared by adding 63 ml of CPD (citrate phosphate dextrose) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 5° C. Then, the red cell product is filtered by a filter prepared by packing, into a container having an effective filtration cross-sectional area of 67 mm×67 mm, a needled fibrous web having an average fiber diameter of 20 μm as a gel-capturing material, a non-woven fabric comprised of fibers having an average fiber diameter of 3 μm as a microaggregate (MA)-capturing material, and a non-woven fabric comprised of fibers having an average fiber diameter of 2.2 μm as a first stage leukocyte-capturing material. Thus, gel, MA and 90% of the leukocytes are removed from the red cell product. 200 ml of the thus treated red cell product is transferred to a fresh blood bag and filtered by the above-produced filter apparatus for selectively removing leukocytes.

The preparatory procedure before the filtration is performed by connecting the filter apparatus to the blood bag containing the red cell product through a blood circuit and manually applying pressure to the blood bag, thereby filling the filter apparatus with the blood. After filling the filter apparatus with the blood, the blood is caused to continuously flow at a constant rate of 5 ml/minute by means of PERISTA PUMP while measuring the pressure loss in the course of the filtration by means of a digital type pressure gauge. At the time when there is no longer blood in the blood bag, the filtration is completed, and the collection bag which has been connected to the downstream side of the filter apparatus through a blood circuit is cut off form the filter apparatus by cutting the blood circuit therebetween at a position 30 to 40 cm downstream of the blood outlet of the filter apparatus, thereby obtaining, as a collection liquid, the red cell product present in the collection bag and blood circuit.

The red cell product before filtration (hereinafter referred to as "pre-filtration liquid") and the collection liquid are measured with respect to the volume, the hematocrit and the number of leukocytes, thereby determining the red cell recovery and the leukocyte residual ratio.

Red Cell Recovery=[Collection Liquid Volume-×Hematocrit (Collection Liquid)]/[Pre-filtration Liquid Volume ×Hematocrit (Pre-filtration Liquid)].

Leukocyte Residual Ratio=[Number of Leukocytes (Collection Liquid)]/[Pre-filtration Liquid Volume-×Leukocyte Concentration (Pre-filtration Liquid)].

With respect to the volumes of the pre-filtration liquid and the collection liquid, values obtained by dividing the weights of these liquids by 1.075 (a representative value of the specific gravity of a red cell product) are taken as the respective volumes.

Further, the measurement of the leukocyte concentration of the pre-filtration liquid is performed by the following method.

The measurement of the leukocyte concentration of the pre-filtration liquid: A pre-filtration liquid diluted 10-fold with Türk's reagent is injected into a Burker-Türk type blood cell counting chamber and the leukocytes present in four major sections are counted through an optical microscope and the obtained number is taken as $n_{pre}$.

Leukocyte Concentration (before filtration)=$n_{pre} \times 0.25 \times 10^5$ cells/ml.

The measurement of the number of leukocytes contained in a collection liquid is performed by the extremely sensitive method described below.

100 ml of an EBSS solution (hereinafter referred to as "FICOLL solution") containing 5% FICOLL 400 DL is introduced into a bag containing 100 ml of a collection liquid while shaking to facilitate mixing. Then, the collection bag is fixed onto a plasma separation stand and allowed to stand still for 40 minutes. After that period, a supernatant is gently collected without disturbing a precipitated layer of red cells. Then, 100 ml of FICOLL solution is again introduced into the collection bag in the same volume as employed above, and the same procedure as described above is repeated. The supernatant collected by the collecting operation thus conducted twice is divided into four centrifuge tubes each being CORNING 25350 and centrifuged at 840×g for 15 minutes. Subsequently, the supernatant is discarded by means of an aspirator so carefully as not to withdraw the precipitate. 200 ml of a hemolysis solution (a 1.145% ammonium oxalate physiological saline solution) is introduced into each tube and the tubes are shaken to facilitate mixing, immediately followed by centrifugation at 468×g for 10 minutes. Subsequently, the supernatant is discarded by means of an aspirator while taking the same care as described above.

The precipitates in the four tubes are collected into a 15 ml centrifuge tube and a hemolysis solution is added thereinto so that the total volume becomes 15 ml. The tube is allowed to stand still at room temperature for 10 minutes and then centrifuged at 468×g for 10 minutes. Part of the supernatant is carefully discarded so that the volume of the contents, including the precipitates, becomes 0.5 ml. The liquid in the tube containing the precipitates is stirred well to obtain a single cell suspension, and 50 μl of a fluorescent dyeing solution (69.9 mg/l Acridine Orange) is added, followed by stirring. The resultant liquid is injected into six blood cell counting chambers of improved Neubauer type and the leukocytes present in 108 major sections are counted through an epifluorescent microscope.

From the resultant count ($n_{post}$) of leukocytes, the number of leukocytes (collection liquid) is calculated.

Number of Leukocytes (Collection Liquid) =

[$\underline{n_{post} \times (1/108) \times 10^4} \times 0.55 \times (1/0.55)$] × [Volume of Collection Liquid (ml)/100]

The underlined portion in the formula represents the leukocyte concentration (cells/ml) in the liquid (hereinafter referred to as "concentrate") obtained by concentrating the collection liquid using a FICOLL solution to a total volume of 0.55 ml. The leukocyte concentration is multiplied by the volume of the concentrate (0.55 ml) to obtain the number of leukocytes. The reason why the thus obtained number of leukocytes is further divided by 0.55 is that the recovery of leukocytes attained by means of a FICOLL solution is 55%.

As a result of the above calculations, it is found that good results are obtained. That is, the leukocyte residual ratio is $10^{-4.5}$ and the pressure loss at the time of completion of the filtration is 26 mmHg. Further, the blood sampled from the blood outlet is subjected to a measurement of the kinin concentration of the plasma as described in Example 1. The kinin concentration of the plasma is 750 pg/ml, which indicates that the increase in kinin concentration of the plasma upon being contacted with the non-woven fabric is favorably very small as compared to that of the control noted in Example 1.

COMPARATIVE EXAMPLE 11

A non-woven fabric comprised of polyethylene terephthalate (PET) fibers having an average fiber diameter of 1.6 μm is produced in substantially the same manner as in Comparative Example 3. The CWST value of the non-woven fabric is 62 dyn/cm. The average pore diameter of the non-woven fabric is 15.1 μm. The total pore volume and the total pore surface area of the non-woven fabric are 0.85 ml/ml of the non-woven fabric and 0.89 m$^2$/ml of the non-woven fabric, respectively. The sum of respective pore volumes of pores of the non-woven fabric which have a pore diameter of from 1 to 30 μm is 97%, based on the total pore volume. The surface electric charge of the non-woven fabric is −46.0 μeq/g. The non-woven fabric is packed into a container having a blood inlet and a blood outlet and having an effective filtration cross-sectional area of 49 mm×49 mm so that the thickness of the packed non-woven fabric (main filter medium) becomes 3.3 mm (packing density: 0.15 g/cm$^3$) to obtain a filter apparatus for selectively removing leukocytes.

513 ml of blood prepared by adding 63 ml of CPD (citrate phosphate dextrose) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 25° C. Then, the red cell product is filtered by a filter apparatus prepared by packing, into a container having an effective filtration cross-sectional area of 67 mm×67 mm, a needled fibrous web having an average fiber diameter of 20 μm as a gel-capturing material, a non-woven fabric comprised of fibers having an average fiber diameter of 3 μm as a microaggregate (MA)-capturing material, and a non-woven fabric comprised of fibers having an average fiber diameter of 2.2 μm as a first stage leukocyte-capturing material. Thus, gel, MA and 90% of the leukocytes are removed from the red cell product. 200 ml of the thus treated red cell product is transferred to a fresh blood bag and filtered by the above-produced filter apparatus for selectively removing leukocytes.

As a result of the filtration conducted in substantially the same manner as in Example 21, it is found that the leukocyte residual ratio is $10^{-4.4}$ and the pressure loss at the time of completion of the filtration is 28 mmHg. Further, the blood sampled from the blood outlet is subjected to a measurement of the kinin concentration of the plasma as described in Example 1. The kinin concentration of the plasma is 4,700 pg/ml, which indicates that the increase in kinin concentration of the plasma upon being contacted with the non-woven fabric is unfavorably very large as compared to 62 pg/ml of the pre-filtration blood plasma as a control.

EXAMPLE 22

A non-woven fabric comprised of polyethylene terephthalate fibers having an average fiber diameter of 1.7 μm is produced from chips of polyethylene terephthalate having a water content of 13 ppm in substantially the same manner as in Example 1. The CWST value of the non-woven fabric is 60 dyn/cm. The average pore diameter of the non-woven fabric is 9.4 μm. The total pore volume and the total pore surface area of the non-woven fabric are 0.91 ml/ml of the non-woven fabric and 0.88 m$^2$/ml of the non-woven fabric, respectively. The sum of respective pore volumes of pores of the non-woven fabric which have a pore diameter of from 1 to 30 μm is 98%, based on the total pore volume. The surface electric charge of the non-woven fabric is −25.5 μeq/g. The non-woven fabric is packed in a container having a blood inlet and a blood outlet and having an effective filtration cross-sectional area of 49 mm×49 mm so that the thickness of the packed non-woven fabric (main filter medium) becomes 3.3 mm (packing density: 0.15 g/cm$^3$) to obtain a filter apparatus for selectively removing leukocytes.

513 ml of blood prepared by adding 63 ml of CPD (citrate phosphate dextrose) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 25° C. Then, the red cell product is filtered by the above-produced filter apparatus for selectively removing leukocytes.

As a result of the filtration conducted in substantially the same manner as in Example 21, it is found that the leukocyte residual ratio is $10^{-4.9}$ and the pressure loss at the time of completion of the filtration is 50 mmHg. Further, the blood sampled from the blood outlet is subjected to a measurement of the kinin concentration of the plasma as described in Example 1. The kinin concentration of the plasma is 725 pg/ml, which indicates that the increase in kinin concentration of the plasma upon being contacted with the non-woven fabric is favorably very small as compared to 73 pg/ml of the pre-filtration blood plasma as a control.

COMPARATIVE EXAMPLE 12

A non-woven fabric comprised of polyethylene terephthalate fibers having an average fiber diameter of 1.7 μm is produced from chips of polyethylene terephthalate having a water content of 50 ppm in substantially the same manner as in Comparative Example 1. The CWST value of the non-woven fabric is 62 dyn/cm. The average pore diameter of the non-woven fabric is 32.2 μm. The total pore volume and the total pore surface area of the non-woven fabric are 0.40 ml/ml of the non-woven fabric and 0.50 m$^2$/ml of the non-woven fabric, respectively. The sum of respective pore volumes of pores of the non-woven fabric which have a pore diameter of from 1 to 30 μm is 60%, based on the total pore volume. The surface electric charge of the non-woven fabric is −42.6 μeq/g. The non-woven fabric is packed into a container having a blood inlet and a blood outlet and having an effective filtration cross-sectional area of 49 mm×49 mm so that the thickness of the packed nonwoven fabric (main filter medium) becomes 3.3 mm (packing density: 0.15 g/cm$^3$) to obtain a filter apparatus for selectively removing leukocytes.

513 ml of blood prepared by adding 63 ml of CPD (citrate phosphate dextrose) solution to 450 ml of whole blood is subjected to centrifugation within 8 hours after collect%on of the whole blood to separate 243 ml of platelet-enriched plasma from the whole blood, thereby obtaining a red cell product. The red cell product (hematocrit: 68%) is stored at 4 ° C. for 15 days, and then allowed to stand at room temperature (26.5° C.) until the temperature of the product reaches 25° C. Then, the red cell product is filtered by the above-produced filter apparatus for selectively removing leukocytes.

As a result of the filtration conducted in substantially the same manner as in Example 21, it is found that the leukocyte residual ratio is $10^{-2.1}$ and the pressure loss at the time of completion of the filtration is 28 mmHg. Further, the blood sampled from the blood outlet is subjected to a measurement of the kinin concentration of the plasma as described in Example 1. The kinin concentration of the plasma is 5,700 pg/ml, which indicates that the increase in kinin concentration of the plasma upon being contacted with the non-woven fabric is unfavorably very large as compared to 73 pg/ml of the pre-filtration blood plasma as a control.

EXAMPLE 23

A non-woven fabric comprised of polyethylene terephthalate fibers having an average fiber diameter of 1.6 μm is produced from chips of polyethylene terephthalate having a water content of 13 ppm in substantially the same manner as in Example 1. The CWST value of the non-woven fabric is 60 dyn/cm. The average pore diameter of the non-woven fabric is 9.2 μm. The total pore volume and the total pore surface area of the non-woven fabric are 0.82 ml/ml of the non-woven fabric and 0.92 m$^2$/ml of the non-woven fabric, respectively. The sum of respective pore volumes of pores of the non-woven fabric which have a pore diameter of from 1 to 30 μm is 98%, based on the total pore volume. The surface electric charge of the non-woven fabric is −23.6 μeq/g. The non-woven fabric is packed as a main filter medium in a container having a blood inlet and a blood outlet and having an effective filtration cross-sectional area of 49 mm×49 mm so that the thickness of the packed non-woven fabric (main filter medium) becomes 3.3 mm (packing density: 0.16 g/cm$^3$). Further, a preliminary filter medium of a non-woven fabric produced from chips of polyethylene terephthalate having a water content of 13 ppm and having an average fiber diameter of 2.4 μm and an average pore diameter of 30 μm is packed in the container, upstream of the main filter medium with respect to the direction from the inlet side to the outlet side so that the thickness of the preliminary filter medium is 0.7 mm. Thus, a filter apparatus for selectively removing leukocytes, which has a thickness of 4 mm and is comprised of the main filter medium and the preliminary filter medium, is obtained.

517.5 ml of blood prepared by adding 67.5 ml of ACD-A (acid citrate dextrose-A) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 25° C. Then, the red cell product is filtered by the above-produced filter apparatus for selectively removing leukocytes.

As a result of the filtration conducted in substantially the same manner as in Example 21, it is found that the leukocyte residual ratio is $10^{-4.5}$ and the pressure loss at the time of completion of the filtration is 22 mmHg. Further, the blood sampled from the blood outlet is subjected to the measurement of the kinin concentration of the plasma as described in Example 1. The kinin concentration of the plasma is 872 pg/ml, which indicates that the increase in kinin concentration of the plasma upon being contacted with the non-woven fabric is favorably very small as compared to 73 pg/ml of the pre-filtration blood plasma as a control.

COMPARATIVE EXAMPLE 13

A non-woven fabric comprised of polyethylene terephthalate fibers having an average fiber diameter of 1.7 μm is produced from chips of polyethylene terephthalate having a water content of 53 ppm in substantially the same manner as in Comparative Example 1. The CWST value Of the non-woven fabric is 60 dyn/cm. The average pore diameter of the non-woven fabric is 12.5 μm. The total pore volume and the total pore surface area of the non-woven fabric are 0.86 ml/ml of the non-woven fabric and 0.88 m$^2$/ml of the non-woven fabric, respectively. The sum of respective pore volumes of pores of the non-woven fabric which have a pore diameter of from 1 to 30 μm is 98%, based on the total pore volume. The surface electric charge of the non-woven fabric is −41.2 μeq/g. The non-woven fabric is packed as a main filter medium into a container having a blood inlet and a blood outlet and having an effective filtration cross-sectional area of 49 mm×49 mm so that the thickness of the packed non-woven fabric (main filter medium) becomes 3.3 mm (packing density: 0.18 g/cm$^3$). Further, a preliminary filter medium of a non-woven fabric produced from chips of polyethylene terephthalate having a water content of 13 ppm and having an average fiber diameter of 2.4 μm, an average pore diameter of 30 μm and a surface electric charge of −22.6 μeq/g is packed in the container, upstream of the main filter medium with respect to the direction from the inlet side to the outlet side so that the thickness of the preliminary filter medium is 0.7 mm. Thus, a filter apparatus for selectively removing leukocytes, which has a thickness of 4 mm and is comprised of the main filter medium and the preliminary filter medium, is obtained.

517.5 ml of blood prepared by adding 67.5 ml of ACD-A (acid citrate dextrose-A) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 25° C. Then, the red cell product is filtered by the above-produced filter apparatus for selectively removing leukocytes.

As a result of the filtration conducted in substantially the same manner as in Example 21, it is found that the leukocyte residual ratio is $10^{-4.9}$ and the pressure loss at the time of completion of the filtration is 22 mmHg. Further, the blood sampled from the blood outlet is subjected to the measurement of the kinin concentration of the plasma as described in Example 1. The kinin concentration of the plasma is 4,500 pg/ml, which indicates that the increase in kinin concentration of the plasma upon being contacted with the non-woven fabric is unfavorably very large as compared to 73 pg/ml of the pre-filtration blood plasma as a control.

COMPARATIVE EXAMPLE 14

A non-woven fabric comprised of polyethylene terephthalate fibers having an average fiber diameter of 1.8 μm is produced from chips of polyethylene terephthalate having a water content of 15 ppm in substantially the same manner as in Example 1. The CWST value of the non-woven fabric is 60 dyn/cm. The average pore diameter of the non-woven fabric is 12.5 μm. The total pore volume and the total pore surface area of the non-woven fabric are 0.86 ml/ml of the non-woven fabric and 0.89 m$^2$/ml of the non-woven fabric, respectively. The sum of respective pore volumes of pores of the non-woven fabric which have a pore diameter of from 1 to 30 μm is 97%, based on the total pore volume. The surface electric charge of the non-woven fabric is −23.8 μeq/g. The non-woven fabric is packed as a main filter medium into a container having a blood inlet and a blood outlet and having an effective filtration cross-sectional area of 49 mm×49 mm so that the thickness of the packed non-woven fabric (main filter medium) becomes 3.3 mm (packing density: 0.18 g/cm$^3$). Further, a preliminary filter medium of a non-woven fabric produced from chips of polyethylene terephthalate having a water content of 55 ppm and having an average fiber diameter of 2.4 μm, an average pore diameter of 30 μm and a surface electric charge of −50.0 μeq/g is packed in the container, upstream of the main filter medium with respect to the direction from the inlet side to the outlet side so that the thickness of the preliminary filter medium is 0.7 mm. Thus, a filter apparatus for selectively removing leukocytes, which has a thickness of 4 mm and is comprised of the main filter medium and the preliminary filter medium, is obtained.

517.5 ml of blood prepared by adding 67.5 ml of ACD-A (acid citrate dextrose-A) solution to 450 ml of whole blood is subjected to centrifugation within 8 hours after collection of the whole blood to separate 243 ml of platelet-enriched plasma from the whole blood, thereby obtaining a red cell product. The red cell product (hematocrit: 68%) is stored at 4° C. for 15 days, and then allowed to stand at room temperature (26.5° C.) until the temperature of the product reaches 25° C. Then, the red cell product is filtered by the above-produced filter apparatus for selectively removing leukocytes.

As a result of the filtration conducted in substantially the same manner as in Example 21, it is found that the leukocyte residual ratio is $10^{-4.9}$ and the pressure loss at the time of completion of the filtration is 22 mmHg. Further, the blood sampled from the blood outlet is subjected to the measurement of the kinin concentration of the plasma as described in Example 1. The kinin concentration of the plasma is 7,300 pg/ml, which indicates that the increase in kinin concentration of the plasma upon being contacted with the non-woven fabric is unfavorably very large as compared to 73 pg/ml of the pro-filtration blood plasma as a control.

Example 24

A non-woven fabric comprised of polyethylene terephthalate fibers having an average fiber diameter of 1.7 μm is produced from chips of polyethylene terephthalate having a water content of 13 ppm in substantially the same manner as in Example 1. The CWST value of the non-woven fabric is 58 dyn/cm. The average pore diameter of the non-woven fabric is 9.4 μm. The total pore volume and the total pore surface area of the non-woven fabric are 0.81 ml/ml of the non-woven fabric and 0.91 m$^2$/ml of the non-woven fabric, respectively. The sum of respective pore volumes of pores of the non-woven fabric which have a pore diameter of from 1 to 30 μm is 98%, based on the total pore volume. The surface electric charge of the non-woven fabric is −25.5 μeq/g. The non-woven fabric is cut into a size of 20 cm×240 cm, and wound to obtain a roll (having a length of 240 cm) of the non-woven fabric having a hollow portion at center thereof as a blood channel extending from the upper to the lower ends of the roll. The roll of the non-woven fabric is packed into a cylindrical container (having a blood inlet and an outlet for a filtrate at both ends thereof) of 5 cm (diameter)×20 cm at a packing density of 0.05 g/cm$^3$. The upper and the lower ends of the roll are sealed with polyurethane sealants. The polyurethane sealant for the lower end has an opening at the center thereof corresponding to the blood channel of the roll. Thus, an apparatus is obtained which is so designed that when blood is introduced thereto through the inlet, the blood enters the fabric roll from the periphery of the roll, passes through the fabric while being filtered, and goes into the hollow portion (blood channel) positioned at the center of the roll, and the filtered blood in the blood channel is withdrawn from the outlet of the apparatus. The thus obtained apparatus for selectively removing leukocytes is connected to a blood circuit including a pump and a drip chamber, the blood circuit being connected to a blood pool. From the blood pool, 4 liters of blood as obtained in Example 23 using anticoagulant ACD-A is flowed through the apparatus at a flow rate of 50 ml/min to effect removal of leukocytes.

As a result of the filtration conducted in substantially the same manner as in Example 21, found that the leukocyte residual ratio is $10^{-4.9}$ and the pressure loss at the time of completion of the it is filtration is 85 mmHg. Further, the blood sampled from the blood outlet is subjected to the measurement of the kinin concentration of the plasma as described in Example 1. The kinin concentration of the plasma is 872 pg/ml, which indicates that the increase in kinin concentration of the plasma upon Being contacted with the non-woven fabric is favorably very small as compared to 61 pg/ml of the pre-filtration blood plasma as a control.

EXAMPLE 25

The non-woven fabric of polyethylene terephthalate as employed in Comparative Example 2 is subjected to the conventional radiation-graft copolymerization as performed in Comparative Example 5, using an aqueous solution containing 2% by weight of 2-hydroxyethyl methacrylate, 2% by weight of N,N-dimethylaminoethyl methacrylate, 0.012% by weight of methacrylic acid and 0.4% by weight of t-butanol. The grafting degree is 15% as determined by the difference between the pregrafting weight and the post-grafting weight. The CWST value of the non-woven fabric is 98 dyn/cm. The average pore diameter of the non-woven fabric is 12.3 μm. The total pore volume and the total pore surface area of the non-woven fabric are 0.86 ml/ml of the non-woven fabric and 0.88 m$^2$/ml of the non-woven fabric, respectively. The sum of respective pore volumes of pores of the non-woven fabric which have a pore diameter of from 1 to 30 μm is 96%, based on the total pore volume. The surface electric charge of the non-woven fabric cannot be accurately measured by the method of Example 1 because the amount of positive charge is apparently greater than that of negative charge. Thus, it is not greater than 3 μeq/g. The total amount of negative charge measured by a dye adsorption using safranin O is about 9 μeq/g in absolute value. The non-woven fabric is further subjected to measurement of an increase in kinin of a blood material upon being contacted with the non-woven fabric as described in Example 1. The kinin concentration of the plasma is 400 pg/ml, which indicates that the increase in kinin concentration of the plasma upon being contacted with the non-woven fabric is favorably very small as compared to that of the control noted in Example 1.

EXAMPLE 26

As a polymeric, porous substrate for an adsorptive composite, a water-insoluble polyvinyl alcohol gel having an average particle diameter of 100 μm, a vinyl alcohol unit (qOH) per unit weight of 6.0 meq/g and an average pore size of $5 \times 10^6$ in terms of an exclusion limit molecular weight is employed.

For determining an average pore diameter and a pore volume characteristic of the polyvinyl alcohol gel, measurement is done using Micromeritics Pore Sizer 9320, manufactured and sold by Shimadzu Corporation, Japan), and results of the measurement are analyzed by means of Pore Plot System 9320-PC2 (V. 1.0, manufactured and sold by Shimadzu Corporation, Japan). The analysis shows that the average pore diameter of the polyvinyl alcohol gel is 1,120 Å, and the sum of respective pore volumes of pores having a pore diameter of 100 to 5,000 Å is 92.5%, based on the total pore volume. When the above-mentioned average pore diameter is defined as "D", the sum of respective pore volumes of pores having a pore diameter of 0.5 D to 2.0 D is 64.1%, based on the total pore volume. The specific surface area of the polyvinyl alcohol gel is 180.6 m²/g as measured by nitrogen gas adsorption method [BET (S. Brunauer-Emmett-Teller) method].

100 g (on dry basis) of the polyvinyl alcohol gel is treated with epichlorohydrin, to thereby obtain an epoxy-activated polyvinyl alcohol gel having an epoxy equivalent of 116.6 μeq/ml of the polyvinyl alcohol gel.

100 ml of the epoxy-activated polyvinyl alcohol gel is suspended in a mixture containing 1.6 g (1 w/v %) of dextran sulfate having a molecular weight of 500,000 and a sulfur content of 18.2 wt %, 12.8 ml (8 v/v %) of dimethylacetamide, 1.7 ml of dimethylamine and 128 ml of an aqueous 0.1M sodium hydroxide solution. The resultant suspension is heated at 50° C. for 16 hours, to thereby obtain an adsorptive composite having, on a surface thereof including a pore surfaces, dimethylamino groups and dextran sulfate. The surface electric charge of the obtained adsorptive composite is determined according to the salt-splitting, neutralization titration method and the determined value is −3.0 μeq/g.

After plasma has been contacted with the above-prepared adsorptive composite, with respect to an increase in kinin concentration of the plasma, substantially the same measurement as in Example 1, and control experiment are performed, except that the above-obtained adsorptive composite is used as a porous element instead of the non-woven fabric. As a result, it is found that the kinin concentration is 227 pg/ml, and that substantially no increase in kinin concentration of the plasma is observed as compared to the control experiment.

Then, the above-obtained adsorptive composite is packed in a container having an inlet and an outlet for plasma to be subjected to adsorption-filtration, each of which has a mesh for preventing pieces of the adsorptive composite from leaking out of the container, to thereby obtain a filter apparatus. The amount of packed adsorptive composite is 1 ml.

8 ml of plasma from a healthy human is introduced to the filter apparatus from the inlet, which plasma has been obtained under conditions of heparin concentration of 2,000 IU/ml, and the introduced plasma is flowed at a constant rate of 0.06 ml/min. The flowed-out plasma is successively collected at a fraction size of 1 ml to obtain 8 ml in total. The formation and decomposition of kinin in the collected plasma are stopped in substantially the same manner as in the batch method. The highest kinin concentration among those of the collected fractions is taken as "kinin value" in the column flow, and the kinin value is found to be only 126 pg/ml.

EXAMPLE 27

10 ml of the same polyvinyl alcohol gel as used in Example 26 is immersed in 10% aqueous ethanol solution containing 2 w/v % of 2-sulfoethyl sodium methacrylate, and the immersed polyvinyl alcohol gel is exposed to gamma rays of 25.0 kGy. Thus, an adsorptive composite is obtained.

The surface electric charge of the obtained adsorptive composite is −12.3 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 120.3 pg/ml, and that substantially no increase in kinin concentration of the plasma is observed as compared to the control experiment.

Further, with respect to kinin value, substantially the same measurement as in Example 1 is performed, and the kinin value is found to be only 45.6 pg/ml.

EXAMPLE 28

A polyvinyl alcohol gel of the same type as in Example 26, except that it has not yet been epoxy-activated, has a surface electric charge of −1.2 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 277 pg/ml, and that substantially no increase in kinin concentration of the plasma is observed as compared to the control experiment.

Further, with respect to kinin value, substantially the same measurement as in Example 1 is performed, and the kinin value is found to be only 87 pg/ml.

EXAMPLE 29

A water-insoluble polyvinyl alcohol gel is used, which has an average pore diameter of 2,200 Å, and wherein the sum of respective pore volumes of pores having a pore diameter of 100 to 5,000 Å is 88.6%, based on the total pore volume and the sum of respective pore volumes of pores having a pore diameter of 0.5 D to 2.0 D is 62.3%, based on the total pore volume. The specific surface area of the polyvinyl alcohol gel is 64.9 m²/g as measured by nitrogen gas adsorption method (BET method).

100 g (on dry basis) of the polyvinyl alcohol gel is treated with epichlorohydrin, to thereby obtain an epoxy-activated polyvinyl alcohol gel having an epoxy equivalent of 97.8 μeq/ml of the polyvinyl alcohol gel.

10 ml of the epoxy-activated polyvinyl alcohol gel is suspended in 20 ml of aqueous 0.1M sodium hydroxide solution containing 0.125 w/v % taurine. The resultant suspension is heated at 50° C. for 16 hours, to thereby obtain an adsorptive composite. The surface electric charge of the Obtained adsorptive composite is −24.0 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 285 pg/ml, and that substantially no increase in kinin concentration of the plasma is observed as compared to the control experiment.

Further, with respect to kinin value, substantially the same measurement as in Example 26 is performed, and the kinin value is found to be only 171 pg/ml.

EXAMPLE 30

In substantially the same manner as in Example 26, an adsorptive composite having, on the surface thereof, dextran sulfate and dimethylamino groups is prepared, except that the concentration of dextran sulfate is 5 w/v % instead of 1 w/v %. The surface electric charge of the adsorptive composite is −29.5 μeq/g as measured by the salt-splitting neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 680 pg/ml, and that substantially no increase in kinin concentration of the plasma is observed as compared to the control experiment.

Further, with respect to kinin value, substantially the same measurement as in Example 26 is performed, and the kinin value is found to be only 499 pg/ml.

EXAMPLE 31

10 ml of the same epoxy-activated polyalcohol gel as in Example 26 is suspended in 20 ml of 0.2M carbonate buffer (pH 9.6) containing 25 mM/liter aspartic acid. The resultant suspension is heated at 50° C. for 16 hours, to thereby obtain an adsorptive composite.

The surface electric charge of the obtained adsorptive composite is −21.5 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 203 pg/ml, and that substantially no increase in kinin concentration of the plasma is observed as compared to the control experiment.

Further, with respect to kinin value, substantially the same measurement as in Example 1 is performed, and the kinin value is found to be only 123 pg/ml.

EXAMPLE 32

An adsorptive composite is prepared in substantially the same manner as in Example 31 except that the concentration of aspartic acid is 30 mM/liter instead of 25 mM/liter.

The surface electric charge of the obtained adsorptive composite is −25.0 μeq/g as measured by the salt-splitting, neutralization titration method.

After plasma has been contacted with the above-prepared adsorptive composite, with respect to an increase in kinin of the plasma, substantially the same measurement as in Example 26 and control experiment are performed. As a result, it is found that the kinin concentration is 515 pg/ml, and that substantially no increase in kinin concentration of the plasma is observed as compared to the control experiment.

Further, with respect to kinin value, substantially the same measurement as in Example 1 is performed, and the kinin value is found to be only 226 pg/ml.

EXAMPLE 33

In substantially the same manner as in Example 26, an adsorptive composite having, on the surface thereof, dextran sulfate and dimethylamino groups is prepared, except that the concentration of dextran sulfate (negative group) is 0.1 w/v % instead of 1 w/v %.

Further, when the surface electric charge is determined according to the salt-splitting, neutralization titration method, it is found that the surface electric charge is +17.1 μeq/g as a whole although the dextran sulfate as negative charge is present in the surface of the composite.

After plasma has been contacted with the above-prepared adsorptive composite, with respect to an increase in kinin concentration of the plasma, substantially the same measurement as in Example 26 and control experiment are performed. As a result, it is found that the kinin concentration is 88 pg/ml, and that substantially no increase in kinin concentration of the plasma is observed as compared to the control experiment.

Further, with respect to kinin value, substantially the same measurement as in Example 26 is performed, and the kinin value is found to be only 71 pg/ml.

COMPARATIVE EXAMPLE 15

Substantially the same procedure as in Example 26 is performed except that the concentration of dextran sulfate is 7 w/v % instead of 1 w/v %, to thereby obtain an adsorptive composite.

The surface electric charge of the obtained adsorptive composite is −50.4 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 7,230 pg/ml, and that a remarkable increase in kinin concentration of the plasma is observed as compared to the control experiment.

Further, with respect to kinin value, substantially the same measurement as in Example 1 is performed, and the kinin value is found to be as high as 10,096 pg/ml.

COMPARATIVE EXAMPLE 16

Substantially the same procedure as in Example 27 is performed except that the concentration of 2-sulfoethyl sodium methacrylate is 10 w/v % instead of 2 w/v %, to thereby obtain an adsorptive composite.

The surface electric charge of the obtained adsorptive composite is −63.2 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 4,810 pg/ml, and that a remarkable increase in kinin concentration of the plasma is observed as compared to the control experiment.

Further, with respect to kinin value, substantially the same measurement as in Example 1 is performed, and the kinin value is found to be as high as 3,500 pg/ml.

COMPARATIVE EXAMPLE 17

Substantially the same procedure as in Example 29 is performed except that the concentration of taurin is 1.5 w/v % instead of 0,125 w/v %, to thereby obtain an adsorptive composite.

The surface electric charge of the obtained adsorptive composite is −79.9 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 5,219 pg/ml, and that remarkable increase in kinin concentration of the plasma is observed as compared to the control experiment.

Further, with respect to kinin value, substantially the same measurement as in Example 26 is performed, and the kinin value is found to be as high as 8,943 pg/ml.

COMPARATIVE EXAMPLE 18

Substantially the same procedure as in Example 31 is performed except that the concentration of aspartic acid is 50 mM/liter instead of 25 mM/liter, to thereby obtain an adsorptive composite.

The surface electric charge of the obtained adsorptive composite is −37.8 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 9,750 pg/ml, and that a remarkable increase in kinin concentration of the plasma is observed as compared to the control experiment.

Further, with respect to kinin value, substantially the same measurement as in Example 1 is performed, and the kinin value is found to be as high as 3,920 pg/ml.

COMPARATIVE EXAMPLE 19

Substantially the same procedure as in Example 31 is performed except that the concentration of aspartic acid is 60 mM/liter instead of 25 mM/liter, to thereby obtain as adsorptive composite.

The surface electric charge of the obtained adsorptive composite is −41.6 μeq/g as measured by the salt-splitting, neutralization titration method.

After plasma has been contacted with the above-prepared adsorptive composite, with respect to an increase in kinin concentration of the plasma, substantially the same measurement as in Example 26 and control experiment are performed. As a result, it is found that the kinin concentration is 11,900 pg/ml, and that a remarkable increase in kinin concentration of the plasma is observed as compared to the control experiment.

Further, With respect to kinin value, substantially the same measurement as in Example 1 is performed, and the kinin value is found to be as high as 12,100 pg/ml.

EXAMPLE 34

A hollow porous fiber of a polyacrylonitrile (PAN) homopolymer, having an inner diameter of 250 μm and an outer diameter of 320 μm, is prepared by dry spinning.

The surface electric charge of the PAN hollow porous fiber is measured as follows.

The hollow porous fiber is well washed with 80% ethanol and washings are removed. The washed fiber is sufficiently dried. 1 g of the dried fiber is immersed in 50 ml of a methanol solution containing potassium iodide in a concentration of 5% by weight. The obtained system is subjected to a reaction at 30° C. for 24 hours while shaking. After completion of the reaction, a supernatant is collected. The collected supernatant is subjected to absorption spectrometry at 359 nm and 290 nm to thereby obtain absorbances. As a control, the above-mentioned methanol solution per se is employed.

Separately, a non-woven fabric made of polypropylene and polyethylene is prepared. Onto the non-woven fabric is fixed methacrylic acid by radiation-graft polymerization in a proportion of 0,572 meq/g of the fabric, to thereby obtain a methacrylic acid-fixed non-woven fabric. Using the above-obtained methacrylic acid-fixed non-woven fabric, the same treatment with the methanol solution as described above is conducted, and subjected to absorption spectrometry to thereby obtain absorbances at 359 nm and 290 nm. The surface electric charge of the polypropylene-polyethylene non-woven fabric has been obtained beforehand using ECH-Sepharose 4B (manufactured and sold by Pharmacia Fine Chemicals AB, Sweden) as a control. From the absorbances obtained above using the methacrylic acid-fixed polypropylene-polyethylene non-woven fabric, a calibration curve is obtained with respect to the relationships between the absorbances and the quantities of surface electric charges. Using the calibration curve, the quantity of surface electric charge of the PAN hollow porous fiber is determined, and found to be −23.2 μeq/g. The zeta potential in the inside of this hollow porous fiber is measured, and found to be −1.2 mV.

Further, an increase in bradykinin concentration of a blood material upon being contacted with the PAN hollow porous fiber is measured as follows.

Whole blood is collected using CPD (citrate phosphate dextrose) as an anticoagulant and then, treated to prepare a red cell concentrate (hematocrit value: 65%). The red cell concentrate is admixed with a physiological saline containing 11.1% of ACD-A to thereby adjust a hematocrit value to 45%. Thus, a blood sample is obtained. 5 ml of the blood sample is placed in an Erlenmeyer flask made of polycarbonate. A 0.05 g specimen of the hollow fiber cut into about 5 mm in length is immersed in the blood sample. The obtained system is subjected to a reaction at 37° C. for 5 minutes. Immediately after completion of the reaction, the treated blood sample is collected, cooled with ice, and, under ice-cooled conditions, admixed with 5000 U of tradirol, 2 mg of soy bean trypsin inhibitor, 5 mg of protamine sulfate and 20 mg of sodium ethylenediaminetetraacetate to thereby obtain a mixture. At 4° C., the obtained mixture is subjected to centrifugation at 3000 rpm for 10 minutes to thereby obtain a supernatant. The kinin concentration of the supernatant is measured by a radioimmunoassay method in which kinin is precipitated with polyethyleneglycol. The kinin concentration of the supernatant is 745 pg/ml. In a control experiment in which the same operation as described above is repeated except that the PAN hollow fiber is not immersed in the blood sample, the kinin concentration of plasma as the supernatant is 65.4 pg/ml. The above results indicate that an increase in kinin concentration of plasma upon being contacted with the PAN hollow fiber is as small as only about 10 times the kinin concentration of the control.

EXAMPLE 35

A hollow porous fiber of a PAN homopolymer, having an inner diameter of 250 μm and an outer diameter of 320 μm, is prepared by dry spinning. The resultant hollow porous fiber is packed in a casing having an inner diameter of 31.6 mm and a length of 210 mm, to thereby prepare a haemodialyzer as one form of the blood-treating filter apparatus of the present invention. The packing ratio and the effective membrane area are 68.5% and 1.0 m² respectively Using the resultant haemodialyzer, dialysis of whole blood collected using heparin as an anticoagulant is conducted. The concentration of kinin in the treated blood taken at the blood outlet of the haemodialyzer is 750 pg/ml.

COMPARATIVE EXAMPLE 20

A hollow porous fiber is prepared in substantially the same manner as in Example 34 except that an acrylonitrile copolymer containing 0.05% by weight of methacrylic acid is used as a raw material.

The surface electric charge of the hollow porous fiber is measured in substantially the same manner as in Example 34, and is found to be −198.0 μeq/g. Further, an increase in kinin concentration of a blood material upon being contacted with the hollow porous fiber is measured in substantially the same manner as in Example 34. The kinin concentration of plasma as the supernatant is 12,000 pg/ml, exhibiting an increase.

COMPARATIVE EXAMPLE 21

The hollow porous fiber prepared in Comparative Example 19, having an inner diameter of 250 μm and an outer diameter of 320 μm, is packed in a casing having an inner diameter of 31.6 mm and a length of 210 mm to thereby prepare a haemodialyzer. The packing ratio and the effective membrane area are 68 5% and 10 m², respectively. Using the haemodialyzer, dialysis of whole blood collected using heparin as an anticoagulant is conducted. The concentration of kinin in the treated blood taken at the blood outlet of the haemodialyzer is 11,250 pg/ml.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A filter medium for treating a blood material selected from the group consisting of a leukocyte-containing suspension and plasma, comprising a polymeric, porous element having, in a surface portion thereof, a negative charge and having a surface electric charge of not smaller than −30 μeq/g of said polymeric, porous element.

2. The filter medium according to claim 1, for use in separating at least one substance selected from the group consisting of at least one preselected blood component, a substance foreign to blood components and a mixture thereof from said blood material, wherein said polymeric, porous element has an average pore diameter of from 1 to 100 μm and a total pore volume of from 0.4 to 0.95 ml/ml of said polymeric, porous element, and wherein a sum of respective pore volumes of pores of said polymeric, porous element which have a pore diameter of from 1 to 100 μm is 75% or more, based on said total pore volume.

3. The filter medium according to claim 2, wherein said polymeric, porous element comprises a fibrous material.

4. The filter medium according to claim 2, wherein a surface of said polymeric, porous element exhibits a contact angle of 90° or less against a liquid having a surface tension of 100 dyn/cm, as measured at 25° C.

5. The filter medium according to claim 2, wherein said polymeric, porous element comprises a synthetic polyester.

6. The filter medium according to claim 2, wherein said polymeric, porous element has a surface electric charge in a quantity of not greater than −0.001 μeq/g of said polymeric, porous element.

7. The filter medium according to claim 1, for use in separating whole blood into a blood cell product and plasma or for use in separating whole blood or plasma, each containing at least one preselected substance, into said at least one preselected substance and a remaining whole blood or plasma product substantially free of said at least one preselected substance, wherein said polymeric, porous element is a porous membrane having an average pore diameter of from 10 Å to 1.0 μm and having a water permeability of from 3.4 to 8,000 ml/hr/m²/mmHg.

8. The filter medium according to claim 7, wherein said porous membrane is a hollow fiber porous membrane having an inner diameter of from 50 to 300 μm.

9. The filter medium according to claim 7, wherein said polymeric, porous membrane comprises a material selected from the group consisting of an acrylonitrile polymer, a cellulose polymer and a methyl methacrylate polymer.

10. The filter medium according to claim 1, for use in separating whole blood or plasma, each containing at least one preselected substance, into said at least one preselected substance and a remaining whole blood or plasma substantially free of said at least one preselected substance by adsorption-filtration, wherein said polymeric, porous element is an adsorptive composite comprising a polymeric, porous substrate having, on a surface thereof including pore surfaces, functional groups capable of selectively binding said at least one preselected substance thereto, said polymeric, porous substrate having an average pore size of from 10,000 to 10,000,000 in terms of an exclusion limit molecular weight.

11. The filter medium according to claim 10, wherein said substrate has a ligand bonded to a surface of said substrate, said ligand having said functional groups.

12. The filter medium according to claim 11, wherein said ligand exhibits a negative charge.

13. The filter medium according to claim 12, wherein said substrate exhibits a positive charge.

14. The filter medium according to claim 11, wherein said ligand exhibits a positive charge.

15. The filter medium according to claim 14, wherein said substrate exhibits a negative charge.

16. The filter medium according to claim 11, wherein said ligand comprises a chain having at least one portion thereof bonded to said substrate and having a remaining unbonded portion which is flexible and movable.

17. The filter medium according to claim 10, wherein said porous element exhibits a contact angle of 20° or more against gas bubbles in water, as measured at 25° C.

18. An apparatus for selectively separating leukocytes from a leukocyte-containing suspension, comprising: a casing having an inlet side and an outlet side, said inlet side having an inlet for a leukocyte-containing suspension selected from the group consisting of whole blood, a leukocyte-containing red cell product, a leukocyte-containing platelet and a leukocyte-containing plasma product, and said outlet side having an outlet for a filtrate; and a main filter medium packed in said casing at a packing density of from 0.05 to 0.5 g/cm$^3$, said main filter medium comprising a polymeric, porous element having, in a surface portion thereof, a negative charge and having a surface electric charge of not smaller than $-30$ μeq/g of said polymeric, porous element, wherein said polymeric, porous element has an average pore diameter of from 1 to 100 μm and a total pore volume of from 0.4 to 0.95 ml/ml of said polymeric, porous element, and wherein a sum of respective pore volumes of pores of said polymeric, porous element which have a pore diameter of from 1 to 100 μm is 75% or more, based on said total pore volume.

19. The apparatus according to claim 18, wherein said polymeric, porous element has an inlet portion on said inlet side of the casing and an outlet portion opposite said inlet portion, and has an average pore diameter gradient such that said average pore diameter is substantially continuously or stepwise decreased in a direction from said inlet side to said outlet side.

20. The apparatus according to claim 18, wherein a surface of said polymeric, porous element exhibits a contact angle of 90° or less against a liquid having a surface tension of 100 dyn/cm, as measured at 25° C.

21. The apparatus according to claim 18, wherein said polymeric, porous element comprises a non-woven fabric.

22. The apparatus according to claim 21, wherein said non-woven fabric has an inlet portion on said inlet side of the casing and an outlet portion opposite said inlet portion, said non-woven fabric comprising fibers having a diameter gradient such that a fiber diameter is substantially continuously or stepwise decreased in a direction from said inlet side to said outlet side.

23. The apparatus according to claim 18, wherein said polymeric, porous element has a thickness of from 0.1 to 500 mm, and wherein said casing has a quotient of a horizontal sectional area divided by a vertical length in a range of from 10 to 500 cm.

24. The apparatus according to claim 18, further comprising a preliminary filter medium disposed upstream of said main filter medium with respect to a direction from said inlet side of the casing to said outlet side of the casing, said preliminary filter medium comprising a preliminary porous element which has, in a surface portion thereof, a negative charge and has a surface electric charge of not smaller than $-30$ μeq/g of the preliminary porous element, and which has an average pore diameter of from 1 to 400 μm, wherein a sum of respective pore volumes of pores of the preliminary porous element which have a pore diameter of from 100 to 400 μm is 30% or more, based on a total pore volume of the preliminary porous element.

25. An apparatus for separating whole blood into a blood cell product and plasma or for separating whole blood or plasma, each containing at least one preselected substance, into said at least one preselected substance and a remaining whole blood or plasma substantially free of said at least one preselected substance, comprising: a casing having an inlet for whole blood or plasma and an outlet for a filtrate; and a filter medium packed in said casing, said filter medium comprising a polymeric, porous element having, in a surface portion thereof, a negative charge and a surface electric charge of not smaller than $-30$ μeq/g of said polymeric, porous element, and wherein said polymeric, porous element is a porous membrane having an average pore diameter of from 10 Å to 1.0 μm and having a water permeability of from 3.4 to 8,000 ml/hr/m$^2$/mmHg.

26. The apparatus according to claim 25, wherein said porous membrane is a hollow fiber porous membrane having an inner diameter of from 50 to 300 μm.

27. The apparatus according to claim 25, wherein said membrane comprises a polymeric material selected from the group consisting of an acrylonitrile polymer, a cellulose polymer and a methyl methacrylate polymer.

28. A method for treating a blood selected from the consisting of a leukocyte-containing suspension and plasma, which comprises contacting a blood material with a filter medium comprising a polymeric, porous element having, in a surface portion thereof, a negative charge and having a surface electric charge of not smaller than $-30$ μeq/g of said polymeric, porous element, thereby controlling a bradykinin concentration of a contacted blood to a level not exceeding 4,000 pg/ml.

29. The method according to claim 28, for separating at least one substance selected from the group consisting of at least one preselected blood component, a substance foreign to blood components and a mixture thereof from said blood material, wherein said polymeric, porous element has an average pore diameter of from 1 to 100 μm and a total pore volume of from 0.4 to 0.95 ml/ml of said polymeric, porous element, and wherein a sum of respective pore volumes of pores of said polymeric, porous element which have a pore diameter of from 1 to 100 μm is 75% or more, based on said total pore volume 30. The method according to claim 29, wherein said preselected blood component comprises leukocytes.

31. The method according to claim 28, for use in separating whole blood into a blood cell product and plasma or for separating whole blood or plasma, each containing at least one preselected substance, into said at least one preselected substance and a remaining whole blood or plasma product substantially free of said at least one preselected substance, wherein said polymeric, porous element is a porous membrane having an average pore diameter of from 10 Å to 1.0 μm and having a water permeability of from 3.4 to 8,000 ml/hr/m²/mmHg.

32. The method according to claim 28, for separating whole blood or plasma, each containing at least one preselected substance, into said at least one preselected substance and a remaining whole blood or plasma substantially free of said at least one preselected substance by adsorption-filtration, wherein said polymeric, porous element is an adsorptive composite comprising a polymeric, porous substrate having, on a surface thereof including pore surfaces, functional groups capable of selectively binding said at least one preselected substance thereto, said polymeric, porous substrate having an average pore size of from 10,000 to 10,000,000 in terms of an exclusion limit molecular weight.

33. A method for selectively separating leukocytes from a leukocyte-containing suspension, which comprises passing a leukocyte-containing suspension through a filter apparatus, said filter apparatus comprising: a casing having an inlet side and an outlet side, said inlet side having an inlet for a leukocyte-containing suspension selected from the group consisting of whole blood, a leukocyte-containing red cell product, a leukocyte-containing platelet and a leukocyte-containing plasma product, and said outlet side having an outlet for a filtrate; and a main filter medium packed in said casing at a packing density of from 0.05 to 0.5 g/cm³, said main filter medium comprising a polymeric, porous element having, in a surface portion thereof, a negative charge and having a surface electric charge of not smaller than −30 μeq/g of said polymeric, porous element, wherein said polymeric, porous element has an average pore diameter of from 1 to 100 μm and a total pore volume of from 0.4 to 0.95 ml/ml of said polymeric, porous element, and wherein a sum of respective pore volumes of pores of said polymeric, porous element which have a pore diameter of from 1 to 100 μm is 75% or more, based on said total pore volume, thereby controlling a bradykinin concentration of a passed blood to a level not exceeding 4,000 pg/ml.

34. A method for separating whole blood into a blood cell product and plasma or for separating whole blood or plasma each containing at least one preselected substance into said at least one preselected substance and a remaining whole blood or plasma substantially free of said at least one preselected substance, which comprises passing whole blood or plasma through a separator apparatus, said separator apparatus comprising: a casing having an inlet for whole blood or plasma and an outlet for a filtrate; and a filter medium packed in said casing, said filter medium comprising a polymeric, porous element having, in a surface portion thereof, a negative charge and a surface electric charge of not smaller than −30 μeq/g of said polymeric, porous element, and wherein said polymeric, porous element is a porous membrane having an average pore diameter of from 10 Å to 1.0 μm and having a water permeability of from 3.4 to 8,000 ml/hr/m²/mmHg, thereby controlling a bradykinin concentration of a passed blood to a level not exceeding 4,000 pg/ml.

* * * * *